US012110559B2

(12) United States Patent
Jenkins et al.

(10) Patent No.: US 12,110,559 B2
(45) Date of Patent: Oct. 8, 2024

(54) DNA METHYLATION ANALYSIS TO IDENTIFY CELL TYPE

(71) Applicant: Inherent Biosciences, Inc., Salt Lake City, UT (US)

(72) Inventors: Timothy Jenkins, Heber City, UT (US); Ryan Barney, Cedar City, UT (US); Carter Norton, Provo, UT (US)

(73) Assignee: Inherent Biosciences, Inc., Salt Lake City, UT (US)

( * ) Notice: Subject to any disclaimer, the term of this patent is extended or adjusted under 35 U.S.C. 154(b) by 0 days.

(21) Appl. No.: 18/520,939

(22) Filed: Nov. 28, 2023

(65) Prior Publication Data
US 2024/0132973 A1   Apr. 25, 2024

Related U.S. Application Data

(63) Continuation of application No. PCT/US2022/032104, filed on Jun. 3, 2022.

(60) Provisional application No. 63/196,343, filed on Jun. 3, 2021.

(51) Int. Cl.
*C12Q 1/68* (2018.01)
*C12Q 1/6874* (2018.01)
*C12Q 1/6886* (2018.01)
*C12Q 1/6806* (2018.01)

(52) U.S. Cl.
CPC ......... *C12Q 1/6886* (2013.01); *C12Q 1/6874* (2013.01); *C12Q 1/6806* (2013.01); *C12Q 2600/154* (2013.01)

(58) Field of Classification Search
CPC .................................................. C12Q 1/6888
See application file for complete search history.

(56) References Cited

U.S. PATENT DOCUMENTS

| | | | |
|---|---|---|---|
| 6,998,325 B2 | 2/2006 | Yunogami |
| 10,704,089 B1 | 7/2020 | McCord |
| 11,401,552 B2 | 8/2022 | Carrell |
| 2009/0093430 A1 | 4/2009 | Lockstone |
| 2009/0246771 A1 | 10/2009 | Laird |
| 2009/0299645 A1 | 12/2009 | Colby |
| 2010/0234242 A1 | 9/2010 | Petronis |
| 2012/0220475 A1 | 8/2012 | Petronis |
| 2013/0338032 A1 | 12/2013 | Godler |
| 2014/0166486 A1 | 6/2014 | Carrell |
| 2016/0208327 A1 | 7/2016 | Carrell |
| 2019/0048418 A1 | 2/2019 | Carrell |

FOREIGN PATENT DOCUMENTS

| CN | 101360835 A | 2/2009 |
|---|---|---|
| CN | 102137938 B | 1/2015 |
| CN | 103103256 B | 10/2015 |
| CN | 101449161 B | 1/2016 |
| EP | 1213360 A1 * | 6/2002 | ........ C12Q 1/6881 |
| WO | 2003025215 A1 | 3/2003 |
| WO | 2003074730 A1 | 9/2003 |
| WO | 2007039234 A2 | 4/2007 |
| WO | 2017024311 A1 | 2/2017 |
| WO | 2019048927 A2 | 3/2019 |
| WO | 2021030725 A1 | 2/2021 |

OTHER PUBLICATIONS

International Search Report and Written Opinion for PCT/US2022/032104, mailed Nov. 25, 2022.
Irizarry et al., "Genome-wide methylation analysis of human colon cancer reveals similar hypo-and hypermethylation at unserved tissue-specific CpG shores", Nat Genet., 2009, vol. 41, No. 2, p. 178-186.
Jenkins et al. Paternal germ line aging: DNA methylation age prediction from human sperm. BMC Genomics, 2018, vol. 19(1), p. 1-10.
Jenkins et al., Age-associated sperm DNA methylation alterations: possible implications in offspring disease susceptibility, PLoS Genet. 2014, vol. 10, No. 7, p. 1-13, e1004458.
Jenkins et al., Decreased fecundity and sperm DNA methylation patterns, Fertility and sterility, 2016, vol. 105, No. 1, p. 51-57.
Jenkins et al., Pre-screening method for somatic cell contamination in human sperm epigenetic studies, Systems biology in reproductive medicine, 2018, vol. 64, No. 2, p. 146-155.
Jenkins et al., Teratozoospermia and asthenozoospermia are associated with specific epigenetic signatures, Andrology, 2016, vol. 4, No. 5, p. 843-849.
Kang et al., Reproductive Chances of Men with Azoospermia Due to Spermatogenic Dysfunction. J Clin Med., 2021, vol. 10, No. 7, p. 1-18.
Kläver et al, "DNA methylation in spermatozoa as a prospective marker in andrology", Andrology, 2013, vol. 1, No. 5, p. 731-740.
Koscinski et al., "DPY19L2 deletion as a major cause of globozoospermia," American Journal of Human Genetics, 2011, vol. 88, No. 3, p. 344-50.
Krausz et al., Novel insights into DNA methylation features in spermatozoa: stability and peculiarities, PLoS ONE, 2012, vol. 7, No. 10, e44479, p. 1-16.
Lanfranco et al., "Klinefelter's syndrome," Lancet, 2004, vol. 364, No. 9430, p. 273-8.

(Continued)

*Primary Examiner* — Kenneth R Horlick
(74) *Attorney, Agent, or Firm* — Greenberg Traurig, LLP

(57) ABSTRACT

Disclosed herein are methods of identifying a cell type by its genomic methylation pattern from a biological sample of a human subject. In some cases, the method can comprise identifying sperm and/or prostate cells. Also described herein are methods of identifying cell types for forensic analysis and for the treatment of a disease. The methods disclosed herein may comprise determining the DNA methylation pattern of DNA extracted from a semen sample. Also disclosed herein are methods of treating a disease or condition of a subject.

17 Claims, 10 Drawing Sheets

Specification includes a Sequence Listing.

(56) References Cited

OTHER PUBLICATIONS

Lee et al., "Capacitation and acrosome reactions in human spermatozoa monitored by a chlortetracycline fluorescence assay," Fertility and Sterility, 1987, vol. 48, No. 4, p. 649-58.

Leushuis et al., "Reproducibility and reliability of repeated semen analyses in male partners of subfertile couples," Fertility and Sterility, 2010, vol. 94, No. 7, p. 2631-5.

Liu et al., Identification of spermatozoa using a novel 3-plex MSRE-PCR assay for forensic examination of sexual assaults, International Journal of Legal Medicine, 2020, vol. 134, No. 6, p. 1991-2004.

Louie et al., A Genome-wide DNA Methylation Study in Azoospermic testes, ASRM Abstracts, 2014, vol. 102, No. 3, Supplement, p. e354.

Maksimovic et al., "SWAN: Subset-quantile Within Array Normalization for Illumina Infinium HumanMethylation450 Bead Chips," Genome Biology, 2012, vol. 13, No. 6, pR44, p. 1-12.

Martin-Trujillo et al., Genotype of an individual single nucleotide polymorphism regulates DNA methylation at the IrRPC3 alternative promoter, Epigenetics, 2011, vol. 6, No. 10, p. 1236-1241.

McLean et al., GREAT improves functional interpretation of cis-regulatory regions. Nat Biotechnol., 2010, vol. 28, No. 5, p. 495-501.

Mohn et al, "Genetics and epigenetics: stability and plasticity during cellular differentiation", Cell Press, 2009, p. 129-136.

Morris et al., Analysis Pipelines and Packages for Infinium Human Methylome 450 Bead Chip (450k) Data, Methods, 2015, vol. 72, p. 3-8.

Neuwinger et al., "External quality control in the andrology laboratory: an experimental multicenter trial," Fertility and Sterility, 1990, vol. 54, No. 2, p. 308-14.

Ombelet et al., Semen quality and prediction of IUI success in male subfertility: a systematic review, Reproductive BioMedicine Online, 2014, vol. 28, p. 300-309.

Pacheco et al., Integrative DNA Methylation and Gene Expression Analyses Identify DNA Packaging and Epigenetic Regulatory Genes Associated with Low Motility Sperm, PLoS One, 2011, vol. 6, No. 6, e20280, p. 1-10.

Platt, "Sequential Minimal Optimization: A Fast Algorithm for Training Support Vector Machines," Advances in kernel methods—support vector learning, 1998, 21 pages.

Rajender et al., Epigenetics, spermatogenesis, and male infertility, 2011, Mutation Research, 2011, vol. 727, p. 62-71.

Rauch et al., "DNA Methylation profiling using the methylated-CpG island recovery assay (MIRA)", Methods, 2010, vol. 62, No. 3, p. 213-217.

Sabbioni et al., "Multigene Methylation Analysis of Gastrointestinal Tumors", Mol. Diag., 2003, vol. 7, No. 3, p. 201-207.

Sanchez et al., "A new method for evaluation of the acrosome reaction in viable human spermatozoa," Andrologia, 1991, vol. 23, No. 3, p. 197-203.

Schagdarsurengin et al., Analysing the sperm epigenome: roles in early embryogenesis and assisted reproduction, Nature Reviews Urology, 2012, vol. 9, p. 609-619.

Seisenberger et al., The dynamics of genome-wide DNA methylation reprogramming in mouse primordial germ cells, Molecular Cell, 2012, vol. 48, p. 849-862.

Skinner et al., "Epigenetic transgenerational actions of environmental factors in disease etiology", Trends in Endocrinology and Metabolism, 2010, vol. 21, No. 4, p. 214-222.

Skinner al., "Role of CpG deserts in the epigenetic transgenerational inheritance of differential DNA methylation egions", BMC Genomics, 2014, vol. 15, No. 692, 6 pages.

Smith et al., illuminaio: An open source IDAT parsing tool for illumina microarrays, F1000Research, 2013, vol. 2, No. 264, p. 1-7.

Thirlwell et al., "Suffocating cancer: hypoxia-associated epimutations as targets for cancer therapy", Clinical Epigenetics, 2011, vol. 3, No. 9, p. 1-9.

Thu et al., Methylation Analysis by DNA Immunoprecipitation, J Cell Physiol, 2020, vol. 222, p. 522-531.

Tiepolo et al., "Localization of factors controlling spermatogenesis in the nonfluorescent portion of the human Y chromosome long arm," Human Genetics, 1976, vol. 34, No. 2, p. 119-24.

Urdinguio, R. G., Bayon, G. F., Dmitrijeva, M., Toraño, E. G., Bravo, C., Fraga, M. F., et al. (2015). Aberrant DNA methylation patterns of spermatozoa in men with unexplained infertility. Hum. Reprod., 2015, vol. 30, p. 1014-1028.

Ushijima, "Detection and interpretation of altered methylation patterns in cancer cells", Nature Reviews: Cancer, 2005, vol. 5, p. 223-231.

Mdaki et al., Discovery of potential DNA methylation markers for forensic tissue identification using bisulphite pyrosequencing, Electrophoresis, 2016, vol. 37, No. 21, p. 1-13.

Walsh et al., "Cytosine methylation and mammalian development", Genes & Development, 1999, vol. 13, p. 26-34.

Wang X. Stem cells in tissues, organoids, and cancers. Cell Mol Life Sci., 2019, vol. 76, No. 20, p. 4043-4070.

Yanagimachi et al., "The use of zona free animal ova as a test system for the assessment of the fertilizing capacity of human spermatozoa," Biology of Reproduction, 1976, vol. 15, No. 4, p. 471-6.

Younglai et al., "Reproductive Toxicology of Environmental Toxicants: Emerging Issues and Concerns", Current Pharmaceutical Design, 2007, vol. 13, 2.

Zhang et al., "DNA Methylation Analysis of Chromosome 21 Gene Promoters at Single Base Pair and Single Allele Resolution", PLOSOne Genetics, 2009, vol. 5, No. 3, e1000438 (15 pages).

Zini et al., "Sperm DNA damage is associated with an increased risk of pregnancy loss after IVF and ICSI: systematic review and meta-analysis," Human Reproduction, 2008, vol. 23, No. 1, p. 2663-8.

Adjoran et al., Tumour class prediction and discovery by microarray-based DNA methylation analysis, Nucleic Acids Research, 2002, vol. 30, No. 5, p. 1-9, e21.

Alexander et al., Epigenetic control of smooth muscle cell differentiation and phenotypic switching in vascular development and disease. Annu Rev Physiol. 2012, vol. 74, p. 13-40.

Aryee et al., Minfi: a flexible and comprehensive Bioconductor package for the analysis of Infinium DNA methylation microarrays. Bioinformatics, 2014, vol. 30(10), p. 1363-9.

Aston K. I., Uren P. J., Jenkins T. G., Horsager A., Cairns B. R., Smith A. D., et al., Aberrant sperm DNA methylation predicts male fertility status and embryo quality. Fertil. Steril., 2015, vol. 104, p. 1388-1397.

Aston, Ki et al., "Genome-wide sperm deoxyribonucleic acid methylation is altered in some men with abnormal chromatin packaging or poor in vitro fertilization embryogenesis", Fertil Steril., vol. 97, No. 2, p. 285-292, (2012).

Balamurugan et al., Identification of spermatozoa by tissue-specific differential DNA methylation using bisulfite modification and pyroseuqencing, Electrophoresis, Verlag Chemie, 2014, vol. 35, p. 3079-3086.

Barratt CL, et al. Diagnostic tools in male infertility—the question of sperm dysfunction. Asian journal of andrology, 201, vol. 13, p. 53-58, (2011).

Beck et al., The methylome: approaches for global DNA methylation profiling, Trends in Genetics, 2008, vol. 24, No. 5, p. 231-237.

Benchaib M. et al: "Influence of global sperm DNA methylation on IVF results", Human Reproduction, 2005, vol. 20, No. 3, p. 768-773.

Benjamini et al., "Controlling The False Discovery Rate—A Practical and Powerful Approach to Multiple Testing," Journal of the Royal Statistical Society, 1995, Series B, vol. 57, No. 1, p. 289-300.

Benner, et al., Evolution, language and analogy in functional genomics. Trends in Genetics, vol. 17, p. 414-418 (2001).

Bibikova et al. High density DNA methylation array with single CpG site resolution. Genomics, 2011, vol. 98, No. 4, p. 288-295.

Bohacek et al., Epigenetic Inheritance of Disease and Disease Risk, Neuropsychopharmacology, 2013, vol. 38, p. 220-236.

Bonde JP, et al. Relation between semen quality and fertility: a population-based study of 430 first-pregnancy planners. Lancet, 1998, vol. 352, p. 1172-1177.

(56) References Cited

OTHER PUBLICATIONS

Brazil et al., "Quality control of laboratory methods for semen evaluation in a multicenter research study," Journal of Andrology, 2004, vol. 25, No. 4, p. 645-56.
Brinkman et al., Whole-genome DNA methylation profiling using MethylCap-seq, Methods, 2010, p. 1-5.
Brooks et al., Promoter Methylation and the Detection of Breast Cancer, Cancer Causes Control, 2009, vol. 20, No. 9, p. 1539-1550.
Brutlag et al., Improved sensitivity of biological sequence database searches, Comp. App. Biosci. 6:237-245 (1990).
Burkman et al., "The hemizona assay (HZA): development of a diagnostic test for the binding of human spermatozo to the human hemizona pellucida to predict fertilization potential," Fertility and Sterility, 1988, vol. 49, No. 4, p. 688-97.
Butcher et al., AutoMeDIP-seq: A high-throughput, whole genome, DNA methylation assay, Methods, 2010, vol. 52, p. 223-231.
Caley et al., The Principles of cancer treatment by chemotherapy, Surgery, 2012, vol. 30, Issue 4, p. 186-190.
Cervan-Martin et al., Genetic Landscape of Nonobstructive Azoospermia and New Perspectives for the Clinic. J Clin Med., 2020, vol. 9, No. 2, p. 1-27.
Cooper et al., World Health Organization reference values for human semen characteristics, Human Reproduction Update, 2010, vol. 16, No. 3, p. 231-45.
Cottrell, Molecular diagnostic applications of DNA methylation technology, Clinical Biochemistry, 2004, vol. 37, Issue 7, p. 595-604.
Dam et al., "Homozygous mutation in SPATA16 is associated with male infertility in human globozoospermia," American Journal of Human Genetics, 2007, vol. 81, No. 4, p. 813-20.
Dohle et al., EAU Guidelines on Male Infertility, European Urology, 2005, vol. 48, p. 703-711.
Down et al., A Bayesian deconvolution strategy for immunoprecipitation-based DNA methylome analysis, Nat Biotechnol., 2008, vol. 26, No. 7, p. 779-785.
Duran et al., Intraueterine insemination: a systemic review of determinants of success, Human Reproduction Update, 2002, vol. 8, No. 4, p. 373-384.
Ehrlich, "DNA methylation in cancer: too much, but also too little", Oncogene, 2002, vol. 21, p. 5400-5413.
Ellnati et al., "Globozoospermia is mainly due to DPY19L2 deletion via non-allelic homologous recombination involving two recombination hotspots," Human Molecular Genetics, 2012, vol. 21,, No. 16, p. 3695-702.
Esteves et al., "Critical appraisal of World Health Organization's new reference values for human semen characteristics and effect on diagnosis and treatment of subfertile men," Urology, 2012, vol. 79, No. 1, p. 16-22.
Fainberg et al., Recent advances in understanding and managing male infertility. F1000Res. 2019, vol. 8, p. 1-8.
Filipponi et al., Perturbation of genomic imprinting in oligozoospermia. Epigenetics, 2009, vol. 4, No. 1, p. 27-30.
Galan et al., PLoS Genet., 2021, vol. 17, No. 3, p. 1-22, e1009416.
Gandini et al., "News from the European Academy of Andrology. Italian pilot study for an external quality control scheme in semen analysis and antisperm antibiotics detection," International Journal of Andrology, 2000, vol. 23, No. 1, p. 1-3.
Guerrero-Bosagna et al., "Epigenetic Transgenerational Actions of Vinclozolin on Promoter Regions of the Sperm Epigenome", PLoSOne, 2010, vol. 5, No. 9, e13100 (17 pages).
Guzick et al., "Sperm morphology, motility, and concentration in fertile and infertile men," The New England Journal of Medicine, 2001, vol. 345, No. 19, p. 1388-93.
Haas Jr et al., "Immunologic infertility: identification of patients with antisperm antibody," New England Journal of Medicine, 1980, vol. 303, No. 13, p. 722-7.
Hall et al., The WEKA Data Mining Software: An Update. SIGKDD Explorations, 2009, vol. 11, No. 1, p. 10-18.

Hammoud et al., Alterations in sperm DNA methylation patterns at imprinted loci in two classes of infertility, Fertility and Sterility, 2010, No. 94, No. 5, p. 1728-1733.
Harbuz et al., "A recurrent deletion of DPY19L2 causes infertility in man by blocking sperm head elongation and acrosome formation," American Journal of Human Genetics, 2011, vol. 88, No. 3, p. 351-61.
Houshdaran S., et al. Widespread epigenetic abnormalities suggest a broad DNA methylation erasure defect in abnormal human sperm. PloS one. 2007, vol. 2, No. 12, p. 1-9.
Ahmed et al, The role of DNA methylation in the pathogenesis of type 2 diabetes mellitus. Clin Epigenetics, 2020, vol. 12(1), p. 1-23.
Alkhaled et al., DNA methylation level of spermatozoa from subfertile and proven fertile and its relation to standard sperm parameters, Andrologia, 2018, vol. 50, No. 6, p. 1-8.
Barres et al. Acute Exercise Remodels Promoter Methylation in Human Skeletal Muscle. Cell Metab, 2012 vol. 15(3), p. 405-411.
Bartlett et al. Intra-Gene DNA Methylation Variability is a Clinically Independent Prognostic Marker in Women's Cancers. PLOS ONE, 2015, vol. 10(12), p. 1-22.
Benchaib M,. et al., Quantitation by image analysis of global DNA methylation in human spermatozoa and its prognostic value in in vitro fertilization: a preliminary study. Fertil Steril, 2003, vol. 80, No. 4, 947-953.
Benton et al. An analysis of DNA methylation in human adipose tissue reveals differential modification of obesity genes before and after gastric bypass and weight loss. Genome Biol, 2015, vol. 16(1); p. 1-21.
Cescon et al., Environmental Impact on Male (In)Fertility via Epigenetic Route. J Clin Med. 2020, vol. 9, p. 1-33.
Davegardh et al. DNA methylation in the pathogenesis of type 2 diabetes in humans. Mol Metab, 2018, vol. 14, p. 12-25.
Donkin I, Barrès R. Sperm epigenetics and influence of environmental factors. Mol Metab. 2018; vol. 14, p. 1-11.
Du et al. Comparison of Beta-value and M-value methods for quantifying methylation levels by microarray analysis. BMC Bioinformatics, 2010, vol. 11(1), p. 1-9.
Esteves SC. Evolution of the World Health Organization semen analysis manual: where are we?. Nat Rev Urol. 2022, vol. 19, No. 7, p. 439-446.
Godfrey et al. Epigenetic Gene Promoter Methylation at Birth is Associated With Child's Later Adiposity. Diabetes, 2011, vol. 60(5), p. 1528-1534.
Goldman et al. Visualizing and interpreting cancer genomics data via the Xena platform. Nat Biotechnol, 2020, vol. 38, p. 675-678.
Horvath S. DNA methylation age of human tissues and cell types. Genome Biol, 2013, vol. 14, p. 1-20.
Huber BE. Late-stage spermatids are characterized by expression of the "liver-specific" asialoglycoprotein receptor, RHL-1. Mol Pharmacol. 1992, vol. 41, No. 4, p. 639-644.
International Search Report and Written Opinion for PCT/US2022/077583, mailed Jan. 19, 2023.
Jenkins et al, "The impact of zinc and folic acid supplementation on sperm DNA methylation: results from the folic acid and zinc supplementation randomized clinical trial (FAZST)", 2022, vol. 117, Issue 1, p. 75-85.
Laqqan et al., Aberrations in sperm DNA methylation patterns of males suffering from reduced fecundity, Andrologia Blackwell, 2017, vol. 50, No. 3, p. 1-9.
Madi, et al., "The determination of tissue-specific DNA methylation patterns in forensic biofluids using bisulfite modification and pyrosequencing" Electrophoresis; vol. 33, Issue 12, pp. 1736-1745, 2012.
Marcho C, Oluwayiose OA, Pilsner JR. The preconception environment and sperm epigenetics. Andrology. 2020, vol. 8, No. 4, p. 924-942.
McSwiggen, H. M., and O'Doherty, A. M. (2018). Epigenetic reprogramming during spermatogenesis and male factor infertility. Reproduction, 2018, vol. 156, p. 9-21.
Miller et al. "A tissue specific atlas of gene promoter DNA methylation variability and the clinical value of its assessment", biorxiv.org, 2022, p. 1-27.

(56) References Cited

OTHER PUBLICATIONS

Nishiyama et al. Navigating the DNA methylation landscape of cancer. Trends Genet, 2021, vol. 37(11), p. 1012-1027.

Rahbar S, Pashaiasl M, Ezzati M, et al. MicroRNA-based regulatory circuit involved in sperm infertility. Andrologia. 2020, vol. 52(1):e13453.

Rebourcet D, Mackay R, Darbey A, et al. Ablation of the canonical testosterone production pathway via knockout of the steroidogenic enzyme HSD17B3, reveals a novel mechanism of testicular testosterone production. FASEB J., 2020, vol. 34. p. 10373-10386.

Ronn et al. A Six Months Exercise Intervention Influences the Genome-wide DNA Methylation Pattern in Human Adipose Tissue. PLOS Genet, 2013, vol. 9, Issue 6, p. 1-16, e1003572.

Schagdarsurengin U., Steger, K. Epigenetics in male reproduction: effect of paternal diet on sperm quality and offspring health. Nat Rev Urol, 2016, vol. 13, p. 1-12.

Schisterman EF, et al. A Randomized Trial to Evaluate the Effects of Folic Acid and Zinc Supplementation on Male Fertility and Live birth: Design and Baseline Characteristics. Am J Epidemiol., 2020, vol. 189, No. 1, p. 8-26.

Schlegel PN, et al Diagnosis and Treatment of Infertility in Men: AUA/ASRM Guideline Part I. J Urol., 2021, vol. 205, p. 36-43.

Schlegel PN, Sigman M, Collura B, et al. Diagnosis and treatment of infertility in men: AUA/ASRM guideline part I. Fertil Steril. 2021, vol. 115, No. 1, p. 54-61.

Selvaraju S, Ramya L, Parthipan S, Swathi D, Binsila BK, Kolte AP. Deciphering the complexity of sperm transcriptome reveals genes governing functional membrane and acrosome integrities potentially influence fertility. Cell Tissue Res. 2021; vol. 385(1), p. 207-222.

Shehu A, Mao J, Gibori GB, et al. Prolactin receptor-associated protein/17beta-hydroxysteroid dehydrogenase type 7 gene (Hsd17b7) plays a crucial role in embryonic development and fetal survival [published correction appears in Mol Endocrinol, 2008, vol. 22, p. 2268-2277.

Singh K, Jaiswal D. Human male infertility: a complex multifactorial phenotype. Reprod Sci., 2011; vol. 18, No. 5, p. 418-425.

Stuppia, L., Franzago, M., Ballerini, P. et al. Epigenetics and male reproduction: the consequences of paternal lifestyle on fertility, embryo development, and children lifetime health. Clin Epigenet, 2015, vol. 7, p. 1-15.

Tang, Q., Chen, Y., Wu, W. et al. Idiopathic male infertility and polymorphisms in the DNA methyltransferase genes involved in epigenetic marking. Sci Rep, 2017, vol. 7, p. 1-7.

Tobi et al. DNA methylation differences after exposure to prenatal famine are common and timing- and sex-specific. Hum Mol Genet, 2009, vol. 18(21), p. 4046-4053.

Turner KA, Rambhatla A, Schon S, et al. Male Infertility is a Women's Health Issue-Research and Clinical Evaluation of Male Infertility is Needed. Cells. 2020, vol. 9, No. 4, p. 1-14.

Uhlén M, Fagerberg L, Hallström BM, Lindskog C, et al. Tissue-based map of the human proteome. Science, 2015, vol. 347, Issue 6220, p. 394-403.

Vidaki et al., Discovery of potential DNA methylation markers for forensic tissue identification using bisulphite pyrosequencing, Electrophoresis, 2016, vol. 37, No. 21, p. 1-13.

Wang C, Swerdloff RS. Limitations of semen analysis as a test of male fertility and anticipated needs from newer tests. Fertil Steril., 2014, vol. 102, No. 6, p. 1-10.

Ward WS. Function of sperm chromatin structural elements in fertilization and development. Mol Hum Reprod. 2010, vol. 16(1), p. 30-36.

World Health Organization, WHO Laboratory Manual for the Examination and Processing of Human Semen, 2021, 6th ed Geneva World Health Organization.

Zhao et al. The DNA methylation landscape of advanced prostate cancer. Nat Genet, 2020, vol. 52(8), p. 778-789.

Zoghbi HY, Beaud et al. Epigenetics and Human Disease. Cold Spring Harb Perspect Biol., 2016, vol. 2, p. 1-30.

* cited by examiner

DNA METHYLATION ANALYSIS TO IDENTIFY CELL TYPE

CROSS-REFERENCE

This application is a bypass continuation of PCT/US2022/032104, filed Jun. 3, 2022, which claims the benefit of U.S. Provisional Application No. 63/196,343, filed Jun. 3, 2021, the disclosures of which are incorporated herein by reference in their entirety.

SEQUENCE LISTING

The instant application contains a Sequence Listing which has been submitted electronically in XML format and is hereby incorporated by reference in its entirety. Said XML copy, created on Nov. 28, 2023, is named 199252-715301_SL.XML and is 61,440 bytes in size.

SUMMARY OF THE INVENTION

Disclosed herein are methods comprising: a) obtaining a biological sample from a subject, wherein the biological sample comprises seminal fluid; b) extracting DNA from a sperm in the biological sample or extracting cell free DNA from the biological sample; c) detecting a methylation pattern of a region of the extracted DNA or the extracted cell free DNA from the biological sample, wherein the methylation pattern comprises the presence or the absence of methylation of at least one region of the extracted DNA or the extracted cell free DNA from Table 1, optionally wherein the detecting comprises a sodium bisulfite conversion, a sequencing, a differential enzymatic cleavage of DNA, an affinity capture of methylated DNA, an array, or any combination thereof; and d) comparing the methylation pattern of the region of the extracted DNA or the extracted cell free DNA from the biological sample to a control pattern of DNA methylation. In some embodiments, the method can be a method of detecting a sperm cell. In some embodiments, a region from Table 1 identifies a sperm cell. In some embodiments, the method can further comprise determining the presence or absence of the sperm cell in the biological sample from the subject. In some embodiments, the methylation pattern can indicate the presence or absence of a sperm cell in the biological sample. In some embodiments, the absence of methylation of the at least one region can indicate the presence of the sperm cell in the biological sample. In some embodiments, the region from Table 1 can comprise a plurality of CpG sites for methylation. In some embodiments, at least about 75% of the plurality of CpG sites for methylation can be unmethylated. In some embodiments, at least about 75% of the plurality of CpG sites for methylation can be methylated. In some embodiments, the methylation pattern can be identified in at least: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 regions of the extracted DNA or the extracted cell free DNA from Table 1. In some embodiments, the control pattern of DNA methylation can be associated with a cell type. In some embodiments, the cell type can be a sperm cell. In some embodiments, the detecting, the comparing, or both can employ a computer processor. In some embodiments, the determining can employ a computer processor for receiving and analyzing a data comprising the methylation pattern. In some embodiments, the method can further comprise performing a treatment on the subject. In some embodiments, the treatment can comprise a surgery, a hormone treatment, a vasectomy reversal, a vasectomy, a microsurgical testicular sperm extraction (microTESE), a testicular sperm extraction (TESE) a transurethral resection of the ejaculatory ducts (TURED), a circumcision, a surgical correction for scarring, a treatment for erectile dysfunction, or any combination thereof.

Also disclosed herein are methods comprising: a) obtaining a biological sample from a subject, wherein the biological sample comprises seminal fluid; b) extracting DNA from a prostate cell in the biological sample or extracting cell free DNA from the biological sample; c) detecting a methylation pattern of a region of the extracted DNA or the extracted cell free DNA from the biological sample, wherein the methylation pattern comprises a hypermethylation or a hypomethylation of at least one region of a chromosome, wherein the at least one region of the chromosome comprises: (i) a promoter of: ZFP64, MOB3B, or HLF or a portion of any of these; (ii) a gene comprising: TCAF-1, CHST-11, or ALOX-5 or a portion of any of these, or (iii) any combination of (i) and (ii); and d) comparing the methylation pattern of the at least one region of the extracted DNA or the extracted cell free DNA from the biological sample to a control pattern of DNA methylation. In some embodiments, the method can be a method of detecting a cancerous prostate cell, comprising the detecting of at least one region of hypermethylation. In some embodiments, one or more hypermethylated regions of (i), (ii) or (iii) can identify a cancerous prostate cell. In some embodiments, at least 2, 3, 4, 5, or 6 hypermethylated regions can identify a cancerous prostate cell. In some embodiments, the method can be a method of detecting a cancerous prostate cell, comprising the detecting of at least one region of hypomethylation. In some embodiments, one or more hypomethylated regions of (i), (ii) or (iii) identifies a noncancerous prostate cell. In some embodiments, 6 hypomethylated regions can identify a noncancerous prostate cell. In some embodiments, the method can be a method of detecting a cancerous prostate cell. In some embodiments, the method can further comprise determining the presence or absence of the cancerous prostate cell in the biological sample from the subject. In some embodiments, the methylation pattern can indicate the presence or absence of the cancerous prostate cell in the biological sample. In some embodiments, the methylation pattern can comprise a hypermethylation or a hypomethylation of at least 1, 2, 3, 4, 5, or 6 regions of the chromosome. In some embodiments, the control pattern of DNA methylation can be associated with a cell type. In some embodiments, the cell type can be a cancerous prostate cell. In some embodiments, the cell type can be a noncancerous prostate cell. In some embodiments, the detecting, the comparing, or both can employ a computer processor. In some embodiments, the determining can employ a computer processor for receiving and analyzing a data comprising the methylation pattern. In some embodiments, the method can further comprise performing a treatment on the subject. In some embodiments, the treatment can comprise a chemotherapy, a surgery, a radiotherapy, a hormone therapy, a tissue ablation, an immune therapy, a chemical castration, or any combination thereof.

Also disclosed herein are forensic analysis methods of identifying a gamete cell. In some embodiments, the method of identifying a gamete cell from an article can comprise: a) extracting DNA or cell free DNA from the article; b) detecting a methylation pattern of a region of the DNA or the cell free DNA, wherein the methylation pattern comprises the presence or the absence of methylation of at least one region of DNA or the cell free DNA from Table 1; c) comparing the methylation pattern of the region of DNA from the article to a control pattern of methylated DNA associated with a gamete cell; and d) determining the presence or absence of the gamete cell from the article, wherein the methylation pattern indicates the presence or absence of the gamete cell from the article, which is a method for forensic analysis. In some embodiments, the article can comprise an article of evidence. In some embodiments, the gamete cell can be a sperm cell.

Also disclosed herein are computer systems for analyzing a DNA from a prostate cell or a cell free DNA in a seminal sample obtained from a male subject. In some embodiments, the computer system can comprise: a) a device for receiving sequenced data, wherein the sequenced data comprises sequencing of: (i) a promoter of: ZFP64, MOB3B, or HLF; (ii) a gene comprising: TCAF-1, CHST-11, or ALOX-5, or (iii) any combination of (i) and (ii); and b) a device for comparing the sequenced data with a control pattern of a DNA methylation to determine the methylation of the sequenced data; and c) a device for determining a methylation pattern of the sequenced data, wherein the methylation pattern comprises a hypermethylation or a hypomethylation of (i), (ii), or (iii).

Also disclosed herein are computer systems for analyzing a DNA from a sperm cell or a cell free DNA in a seminal sample obtained from a male subject. In some embodiments, the computer system can comprise: a) a device for receiving sequenced data, wherein the sequenced data comprises sequencing of at least one region of Table 1; b) a device for comparing the sequenced data with a control pattern of a DNA methylation to determine the methylation of the sequenced data; and c) a device for determining a methylation pattern of the sequenced data, wherein the methylation pattern comprises the presence or absence of methylation of at least one region of Table 1.

Also disclosed herein are compositions comprising primers, probes, or both for detecting DNA methylation in one or more chromosomal regions selected from a region in Table 1. In some embodiments, the primers comprise any one of SEQ ID NOs: 13-46.

Also disclosed herein are compositions comprising primers, probes, or both for detecting DNA methylation in one or more chromosomal regions selected from a region in Table 4. In some embodiments, the primers comprise any one of SEQ ID NOs: 1-12.

Also disclosed herein are kits comprising the composition described above.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A shows the fragment analyzer results for cfDNA with labels representing fragment sizes in base pairs. Peaks were commonly seen in the mid hundreds all the way up to ~6,000 bps. FIG. 2B shows a bar plot depicting the effectiveness of the DNase protocol to ensure the validity of our results. FIG. 2C shows unsupervised clustering of the samples following regionalization of the data with average beta values at each CpG island (C). The type of sample (Blood, cfDNA, or treatment group) is labeled and a heatmap shows qualitative visualization of average methylation at all CpG islands tiled on the array. The clustering demonstrates that, broadly, sperm DNA and blood DNA are quite distinct and that cfDNA in the semen appears to be a combination of the two. None of the sperm DNA preparations that were employed clustered together but instead clustered based on the individual (definitive sets of three).

FIG. 3A shows a histogram depicting the relative position of significantly differentially methylated regions from our sliding window analysis in the context of nearby gene transcription start sites. FIG. 3B shows a histogram depicting the absolute distance of significantly differentially methylated regions from our sliding window analysis in the context of nearby gene transcription start sites. FIG. 3C shows a bar plot depicting the percent of the significant regions in various CpG island contexts compared to the background (the percent of the array in various CpG island context) suggesting some particular patterns of enrichment in CpG islands and shores but not outside of these regions. FIG. 3D shows the total number of CpG islands tiled on the array that were differentially methylated or not differentially methylated in the analysis. FIG. 3E shows a boxplot of each group assessed at a representative differentially methylated site demonstrating how distinct these sites were between blood and sperm with cfDNA as a mix of the two. FIG. 3F shows a boxplot of each group assessed at a representative differentially methylated site demonstrating how distinct these sites were between blood and sperm with cfDNA as a mix of the two.

DETAILED DESCRIPTION OF THE INVENTION

Definitions

Figure 1:
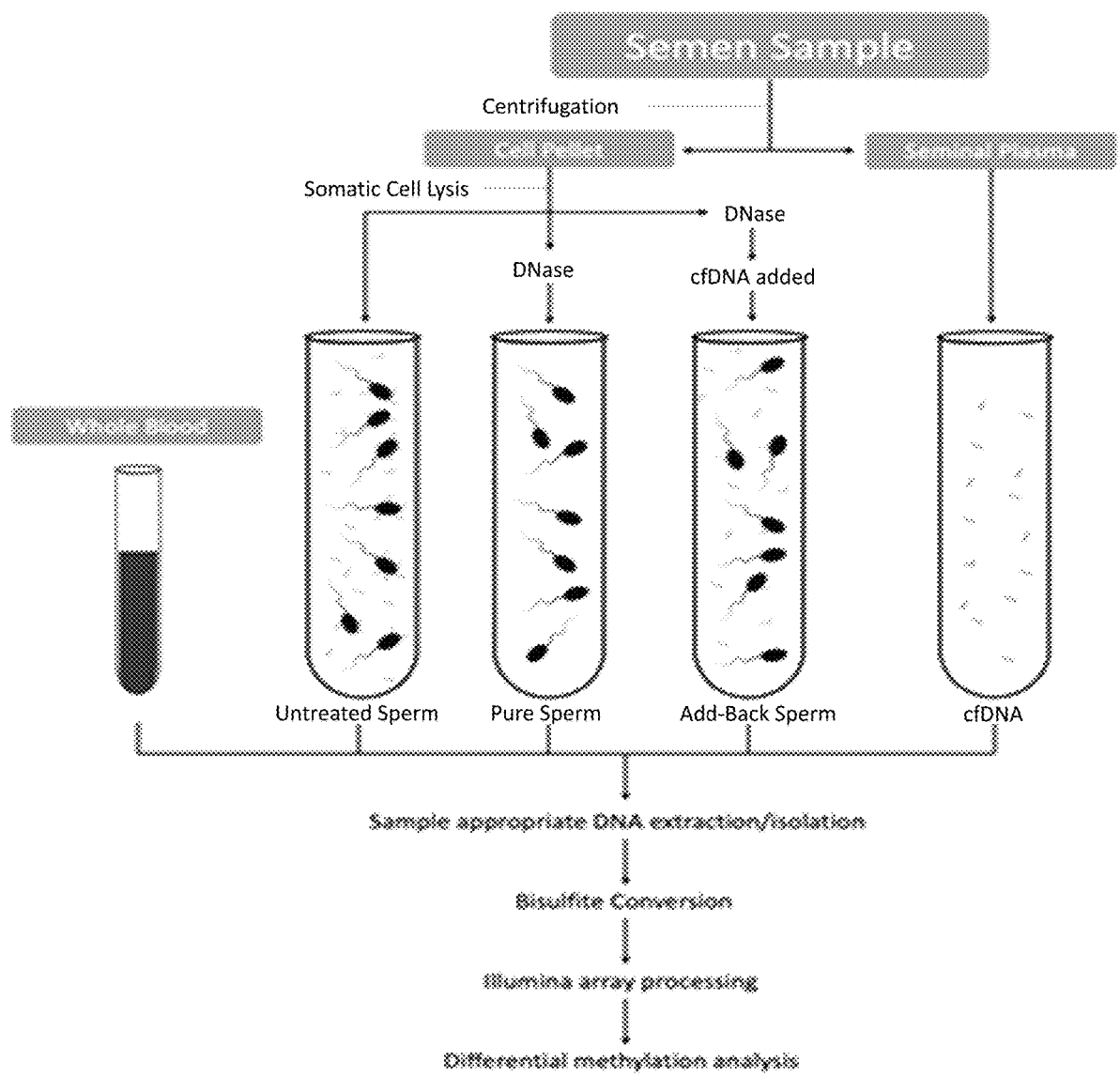
FIG. 1 shows a flow diagram of the experimental procedure used in Example 1. Each sample was split into 5 groups including cell free DNA (cfDNA), Pure sperm (DNase treated to ensure the removal of any excess cfDNA), Untreated sperm (no DNase treatment; based on previous studies in mouse this could contain both intact sperm and cfDNA fragments) Add-back sperm (which is DNase treated but cfDNA is added back to the solution) and blood.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Unless otherwise indicated, open terms for example "contain," "containing," "include," "including," and the like mean comprising.

The singular forms "a", "an", and "the" can be used herein to include plural references unless the context clearly dictates otherwise. For example, the term "a sample" includes a plurality of samples, including mixtures thereof.

As used herein, the term "about" or "approximately" a number can refer to that number plus or minus 10% of that number. In some cases, about or approximately can refer to that number plus or minus 5% of that number. The term about or approximately a range can refer to that range minus 10% of its lowest value and plus 10% of its greatest value. In some cases, the term about or approximately a range can refer to that range minus 5% of its lowest value and plus 5% of its greatest value. Alternatively, particularly with respect to biological systems or processes, the term can mean within an order of magnitude, within 5-fold, or within 2-fold, of a value. Where particular values or values of a range are described in the application and claims, unless otherwise stated the term "about" meaning within an acceptable error range for the particular value should be assumed.

The term "substantially" or "essentially" can refer to a qualitative condition that exhibits an entire or nearly total range or degree of a feature or characteristic of interest. In some cases, substantially can refer to at least about: 70%, 75%, 80%, 85%, 90%, 91%, 92%, 93%, 94%, 95%, 96%, 97%, 98%, 99% or 100% of the total range or degree of a feature or characteristic of interest.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 5 should be considered to have specifically disclosed subranges such as from 1 to 2, from 1 to 3, from 1 to 4, from 2 to 4, from 3 to 5, etc., as well as individual numbers within that range, for example, 1, 2, 3, 4, and 5. This applies regardless of the breadth of the range.

The terms "determining", "measuring", "evaluating", "assessing," "assaying," and "analyzing" are often used interchangeably herein to refer to forms of measurement and include determining if an element may be present or not (for example, detection). These terms can include quantitative, qualitative or quantitative, and qualitative determinations. Assessing can be alternatively relative or absolute. "Detecting the presence of" includes determining the amount of something present, as well as determining whether it may be present or absent.

The terms "subject," "individual," or "patient" are often used interchangeably herein. A "subject" can be a biological entity. The biological entity can be an animal, a plant, or a microorganism. The subject can be tissues, cells and their progeny of a biological entity obtained in vivo or cultured in vitro. The subject can be a mammal. The mammal can be a human. The subject may be a child, an infant, or an adult. In some cases, the human is a male. The subject can be a male human of reproductive age (e.g., older than 10 years of age). The subject can be about 1 day old to about 18 years old. In some cases, the subject can be about 1 day old to about 1 year old. In some cases, the subject can be older than 18 years of age. In some cases, the subject can be older than about 10 years, 30 years, 40 years, 50 years, 60 years, 70 year, 80 years or 90 years. The subject can be about 1, 5, 10, 15, 20, 25, 30, 35, 40, 45, 50, 55, 60, 65, 70, 75, 80, 85, 90, 95, 100, 105, 110, 115, 120, 125 or 130 years old. In some cases, the subject can be older than 60 or 65 years of age. The subject may be diagnosed or suspected of being at high risk for a disease. In some cases, the subject may not be necessarily diagnosed or suspected of being at high risk for the disease.

The term "in vitro" can be used to describe an event that takes place contained in a container for holding laboratory reagent such that it can be separated from the living biological source organism from which the material may be obtained. In vitro assays can encompass cell-based assays in which cells alive or dead are employed. In vitro assays can also encompass a cell-free assay in which no intact cells are employed.

The term "in vivo" can be used to describe an event that takes place in a subject's body.

The term "ex vivo" can be used to describe an event that takes place outside of a subject's body. An "ex vivo" assay may not be performed on a subject. Rather, it can be performed upon a sample separate from a subject. An example of an "ex vivo" assay performed on a sample can be an "in vitro" assay.

As used herein, the terms "treatment" or "treating" refers to a pharmaceutical or other intervention regimen for obtaining beneficial or desired results in the recipient. Beneficial or desired results include but are not limited to a therapeutic benefit and/or a prophylactic benefit. A therapeutic benefit may refer to eradication or amelioration of one or more symptoms or of an underlying disorder being treated. For example, a therapeutic benefit can comprise reducing the size of a tumor. Also, a therapeutic benefit can be achieved with the eradication or amelioration of one or more of the physiological symptoms associated with the underlying disorder such that an improvement may be observed in the subject, notwithstanding that the subject may still be afflicted with the underlying disorder. A prophylactic effect can include delaying, preventing, or eliminating the appearance of a disease or condition, delaying or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease may undergo treatment, even though a diagnosis of this disease may not have been made.

As used herein, the terms "effective amount" or "therapeutically effective amount" of a drug used to treat a disease can be an amount that can reduce the severity of a disease, reduce the severity of one or more symptoms associated with the disease or its treatment, or delay the onset of more serious symptoms or a more serious disease that can occur with some frequency following the treated condition. An "effective amount" may be determined empirically and in a routine manner, in relation to the stated purpose.

As used herein, the term "unit dose" or "dosage form" can be used interchangeably and can be meant to refer to pharmaceutical drug products in the form in which they are marketed for use, with a specific mixture of active ingredients and inactive components or excipients, in a particular configuration, and apportioned into a particular dose to be delivered. The term "unit dose" can also sometimes refer to the particles comprising a pharmaceutical composition or therapy, and to any mixtures involved. Types of unit doses may vary with the route of administration for drug delivery, and the substance(s) being delivered. A solid unit dose can be the solid form of a dose of a chemical compound used as a pharmaceutically acceptable drug or medication intended for administration or consumption.

As used herein, "pharmaceutically acceptable salt" can refer to pharmaceutical drug molecules, which may be formed as a weak acid or base, chemically made into their salt forms, most frequently as the hydrochloride, sodium, or sulfate salts. Drug products synthesized as salts may enhance drug dissolution, boost absorption into the bloodstream, facilitate therapeutic effects, and increase its effectiveness. Pharmaceutically acceptable salts may also facilitate the development of controlled-release dosage forms, improve drug stability, extend shelf life, enhance targeted drug delivery, and improve drug effectiveness.

An "epimutation," or "epigenetic modification," as used herein generally can refer to modifications of cellular DNA that affect gene expression without altering the DNA sequence. The epigenetic modifications can be both mitotically and meiotically stable, for example, after the DNA in a cell (or cells) of an organism has been epigenetically modified, the pattern of modification can persist throughout the lifetime of the cell and can be passed to progeny cells via both mitosis and meiosis. Therefore, with the organism's lifetime, the pattern of DNA modification and consequences thereof, can remain consistent in the cells derived from the parental cell that was originally modified. Further, if the epigenetically modified cell undergoes meiosis to generate gametes (e.g. sperm), the pattern of epigenetic modification is retained in the gametes and thus can be inherited by offspring. In other words, the patterns of epigenetic DNA modification are transgenerationally transmissible or inheritable, even though the DNA nucleotide sequence per se has not been altered or mutated. Exemplary epigenetic modifications include, but are not limited, to DNA methylation, histone modifications, chromatin structure modifications, and non-coding RNA modifications, etc. Further, the term "epigenetic modification" as used herein, may be any covalent modification of a nucleic acid base. In some cases, a covalent modification may comprise (i) adding a methyl group, a hydroxymethyl group, a carbon atom, an oxygen atom, or any combination thereof to one or more bases of a nucleic acid sequence, (ii) changing an oxidation state of a molecule associated with a nucleic acid sequence, such as an oxygen atom, or (iii) a combination thereof. A covalent modification may occur at any base, such as a cytosine, a thymine, a uracil, an adenine, a guanine, or any combination thereof. In some cases, an epigenetic modification may comprise an oxidation or a reduction. A nucleic acid sequence may comprise one or more epigenetically modified bases. An epigenetically modified base may comprise any base, such as a cytosine, a uracil, a thymine, adenine, or a guanine. An epigenetically modified base may comprise a methylated base, a hydroxymethylated base, a formylated base, or a carboxylic acid containing base or a salt thereof. An epigenetically modified base may comprise a 5-methylated base, such as a 5-methylated cytosine (5-mC). An epigenetically modified base may comprise a 5-hydroxymethylated base, such as a 5-hydroxymethylated cytosine (5-hmC). An epigenetically modified base may comprise a 5-formylated base, such as a 5-formylated cytosine (5-fC). An epigenetically modified base may comprise a 5-carboxylated base or a salt thereof, such as a 5-carboxylated cytosine (5-caC). In some cases, an epigenetically modified base may comprise a methyltransferase-directed transfer of an activated group (TAG). In some cases, DNA methylation is an epigenetic mechanism that occurs when a methyl group is added onto the C5 position of cytosine, thereby modifying gene function and affecting gene expression. Most DNA methylation occurs at cytosine residues that precede guanine residues, called CpG dinucleotides.

Epigenetic modifications may be caused by exposure to any of a variety of factors, examples of which include but are not limited to: chemical compounds e.g. endocrine disruptors such as vinclozolin; chemicals such as those used in the manufacture of plastics e.g. bisphenol A (BPA); bis(2-ethylhexyl)phthalate (DEHP); dibutyl phthalate (DBP); insect repellants such as N, N-diethyl-meta-toluamide (DEFT); pyrethroids such as permethrin; various polychlorinated dibenzodioxins, known as PCDDs or dioxins e.g. 2,3,7,8-tetrachlorodibenzo-p-dioxin (TCDD); extreme conditions such as abnormal nutrition, starvation, chemotherapeutic agents which include alkylating agents such as ifosfamide and cyclophosphamide, anthracyclines such as daunorubicin and doxorubicine, taxanes such as paclitaxel and docetaxel, epothilones, histone deacetylase inhibitors, topoisomerase inhibitors, kinase inhibitors such as gefitinib, platinum-based agents such as cisplatin, retinoids, and vinca alkaloids, etc.

A "methylation pattern" can be defined herein as the methylation of a region of genetic material (e.g., a region of a DNA molecule); methylation of a region may include methylation of a plurality of regions. Such methylation can include the absence and/or presence of methylation in a region, the extent of methylation of a region, and/or the actual methylated sequence of the region. In some cases, a methylation pattern can be a methylation pattern of one or more CpG sites within a region. In some cases, a methylation pattern can be increased or decreased methylation (e.g., hypermethylation, or hypomethylation) of one or more regions as compared to a control pattern. In some embodiments, a methylation pattern is generated with a computer program executed on a computer. In some cases, a difference or a similarity between a methylation pattern from a sample and from control sample can be detected with a computer program executed on a computer.

In some cases, a reference pattern is a methylation pattern. In some cases, a reference pattern is a control pattern. In some cases, a control pattern of methylation can be obtained from a diseased individual or a group of diseased individuals such as a group of individual with prostate cancer. In some cases, a control pattern of methylation can be obtained from a healthy individual or a group of healthy individuals without a disease or condition. In some cases, a control pattern of methylation is from a known cell type, such as a sperm cell or a cancerous prostate cell.

An "aberrant pattern of methylation" or an "aberrant pattern of DNA methylation" can be used herein as a methylation pattern that deviates from a control pattern of methylation to an extent that is indicative of a cell type or of a disease or condition. For example, an aberrant pattern of methylation may be significantly different from a control pattern of methylation, or aberrant patterns of methylation may be significantly different from control patterns of methylation. In another example, a control pattern of methylation may be significantly different from an aberrant pattern of methylation, or control patterns of methylation may be significantly different from aberrant patterns of methylation. In some cases, an aberrant pattern of methylation comprises hypomethylation, hypermethylation, or both hypermethylation and hypomethylation. In some cases, hypomethylation and hypermethylation can occur at one or more genomic sites as compared to a control pattern of methylation. In some cases, an aberrant pattern of methylation can be from a sample of a subject having or suspected of having a disease and a control pattern of methylation can be from a sample of a subject without a disease.

As used herein, the term "reference sequence", can refer to a known nucleotide sequence, e.g. a chromosomal region whose sequence is deposited at NCBI's Genbank database or other databases. A reference sequence can be a wild type sequence.

The term "nucleic acid" and "polynucleotide" can be used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., peptide nucleic acid (PNA)) which can hybridize with naturally occurring nucleic acids in a sequence specific manner analogous to that of two naturally occurring nucleic acids, e.g., can participate in Watson-Crick base pairing interactions. Naturally-occurring nucleotides can include guanine, cytosine, adenine, uracil and thymine (G, C, A, U and T, respectively). In some cases, a nucleic acid can be single stranded. In some cases, a nucleic acid can be double stranded. In some cases, a nucleic acid can comprise a ribonucleic acid (RNA), deoxyribonucleic acid (DNA), or both. In some cases, a polynucleotide may have a modified base.

"Homology" or "identity" or "similarity" can refer to sequence similarity between two peptides or between two nucleic acid molecules. Homology can be determined by comparing a position in each sequence which can be aligned for purposes of comparison. When a position in the compared sequence can be occupied by the same base or amino acid, then the molecules can be homologous at that position. A degree of homology between sequences can be a function of the number of matching or homologous positions shared by the sequences. An "unrelated" or "non-homologous" sequence shares less than 40% identity, or alternatively less than 25% identity, with one of the sequences of the disclosure. Sequence homology can refer to a % identity of a sequence to a reference sequence. As a practical matter, whether any particular sequence can be at least 50%, 60%, 70%, 80%, 85%, 90%, 92%, 95%, 96%, 97%, 98% or 99% identical to any sequence described herein (which can correspond with a particular nucleic acid sequence described herein), such particular polypeptide sequence can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence, the parameters can be set such that the percentage of identity can be calculated over the full-length of the reference sequence and that gaps in sequence homology of up to 5% of the total reference sequence can be allowed.

In some cases, the identity between a reference sequence (query sequence) and a subject sequence, also referred to as a global sequence alignment, can be determined using the FASTDB computer program-based on the algorithm of Brutlag et al. (Comp. App. Biosci. 6:237-245 (1990)). In some embodiments, parameters for a particular embodiment in which identity can be narrowly construed, used in a FASTDB amino acid alignment, can include: Scoring Scheme=PAM (Percent Accepted Mutations) 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject sequence, whichever can be shorter. According to this embodiment, if the subject sequence can be shorter than the query sequence due to N- or C-terminal deletions, not because of internal deletions, a manual correction can be made to the results to take into consideration the fact that the FASTDB program does not account for N- and C-terminal truncations of the subject sequence when calculating global percent identity. For subject sequences truncated at the N- and C-termini, relative to the query sequence, the percent identity can be corrected by calculating the number of residues of the query sequence that can be lateral to the N- and C-terminal of the subject sequence, which can be not matched/aligned with a corresponding subject residue, as a percent of the total bases of the query sequence. A determination of whether a residue can be matched/aligned can be determined by results of the FASTDB sequence alignment. This percentage can be then subtracted from the percent identity, calculated by the FASTDB program using the specified parameters, to arrive at a final percent identity score. This final percent identity score can be used for the purposes of this embodiment. In some cases, only residues to the N- and C-termini of the subject sequence, which can be not matched/aligned with the query sequence, can be considered for the purposes of manually adjusting the percent identity score. That is, only query residue positions outside the farthest N- and C-terminal residues of the subject sequence can be considered for this manual correction. For example, a 90-residue subject sequence can be aligned with a 100-residue query sequence to determine percent identity. The deletion occurs at the N-terminus of the subject sequence, and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% can be subtracted from the percent identity score calculated by the FASTDB program. If the remaining 90 residues were perfectly matched, the final percent identity can be 90%. In another example, a 90-residue subject sequence can be compared with a 100-residue query sequence. This time the deletions can be internal deletions, so there can be no residues at the N- or C-termini of the subject sequence which can be not matched/aligned with the query. In this case, the percent identity calculated by FASTDB can be not manually corrected. Once again, only residue positions outside the N- and C-terminal ends of the subject sequence, as displayed in the FASTDB alignment, which can be not matched/aligned with the query sequence can be manually corrected for.

The section headings used herein are for organizational purposes only and are not to be construed as limiting the subject matter described.

Overview

Disclosed herein are methods, procedures, systems, and kits for determining a cell type, a tissue of origin, or both. A cell type or the origin of a cell can be determined by the methylation pattern of the DNA of a cell. In some cases, a fragment of DNA can be analyzed by methylation analysis to determine a methylation pattern. The methylation pattern can be a methylation signature that can be used to determine if DNA originated from a specific cell type (e.g., sperm). The DNA can be cell bound DNA, cell free DNA (cfDNA) or both. The methylation pattern can be used to determine the origin of the DNA. For example, a method herein can be used to determine if the DNA originated from a sperm cell or a sperm precursor (any stage of spermatogenesis). The methods described herein can be used to determine the presence or absence of a cell type in a sample. In some cases, the methylation pattern can be used to determine the presence of a cancerous cell or the absence of a cancerous cell. For example, the methylation pattern from DNA can be used to determine the presence of prostate cancer by determining the presence of a cancerous prostate cell in a sample.

Disclosed herein are epigenetic methods for identifying a cell type and/or a disease or condition. Epigenetics can refer to modifiable but generally stable, heritable modifications to the DNA or chromatin packaging. Direct DNA modifications can consist of methylation alteration to the 5-carbon position of cytosine bases, generally in the context of cytosine-guanine dinucleotides (CpGs). In some embodiments, epigenetics can comprise molecular factors or processes around DNA that regulate germline activity independent of DNA sequence and can be mitotically stable. In some cases, an epigenetic process involved in sperm and or prostate abnormalities is DNA methylation. Cytosine methylation at CpG sites can alter gene expression, and within sperm these sites are associated with reduced fertility and promotion of disease in offspring. Altered sperm methylation has been shown to be a biomarker for environmental exposures that associate with various pathologies later in life. In some cases, cytosine methylation at CpG sites within prostate cells can alter gene expression, and within prostate cells aberrant methylation can be associated with cancer.

The methods, systems, and kits described herein can be used with methods of treatment for fertility, cancer, and other disease. The methods herein can be used to guide clinical care for multiple types of male infertility, which currently lack diagnostic tests. For example, the techniques described herein can be used to identify low levels of sperm in subjects, where traditional methods may miss the detection of sperm. Additionally, the techniques described herein can be used in forensics to determine a cell type of an article of evidence. The methods, systems, and kits described herein can be used with one or more computer processors to implement the steps described herein for identifying cell types and methylation patterns.

In some embodiments, a method can comprise obtaining a heterogenous cell mixture or bodily fluid (e.g., semen), extracting cell bound DNA, cell free DNA, or both. In some cases, the extracted DNA is treated with sodium bisulfate and sequenced to identify DNA methylation pattern. Specific sites can be targeted to identify their methylation pattern by sequencing, an array, PCR amplification, or any combination thereof. The identified sites with specific methylation patterns can provide a snapshot of the DNA methylation of the specific cell type and can be used to determine what pieces of DNA came from a specific cell type. For example, from a heterogenous cell mixture the presence of a sperm cell can be identified. In another example, a cancerous prostate cell can be identified from a seminal fluid sample by the methods described herein.

Methods of Detecting Cell Types

Disclosed herein are methods of detecting cell types and/or tissue types from a biological sample. In some cases, the detecting can comprise identifying a methylation pattern from the biological sample. In some embodiments, a method herein can comprise obtaining a biological sample from a subject. In some cases, a method can comprise extracting DNA from a sperm in the biological sample or extracting cell free DNA from the biological sample. In some cases, a method can comprise detecting a presence or an absence of a methylation pattern of a region of the extracted DNA or the extracted cell free DNA from the biological sample, wherein the methylation pattern comprises the presence or the absence of methylation of at least one region of the extracted DNA or the extracted cell free DNA from Table 1. In some cases, a method can comprise comparing the methylation pattern of the region of the extracted DNA or the extracted cell free DNA from the biological sample to a control pattern of DNA methylation. In some cases, the biological sample comprises seminal fluid. In some cases, the method can be a method of detecting a sperm cell. In some instances, a method can comprise determining the presence or absence of the sperm cell in the biological sample from the subject, wherein the presence or absence of the methylation pattern indicates the presence or absence of the sperm cell in the biological sample.

In some embodiments, the methods disclosed herein are methods of detecting a cell. In some cases, a cell can be a gamete cell such as a sperm cell. In some cases, a sperm cell can comprise a precursor sperm cell. For example, a precursor sperm cell can comprise a spermatogonia, a spermatocyte, a spermatid, or any combination thereof. In some cases, a cell can be a somatic cell such as a prostate cell. A prostate cell can comprise a epithelial cell or a stromal cell. In some instances, an epithelial cell can comprise a luminal secretory cell, a basal cell, a neuroendocrine cell, or a mixture thereof. In some cases, a stromal cell can comprise a smooth muscle cell, a fibroblast, or a mixture thereof. In some cases, a prostate cell can be a cancerous prostate cell.

In some cases, the methods disclosed herein are methods of detecting a sperm cell. Table 1 shows the locations of methylated regions associated with somatic cell samples (i.e. seminal cell free DNA) as compared to sperm cell DNA. In some cases, a region from Table 1 can identify a sperm cell. For example, if a region or multiple regions comprise an absence in methylation, the sample can be identified as containing sperm. In some instances, the regions in Table 1 are hypomethylated in sperm cells as compared to somatic cells. A region from Table 1 can comprise a plurality of methylated sites, for example, a region from Table 1 can comprise 1, 2, 3, 4, 5, 6, 7, 8, 9, 10, 11, 12, 13, 14 or more CpG sites for methylation. Table 2 shows the locations of specific CpGs sites associated with the methylated regions of Table 1. Table 1 depicts the chromosome number and start and stop location on the chromosome of the regions containing aberrant methylation (hypomethylation) in sperm DNA. The region designation is in reference to the reference genome is HG19 (GenBank assembly accession: GCA_000001405.1). The National Center for Biotechnology Information (NCBI) description for the genome is provided in Table 3. In some cases, the aberrant methylation in sperm DNA is hypomethylation as compared to a somatic cell. Table 1 depicts the Log 2 ratio and the Phred Scaled FDR. The Log 2 ratio is used to quantify differences in methylation, a cutoff of ≥0.2 is applied to denote differences in methylation. The phred scaled FDR is used to denote significance. An FDR of 13 is approximately equal to an adjusted p-value of 0.05. An FDR of 40 is approximately equal to an adjusted p-value of 0.001.

Table 2 shows the chromosomal location of individual CpG sites from the regions identified in Table 1. In Table 2, the "Region Designation" corresponds to the region designation in Table 1, in reference to the reference genome HG19. The "Chromosome" column indicates the chromosome number of the region of methylation, the "Location" column indicates the chromosomal location of individual CpG sites of potential methylation within the region designation. As used herein, the individual CpG sites can also be referred to herein as "sites". The "Gene" column indicates the gene associated with the region of differential methylation. The "Gene region" column provides detailed information on the CpG sites and their relation to the designated gene. Within the gene region, the destinations: TSS200 is any position within 200 basepairs (bps) of the transcription start site; TSS1500 is any position within 1500 bps of the transcription start site; 5UTR and 3UTR are untranslated regions on the 5' or 3' side of a gene, respectively; body is anywhere within the gene body; exon is within the exon (additional information is also presented, e.g., $1^{st}$ exon is the first exon on the gene); and ExonBnd is an exon boundary. In some cases, a region with multiple CpGs can have multiple annotations. In some cases, because there are multiple versions of some genes or some genes that are on the positive (+) strand can sometimes overlap with those on the negative (—) strand, both potentials can be listed since methylation is not stranded. In one example, a region and/or site can expand through a TSS200 through a 5'UTR and into a gene body, so all three designations are indicated.

TABLE 1

Top 50 regions of hypomethylation in sperm
DNA as compared to somatic cell DNA

| Region Designation | Chromosome | Start | Stop | Log2 Ratio | Phred Scaled FDR |
|---|---|---|---|---|---|
| chr1: 182921660-182923994 | chr1 | 182921660 | 182923994 | 3.19 | 80.95 |
| chr1: 18807594-18809765 | chr1 | 18807594 | 18809765 | 3.08 | 80.95 |
| chr1: 190067323-190068181 | chr1 | 190067323 | 190068181 | 3.06 | 80.95 |
| chr1: 247681102-247681932 | chr1 | 247681102 | 247681932 | 3.05 | 80.95 |
| chr1: 35441734-35443497 | chr1 | 35441734 | 35443497 | 3.37 | 80.95 |
| chr1: 9130738-9132197 | chr1 | 9130738 | 9132197 | 3.06 | 80.95 |
| chr1: 92682167-92683822 | chr1 | 92682167 | 92683822 | 3.02 | 80.95 |
| chr10: 13771107-13771466 | chr10 | 13771107 | 13771466 | 3.02 | 80.95 |
| chr10: 29084707-29085500 | chr10 | 29084707 | 29085500 | 3.09 | 80.95 |
| chr10: 85324700-85325063 | chr10 | 85324700 | 85325063 | 3.06 | 80.95 |
| chr11: 70415188-70416310 | chr11 | 70415188 | 70416310 | 3.02 | 80.95 |
| chr11: 92615215-92617119 | chr11 | 92615215 | 92617119 | 3.09 | 80.95 |
| chr12: 52472758-52474048 | chr12 | 52472758 | 52474048 | 3.07 | 80.95 |
| chr13: 36787282-36789909 | chr13 | 36787282 | 36789909 | 3.14 | 80.95 |
| chr16: 89345548-89346492 | chr16 | 89345548 | 89346492 | 3.06 | 80.95 |
| chr16: 90172237-90173535 | chr16 | 90172237 | 90173535 | 3.01 | 80.95 |
| chr17: 43318045-43319383 | chr17 | 43318045 | 43319383 | 3.20 | 80.95 |
| chr17: 74302589-74304620 | chr17 | 74302589 | 74304620 | 3.14 | 80.95 |
| chr17: 7909776-7910041 | chr17 | 7909776 | 7910041 | 3.04 | 80.95 |
| chr19: 10463037-10465258 | chr19 | 10463037 | 10465258 | 3.16 | 80.95 |
| chr19: 2926081-2927446 | chr19 | 2926081 | 2927446 | 3.16 | 80.95 |
| chr19: 36612371-36612912 | chr19 | 36612371 | 36612912 | 3.06 | 80.95 |
| chr19: 50058328-50060307 | chr19 | 50058328 | 50060307 | 3.03 | 80.95 |
| chr2: 128158047-128159059 | chr2 | 128158047 | 128159059 | 3.32 | 80.95 |
| chr20: 55684764-55685923 | chr20 | 55684764 | 55685923 | 3.13 | 80.95 |
| chr22: 32749516-32750882 | chr22 | 32749516 | 32750882 | 3.08 | 80.95 |
| chr22: 50008841-50010192 | chr22 | 50008841 | 50010192 | 3.03 | 80.95 |
| chr3: 77145918-77148085 | chr3 | 77145918 | 77148085 | 3.05 | 80.95 |
| chr3: 9027157-9027577 | chr3 | 9027157 | 9027577 | 3.25 | 80.95 |
| chr4: 128650393-128652120 | chr4 | 128650393 | 128652120 | 3.15 | 80.95 |
| chr4: 151500192-151505193 | chr4 | 151500192 | 151505193 | 3.07 | 80.95 |
| chr4: 189580331-189580876 | chr4 | 189580331 | 189580876 | 3.28 | 80.95 |
| chr4: 190731443-190732882 | chr4 | 190731443 | 190732882 | 3.13 | 80.95 |
| chr5: 121186479-121188229 | chr5 | 121186479 | 121188229 | 3.17 | 80.95 |
| chr5: 5057256-5057720 | chr5 | 5057256 | 5057720 | 3.08 | 80.95 |
| chr7: 5540163-5541567 | chr7 | 5540163 | 5541567 | 3.32 | 80.95 |
| chr7: 5645728-5648123 | chr7 | 5645728 | 5648123 | 3.15 | 80.95 |
| chr7: 64330493-64331111 | chr7 | 64330493 | 64331111 | 3.15 | 80.95 |
| chr7: 6524925-6525026 | chr7 | 6524925 | 6525026 | 3.05 | 80.95 |
| chr7: 6865886-6867075 | chr7 | 6865886 | 6867075 | 3.23 | 80.95 |
| chr7: 72741781-72743404 | chr7 | 72741781 | 72743404 | 3.13 | 80.95 |
| chr7: 75023589-75024730 | chr7 | 75023589 | 75024730 | 3.32 | 80.95 |
| chr8: 109143682-109144231 | chr8 | 109143682 | 109144231 | 3.13 | 80.95 |
| chr9: 138590204-138594308 | chr9 | 138590204 | 138594308 | 3.09 | 80.95 |

TABLE 1-continued

Top 50 regions of hypomethylation in sperm
DNA as compared to somatic cell DNA

| Region Designation | Chromosome | Start | Stop | Log2 Ratio | Phred Scaled FDR |
|---|---|---|---|---|---|
| chr9: 72129977-72131656 | chr9 | 72129977 | 72131656 | 3.12 | 80.95 |
| chrX: 129471948-129472963 | chrX | 129471948 | 129472963 | 3.14 | 80.95 |
| chrX: 134974589-134976103 | chrX | 134974589 | 134976103 | 3.04 | 80.95 |
| chrX: 31089692-31090940 | chrX | 31089692 | 31090940 | 3.19 | 80.95 |
| chrX: 40481859-40483213 | chrX | 40481859 | 40483213 | 3.43 | 80.95 |
| chrX: 42636927-42638572 | chrX | 42636927 | 42638572 | 3.04 | 80.95 |

TABLE 2

Characterization of CpG sites within the Top
50 regions of hypomethylation in sperm DNA

| Region Designation | Chromosome | Location | Gene | Gene region |
|---|---|---|---|---|
| chr1: 35441734-35443497 | chr1 | 35442238 | LOC653160 | Body |
| chr1: 35441734-35443497 | chr1 | 35442255 | LOC653160 | Body |
| chr1: 35441734-35443497 | chr1 | 35443496 | LOC653160 | Body |
| chr1: 35441734-35443497 | chr1 | 35442212 | LOC653160 | Body |
| chr1: 35441734-35443497 | chr1 | 35442839 | LOC653160 | Body |
| chr1: 35441734-35443497 | chr1 | 35442250 | LOC653160 | Body |
| chr1: 35441734-35443497 | chr1 | 35442778 | LOC653160 | Body |
| chr1: 35441734-35443497 | chr1 | 35442963 | LOC653160 | Body |
| chr1: 35441734-35443497 | chr1 | 35441734 | LOC653160 | Body |
| chr1: 182921660-182923994 | chr1 | 182923115 | SHCBP1L | TSS1500 |
| chr1: 182921660-182923994 | chr1 | 182922427 | SHCBP1L | 1stExon; 5URT |
| chr1: 182921660-182923994 | chr1 | 182921851 | SHCBP1L | Body |
| chr1: 182921660-182923994 | chr1 | 182922705 | SHCBP1L | TSS200 |
| chr1: 182921660-182923994 | chr1 | 182922593 | SHCBP1L | TSS200 |
| chr1: 182921660-182923994 | chr1 | 182923750 | SHCBP1L | TSS1500 |
| chr1: 182921660-182923994 | chr1 | 182923993 | SHCBP1L | TSS1500 |
| chr1: 182921660-182923994 | chr1 | 182921857 | SHCBP1L | Body |
| chr1: 182921660-182923994 | chr1 | 182922611 | SHCBP1L | TSS200 |
| chr1: 182921660-182923994 | chr1 | 182921688 | SHCBP1L | Body |
| chr1: 182921660-182923994 | chr1 | 182922588 | SHCBP1L | TSS200 |
| chr1: 182921660-182923994 | chr1 | 182922582 | SHCBP1L | TSS200 |
| chr1: 182921660-182923994 | chr1 | 182922502 | SHCBP1L | 1stExon; 5URT |
| chr1: 182921660-182923994 | chr1 | 182921660 | SHCBP1L | Body |
| chr1: 182921660-182923994 | chr1 | 182923215 | SHCBP1L | TSS1500 |
| chr1: 182921660-182923994 | chr1 | 182922263 | SHCBP1L | 1stExon |
| chr1: 18807594-18809765 | chr1 | 18809059 | KLHDC7A | 1stExon |

TABLE 2-continued

Characterization of CpG sites within the Top
50 regions of hypomethylation in sperm DNA

| Region Designation | Chromosome | Location | Gene | Gene region |
|---|---|---|---|---|
| chr1: 18807594-18809765 | chr1 | 18807594 | KLHDC7A | 1stExon |
| chr1: 18807594-18809765 | chr1 | 18809297 | KLHDC7A | 1stExon |
| chr1: 18807594-18809765 | chr1 | 18809604 | KLHDC7A | 1stExon |
| chr1: 18807594-18809765 | chr1 | 18809656 | KLHDC7A | 1stExon |
| chr1: 18807594-18809765 | chr1 | 18808102 | KLHDC7A | 1stExon |
| chr1: 18807594-18809765 | chr1 | 18809030 | KLHDC7A | 1stExon |
| chr1: 18807594-18809765 | chr1 | 18809764 | KLHDC7A | 1stExon |
| chr1: 18807594-18809765 | chr1 | 18809531 | KLHDC7A | 1stExon |
| chr1: 18807594-18809765 | chr1 | 18808559 | KLHDC7A | 1stExon |
| chr1: 9130738-9132197 | chr1 | 9130886 | SLC2A5 | TSS1500 |
| chr1: 9130738-9132197 | chr1 | 9131622 | | |
| chr1: 9130738-9132197 | chr1 | 9131854 | | |
| chr1: 9130738-9132197 | chr1 | 9130738 | SLC2A5 | TSS1500 |
| chr1: 9130738-9132197 | chr1 | 9131783 | | |
| chr1: 9130738-9132197 | chr1 | 9131710 | | |
| chr1: 9130738-9132197 | chr1 | 9132196 | | |
| chr1: 9130738-9132197 | chr1 | 9131028 | SLC2A5 | TSS1500 |
| chr1: 190067323-190068181 | chr1 | 190068180 | BRINP3 | Body |
| chr1: 190067323-190068181 | chr1 | 190068092 | BRINP3 | Body |
| chr1: 190067323-190068181 | chr1 | 190068053 | BRINP3 | Body |
| chr1: 190067323-190068181 | chr1 | 190068068 | BRINP3 | Body |
| chr1: 190067323-190068181 | chr1 | 190067860 | BRINP3 | Body |
| chr1: 190067323-190068181 | chr1 | 190067323 | BRINP3 | Body |
| chr1: 247681102-247681932 | chr1 | 247681749 | GCSAML | TSS200; 5URT |
| chr1: 247681102-247681932 | chr1 | 247681581 | GCSAML | TSS200; 5URT |
| chr1: 247681102-247681932 | chr1 | 247681931 | GCSAML | 5URT |
| chr1: 247681102-247681932 | chr1 | 247681781 | GCSAML | 1stExon; 5URT |
| chr1: 247681102-247681932 | chr1 | 247681584 | GCSAML | TSS200; 5URT |
| chr1: 247681102-247681932 | chr1 | 247681766 | GCSAML | 1stExon; 5URT |
| chr1: 247681102-247681932 | chr1 | 247681439 | GCSAML | TSS1500; 5URT |
| chr1: 247681102-247681932 | chr1 | 247681102 | GCSAML | TSS1500; 5URT |
| chr1: 247681102-247681932 | chr1 | 247681297 | GCSAML | TSS1500; 5URT |
| chr1: 247681102-247681932 | chr1 | 247681242 | GCSAML | TSS1500; 5URT |
| chr1: 92682167-92683822 | chr1 | 92682514 | C1orf146 | TSS1500 |
| chr1: 92682167-92683822 | chr1 | 92683454 | C1orf146 | TSS200 |
| chr1: 92682167-92683822 | chr1 | 92683821 | C1orf146 | 5URT |
| chr1: 92682167-92683822 | chr1 | 92683675 | C1orf146 | 5URT |

TABLE 2-continued

Characterization of CpG sites within the Top
50 regions of hypomethylation in sperm DNA

| Region Designation | Chromosome | Location | Gene | Gene region |
|---|---|---|---|---|
| chr1: 92682167-92683822 | chr1 | 92683061 | C1orf146 | TSS1500 |
| chr1: 92682167-92683822 | chr1 | 92683469 | C1orf146 | TSS200 |
| chr1: 92682167-92683822 | chr1 | 92683554 | C1orf146 | TSS200 |
| chr1: 92682167-92683822 | chr1 | 92683530 | C1orf146 | TSS200 |
| chr1: 92682167-92683822 | chr1 | 92682443 | C1orf146 | TSS1500 |
| chr1: 92682167-92683822 | chr1 | 92683581 | C1orf146 | 1stExon; 5URT |
| chr1: 92682167-92683822 | chr1 | 92682167 | C1orf146 | TSS1500 |
| chr1: 92682167-92683822 | chr1 | 92683403 | C1orf146 | TSS200 |
| chr2: 128158047-128159059 | chr2 | 128158047 | | |
| chr2: 128158047-128159059 | chr2 | 128158853 | | |
| chr2: 128158047-128159059 | chr2 | 128158906 | | |
| chr2: 128158047-128159059 | chr2 | 128159058 | | |
| chr2: 128158047-128159059 | chr2 | 128158601 | | |
| chr2: 128158047-128159059 | chr2 | 128158438 | | |
| chr3: 9027157-9027577 | chr3 | 9027157 | SRGAP3 | 3UTR |
| chr3: 9027157-9027577 | chr3 | 9027277 | SRGAP3 | Body |
| chr3: 9027157-9027577 | chr3 | 9027576 | SRGAP3 | Body |
| chr3: 9027157-9027577 | chr3 | 9027454 | SRGAP3 | Body |
| chr3: 77145918-77148085 | chr3 | 77148084 | ROBO2 | 5URT; Body |
| chr3: 77145918-77148085 | chr3 | 77146138 | ROBO2 | TSS1500; 5URT; Body |
| chr3: 77145918-77148085 | chr3 | 77146227 | ROBO2 | TSS1500; 5URT; Body |
| chr3: 77145918-77148085 | chr3 | 77145918 | ROBO2 | TSS1500; 5URT; Body |
| chr3: 77145918-77148085 | chr3 | 77147238 | ROBO2 | 1stExon; 5URT; Body |
| chr3: 77145918-77148085 | chr3 | 77147364 | ROBO2 | 1stExon; 5URT; Body |
| chr3: 77145918-77148085 | chr3 | 77146988 | ROBO2 | TSS200; 5URT; Body |
| chr3: 77145918-77148085 | chr3 | 77146347 | ROBO2 | TSS1500; 5URT; Body |
| chr3: 77145918-77148085 | chr3 | 77147109 | ROBO2 | TSS200; 5URT; Body |
| chr3: 77145918-77148085 | chr3 | 77147279 | ROBO2 | 1stExon; 5URT; Body |
| chr3: 77145918-77148085 | chr3 | 77146802 | ROBO2 | TSS1500; 5URT; Body |
| chr3: 77145918-77148085 | chr3 | 77147070 | ROBO2 | TSS200; 5URT; Body |
| chr4: 189580331-189580876 | chr4 | 189580875 | | |
| chr4: 189580331-189580876 | chr4 | 189580798 | | |
| chr4: 189580331-189580876 | chr4 | 189580331 | | |
| chr4: 189580331-189580876 | chr4 | 189580507 | | |
| chr4: 189580331-189580876 | chr4 | 189580633 | | |
| chr4: 128650393-128652120 | chr4 | 128650828 | SLC25A31 | TSS1500 |
| chr4: 128650393-128652120 | chr4 | 128651211 | SLC25A31 | TSS1500 |

TABLE 2-continued

Characterization of CpG sites within the Top
50 regions of hypomethylation in sperm DNA

| Region Designation | Chromosome | Location | Gene | Gene region |
|---|---|---|---|---|
| chr4: 128650393-128652120 | chr4 | 128651221 | SLC25A31 | TSS1500 |
| chr4: 128650393-128652120 | chr4 | 128651526 | SLC25A31 | TSS200 |
| chr4: 128650393-128652120 | chr4 | 128651936 | SLC25A31 | Body |
| chr4: 128650393-128652120 | chr4 | 128651532 | SLC25A31 | TSS200 |
| chr4: 128650393-128652120 | chr4 | 128652119 | SLC25A31 | Body |
| chr4: 128650393-128652120 | chr4 | 128651518 | SLC25A31 | TSS200 |
| chr4: 128650393-128652120 | chr4 | 128651206 | SLC25A31 | TSS1500 |
| chr4: 128650393-128652120 | chr4 | 128651707 | SLC25A31 | 1stExon |
| chr4: 128650393-128652120 | chr4 | 128650393 | SLC25A31 | TSS1500 |
| chr4: 128650393-128652120 | chr4 | 128651543 | SLC25A31 | TSS200 |
| chr4: 128650393-128652120 | chr4 | 128651564 | SLC25A31 | 5URT; 1stExon |
| chr4: 128650393-128652120 | chr4 | 128651500 | SLC25A31 | TSS200 |
| chr4: 190731443-190732882 | chr4 | 190731458 | | |
| chr4: 190731443-190732882 | chr4 | 190731885 | | |
| chr4: 190731443-190732882 | chr4 | 190732196 | | |
| chr4: 190731443-190732882 | chr4 | 190731443 | | |
| chr4: 190731443-190732882 | chr4 | 190732881 | | |
| chr4: 190731443-190732882 | chr4 | 190731655 | | |
| chr4: 190731443-190732882 | chr4 | 190731709 | | |
| chr4: 151500192-151505193 | chr4 | 151504920 | MAB21L2 | 1stExon; Body |
| chr4: 151500192-151505193 | chr4 | 151504138 | MAB21L2 | 5URT; 1stExon; Body |
| chr4: 151500192-151505193 | chr4 | 151504187 | MAB21L2 | 1stExon; Body |
| chr4: 151500192-151505193 | chr4 | 151501035 | LRBA | Body |
| chr4: 151500192-151505193 | chr4 | 151502935 | MAB21L2 | TSS200; Body |
| chr4: 151500192-151505193 | chr4 | 151502309 | MAB21L2 | TSS1500; Body |
| chr4: 151500192-151505193 | chr4 | 151505192 | MAB21L2 | 1stExon; Body |
| chr4: 151500192-151505193 | chr4 | 151500931 | LRBA | Body |
| chr4: 151500192-151505193 | chr4 | 151503501 | MAB21L2 | 5URT; 1stExon;Body |
| chr4: 151500192-151505193 | chr4 | 151505084 | MAB21L2 | 1stExon; Body |
| chr4: 151500192-151505193 | chr4 | 151501298 | LRBA | Body |
| chr4: 151500192-151505193 | chr4 | 151501623 | MAB21L2 | TSS1500; Body |
| chr4: 151500192-151505193 | chr4 | 151503878 | MAB21L2 | 5URT; 1stExon; Body |
| chr4: 151500192-151505193 | chr4 | 151501739 | MAB21L2 | TSS1500; Body |
| chr4: 151500192-151505193 | chr4 | 151502996 | MAB21L2 | TSS200; Body |
| chr4: 151500192-151505193 | chr4 | 151502939 | MAB21L2 | TSS200; Body |
| chr4: 151500192-151505193 | chr4 | 151501627 | MAB21L2 | TSS1500; Body |
| chr4: 151500192-151505193 | chr4 | 151500192 | LRBA | Body |

TABLE 2-continued

Characterization of CpG sites within the Top
50 regions of hypomethylation in sperm DNA

| Region Designation | Chromosome | Location | Gene | Gene region |
|---|---|---|---|---|
| chr4: 151500192-151505193 | chr4 | 151502946 | MAB21L2 | TSS200; Body |
| chr4: 151500192-151505193 | chr4 | 151503546 | MAB21L2 | 5URT; 1stExon; Body |
| chr4: 151500192-151505193 | chr4 | 151503588 | MAB21L2 | 5URT; 1stExon; Body |
| chr4: 151500192-151505193 | chr4 | 151500631 | LRBA | Body |
| chr4: 151500192-151505193 | chr4 | 151503227 | MAB21L2 | 5URT; 1stExon; Body |
| chr4: 151500192-151505193 | chr4 | 151501806 | MAB21L2 | TSS1500; Body |
| chr5: 121186479-121188229 | chr5 | 121186479 | FTMT | TSS1500 |
| chr5: 121186479-121188229 | chr5 | 121187419 | FTMT | TSS1500 |
| chr5: 121186479-121188229 | chr5 | 121188016 | FTMT | 1stExon |
| chr5: 121186479-121188229 | chr5 | 121187547 | FTMT | TSS200 |
| chr5: 121186479-121188229 | chr5 | 121187445 | FTMT | TSS1500 |
| chr5: 121186479-121188229 | chr5 | 121187598 | FTMT | TSS200 |
| chr5: 121186479-121188229 | chr5 | 121187571 | FTMT | TSS200 |
| chr5: 121186479-121188229 | chr5 | 121187367 | FTMT | TSS1500 |
| chr5: 121186479-121188229 | chr5 | 121187589 | FTMT | TSS200 |
| chr5: 121186479-121188229 | chr5 | 121187540 | FTMT | TSS200 |
| chr5: 121186479-121188229 | chr5 | 121188228 | FTMT | 1stExon |
| chr5: 121186479-121188229 | chr5 | 121187345 | FTMT | TSS1500 |
| chr5: 5057256-5057720 | chr5 | 5057705 | LINC01020 | Body |
| chr5: 5057256-5057720 | chr5 | 5057256 | LINC01020 | Body |
| chr5: 5057256-5057720 | chr5 | 5057387 | LINC01020 | Body |
| chr5: 5057256-5057720 | chr5 | 5057500 | LINC01020 | Body |
| chr5: 5057256-5057720 | chr5 | 5057690 | LINC01020 | ExonBnd; Body |
| chr5: 5057256-5057720 | chr5 | 5057719 | LINC01020 | Body |
| chr7: 75023589-75024730 | chr7 | 75024729 | TRIM73 | TSS200 |
| chr7: 75023589-75024730 | chr7 | 75023677 | TRIM73 | TSS1500 |
| chr7: 75023589-75024730 | chr7 | 75024638 | TRIM73 | TSS1500 |
| chr7: 75023589-75024730 | chr7 | 75023589 | TRIM73 | TSS1500 |
| chr7: 75023589-75024730 | chr7 | 75024676 | TRIM73 | TSS1500 |
| chr7: 75023589-75024730 | chr7 | 75024673 | TRIM73 | TSS1500 |
| chr7: 5540163-5541567 | chr7 | 5540760 | FBXL18 | Body |
| chr7: 5540163-5541567 | chr7 | 5540743 | FBXL18 | Body |
| chr7: 5540163-5541567 | chr7 | 5540163 | FBXL18 | Body |
| chr7: 5540163-5541567 | chr7 | 5540534 | FBXL18 | Body |
| chr7: 5540163-5541567 | chr7 | 5541496 | FBXL18 | Body |
| chr7: 5540163-5541567 | chr7 | 5540480 | FBXL18 | Body |
| chr7: 5540163-5541567 | chr7 | 5541566 | FBXL18 | Body |

TABLE 2-continued

Characterization of CpG sites within the Top
50 regions of hypomethylation in sperm DNA

| Region Designation | Chromosome | Location | Gene | Gene region |
|---|---|---|---|---|
| chr7: 6865886-6867075 | chr7 | 6866072 | CCZ1B | TSS200 |
| chr7: 6865886-6867075 | chr7 | 6867074 | CCZ1B | TSS1500 |
| chr7: 6865886-6867075 | chr7 | 6865965 | CCZ1B | TSS200 |
| chr7: 6865886-6867075 | chr7 | 6865989 | CCZ1B | TSS200 |
| chr7: 6865886-6867075 | chr7 | 6867070 | CCZ1B | TSS1500 |
| chr7: 6865886-6867075 | chr7 | 6866804 | CCZ1B | TSS1500 |
| chr7: 6865886-6867075 | chr7 | 6865915 | CCZ1B | 1stExon; 5URT |
| chr7: 6865886-6867075 | chr7 | 6866781 | CCZ1B | TSS1500 |
| chr7: 6865886-6867075 | chr7 | 6865886 | CCZ1B | 1stExon; 5URT |
| chr7: 6865886-6867075 | chr7 | 6866040 | CCZ1B | TSS200 |
| chr7: 6865886-6867075 | chr7 | 6866834 | CCZ1B | TSS1500 |
| chr7: 64330493-64331111 | chr7 | 64330493 | | |
| chr7: 64330493-64331111 | chr7 | 64331110 | | |
| chr7: 64330493-64331111 | chr7 | 64330785 | | |
| chr7: 64330493-64331111 | chr7 | 64330819 | | |
| chr7: 5645728-5648123 | chr7 | 5647786 | | |
| chr7: 5645728-5648123 | chr7 | 5645984 | FSCN1 | 3UTR |
| chr7: 5645728-5648123 | chr7 | 5645728 | FSCN1 | 3UTR |
| chr7: 5645728-5648123 | chr7 | 5645778 | FSCN1 | 3UTR |
| chr7: 5645728-5648123 | chr7 | 5647885 | | |
| chr7: 5645728-5648123 | chr7 | 5647920 | | |
| chr7: 5645728-5648123 | chr7 | 5647182 | | |
| chr7: 5645728-5648123 | chr7 | 5647332 | | |
| chr7: 5645728-5648123 | chr7 | 5646121 | FSCN1 | 3UTR |
| chr7: 5645728-5648123 | chr7 | 5646827 | | |
| chr7: 5645728-5648123 | chr7 | 5648122 | | |
| chr7: 5645728-5648123 | chr7 | 5647145 | | |
| chr7: 72741781-72743404 | chr7 | 72742151 | FKBP6 | TSS200 |
| chr7: 72741781-72743404 | chr7 | 72743248 | TRIM50 | TSS1500; Body |
| chr7: 72741781-72743404 | chr7 | 72742177 | FKBP6 | TSS200; 5URT; 1stExon |
| chr7: 72741781-72743404 | chr7 | 72742156 | FKBP6 | TSS2005URT; 1stExon |
| chr7: 72741781-72743404 | chr7 | 72742068 | TRIM50 | 5URT; 1stExon; TSS200 |
| chr7: 72741781-72743404 | chr7 | 72741883 | TRIM50 | 5URT; TSS1500 |
| chr7: 72741781-72743404 | chr7 | 72742188 | FKBP6 | TSS200; 5URT; 1stExon |
| chr7: 72741781-72743404 | chr7 | 72742330 | FKBP6 | 5URT; 1stExon; TSS1500; Body |
| chr7: 72741781-72743404 | chr7 | 72742709 | TRIM50 | TSS1500; ExonBnd; Body |
| chr7: 72741781-72743404 | chr7 | 72743200 | TRIM50 | TSS1500; Body |

TABLE 2-continued

Characterization of CpG sites within the Top 50 regions of hypomethylation in sperm DNA

| Region Designation | Chromosome | Location | Gene | Gene region |
|---|---|---|---|---|
| chr7: 72741781-72743404 | chr7 | 72741893 | TRIM50 | 5URT; TSS1500 |
| chr7: 72741781-72743404 | chr7 | 72741781 | TRIM50 | 5URT; TSS1500 |
| chr7: 72741781-72743404 | chr7 | 72742173 | FKBP6 | TSS200; 5URT; 1stExon |
| chr7: 72741781-72743404 | chr7 | 72742143 | FKBP6 | TSS200 |
| chr7: 72741781-72743404 | chr7 | 72741987 | TRIM50 | 5URT; TSS1500; 1stExon; TSS200 |
| chr7: 72741781-72743404 | chr7 | 72743403 | TRIM50 | TSS1500; Body |
| chr7: 72741781-72743404 | chr7 | 72741887 | TRIM50 | 5URT; TSS1500 |
| chr7: 72741781-72743404 | chr7 | 72743168 | TRIM50 | TSS1500; Body |
| chr7: 6524925-6525026 | chr7 | 6525016 | KDELR2 | TSS1500 |
| chr7: 6524925-6525026 | chr7 | 6524993 | KDELR2 | TSS1500 |
| chr7: 6524925-6525026 | chr7 | 6524998 | KDELR2 | TSS1500 |
| chr7: 6524925-6525026 | chr7 | 6524925 | KDELR2 | TSS1500 |
| chr7: 6524925-6525026 | chr7 | 6525025 | KDELR2 | TSS1500 |
| chr8: 109143682-109144231 | chr8 | 109144230 | | |
| chr8: 109143682-109144231 | chr8 | 109143682 | | |
| chr8: 109143682-109144231 | chr8 | 109144152 | | |
| chr8: 109143682-109144231 | chr8 | 109143688 | | |
| chr9: 72129977-72131656 | chr9 | 72131278 | APBA1 | Body |
| chr9: 72129977-72131656 | chr9 | 72130471 | APBA1 | Body |
| chr9: 72129977-72131656 | chr9 | 72130756 | APBA1 | Body |
| chr9: 72129977-72131656 | chr9 | 72130914 | APBA1 | ExonBnd; Body |
| chr9: 72129977-72131656 | chr9 | 72131655 | APBA1 | Body |
| chr9: 72129977-72131656 | chr9 | 72131026 | APBA1 | Body |
| chr9: 72129977-72131656 | chr9 | 72129977 | APBA1 | Body |
| chr9: 138590204-138594308 | chr9 | 138590995 | SOHLH1 | Body |
| chr9: 138590204-138594308 | chr9 | 138594241 | KCNT1 | Body |
| chr9: 138590204-138594308 | chr9 | 138591474 | SOHLH1 | TSS200 |
| chr9: 138590204-138594308 | chr9 | 138591308 | SOHLH1 | 1stExon |
| chr9: 138590204-138594308 | chr9 | 138593626 | KCNTI | TSS1500 |
| chr9: 138590204-138594308 | chr9 | 138591503 | SOHLH1 | TSS200 |
| chr9: 138590204-138594308 | chr9 | 138593952 | KCNTI | TSS200 |
| chr9: 138590204-138594308 | chr9 | 138593011 | KCNT1 | TSS1500 |
| chr9: 138590204-138594308 | chr9 | 138594185 | KCNT1 | 1stExon |
| chr9: 138590204-138594308 | chr9 | 138593860 | KCNT1 | TSS200 |
| chr9: 138590204-138594308 | chr9 | 138590204 | SOHLH1 | Body |
| chr9: 138590204-138594308 | chr9 | 138591683 | SOHLH1 | TSS1500 |
| chr9: 138590204-138594308 | chr9 | 138593815 | KCNT1 | TSS1500 |

TABLE 2-continued

Characterization of CpG sites within the Top
50 regions of hypomethylation in sperm DNA

| Region Designation | Chromosome | Location | Gene | Gene region |
|---|---|---|---|---|
| chr9: 138590204-138594308 | chr9 | 138590977 | SOHLH1 | Body; ExonBnd |
| chr9: 138590204-138594308 | chr9 | 138590270 | SOHLH1 | Body |
| chr9: 138590204-138594308 | chr9 | 138592162 | SOHLHI | TSS1500 |
| chr9: 138590204-138594308 | chr9 | 138592347 | SOHLH1 | TSS1500 |
| chr9: 138590204-138594308 | chr9 | 138591451 | SOHLH1 | TSS200 |
| chr9: 138590204-138594308 | chr9 | 138593858 | KCNT1 | TSS200 |
| chr9: 138590204-138594308 | chr9 | 138591854 | SOHLH1 | TSS1500 |
| chr9: 138590204-138594308 | chr9 | 138594307 | KCNT1 | Body |
| chr9: 138590204-138594308 | chr9 | 138593874 | KCNT1 | TSS200 |
| chr9: 138590204-138594308 | chr9 | 138593698 | KCNT1 | TSS1500 |
| chr10: 29084707-29085500 | chr10 | 29085084 | LINC00837 | TSS200; Body |
| chr10: 29084707-29085500 | chr10 | 29085104 | LINC00837 | TSS200; Body |
| chr10: 29084707-29085500 | chr10 | 29085272 | LINC00837 | TSS1500; Body |
| chr10: 29084707-29085500 | chr10 | 29085499 | LINC00837 | TSS1500; Body |
| chr10: 29084707-29085500 | chr10 | 29084858 | LINC01517 | Body |
| chr10: 29084707-29085500 | chr10 | 29084707 | LINC01517 | Body |
| chr10: 29084707-29085500 | chr10 | 29085093 | LINC00837 | TSS200; Body |
| chr10: 29084707-29085500 | chr10 | 29085038 | LINC00837 | TSS200; Body |
| chr10: 29084707-29085500 | chr10 | 29085245 | LINC00837 | TSS1500; Body |
| chr10: 29084707-29085500 | chr10 | 29085115 | LINC00837 | TSS200; Body |
| chr10: 85324700-85325063 | chr10 | 85325001 | | |
| chr10: 85324700-85325063 | chr10 | 85324700 | | |
| chr10: 85324700-85325063 | chr10 | 85324857 | | |
| chr10: 85324700-85325063 | chr10 | 85324925 | | |
| chr10: 85324700-85325063 | chr10 | 85325062 | | |
| chr10: 13771107-13771466 | chr10 | 13771427 | FRMD4A | Body |
| chr10: 13771107-13771466 | chr10 | 13771383 | FRMD4A | Body |
| chr10: 13771107-13771466 | chr10 | 13771107 | FRMD4A | Body |
| chr10: 13771107-13771466 | chr10 | 13771169 | FRMD4A | Body |
| chr10: 13771107-13771466 | chr10 | 13771465 | FRMD4A | Body |
| chr11: 92615215-92617119 | chr11 | 92616319 | FAT3 | Body |
| chr11: 92615215-92617119 | chr11 | 92615215 | FAT3 | Body |
| chr11: 92615215-92617119 | chr11 | 92616492 | FAT3 | Body |
| chr11: 92615215-92617119 | chr11 | 92616615 | FAT3 | Body |
| chr11: 92615215-92617119 | chr11 | 92616378 | FAT3 | Body |
| chr11: 92615215-92617119 | chr11 | 92615932 | FAT3 | Body |
| chr11: 92615215-92617119 | chr11 | 92615544 | FAT3 | Body |

TABLE 2-continued

Characterization of CpG sites within the Top
50 regions of hypomethylation in sperm DNA

| Region Designation | Chromosome | Location | Gene | Gene region |
|---|---|---|---|---|
| chr11: 92615215-92617119 | chr11 | 92617118 | FAT3 | Body |
| chr11: 92615215-92617119 | chr11 | 92616396 | FAT3 | Body |
| chr11: 70415188-70416310 | chr11 | 70415188 | SHANK2 | Body |
| chr11: 70415188-70416310 | chr11 | 70416309 | SHANK2 | Body |
| chr11: 70415188-70416310 | chr11 | 70415493 | SHANK2 | Body |
| chr11: 70415188-70416310 | chr11 | 70415588 | SHANK2 | Body |
| chr11: 70415188-70416310 | chr11 | 70416238 | SHANK2 | Body |
| chr11: 70415188-70416310 | chr11 | 70415439 | SHANK2 | Body |
| chr11: 70415188-70416310 | chr11 | 70415416 | SHANK2 | Body |
| chr11: 70415188-70416310 | chr11 | 70416269 | SHANK2 | Body |
| chr12: 52472758-52474048 | chr12 | 52473014 | OR7E47P | TSS1500 |
| chr12: 52472758-52474048 | chr12 | 52473731 | OR7E47P | Body |
| chr12: 52472758-52474048 | chr12 | 52473462 | OR7E47P | TSS200 |
| chr12: 52472758-52474048 | chr12 | 52472758 | OR7E47P | TSS1500 |
| chr12: 52472758-52474048 | chr12 | 52474047 | OR7E47P | Body |
| chr12: 52472758-52474048 | chr12 | 52473451 | OR7E47P | TSS200 |
| chr12: 52472758-52474048 | chr12 | 52473422 | OR7E47P | TSS200 |
| chr13: 36787282-36789909 | chr13 | 36788843 | SOHLH2 | TSS200; Body |
| chr13: 36787282-36789909 | chr13 | 36788859 | SOHLH2 | TSS200; Body |
| chr13: 36787282-36789909 | chr13 | 36787282 | SOHLH2 | Body |
| chr13: 36787282-36789909 | chr13 | 36787952 | SOHLH2 | Body |
| chr13: 36787282-36789909 | chr13 | 36789908 | SOHLH2 | TSS1500; Body |
| chr13: 36787282-36789909 | chr13 | 36788926 | SOHLH2 | TSS200; Body |
| chr13: 36787282-36789909 | chr13 | 36788776 | SOHLH2 | TSS200; Body |
| chr13: 36787282-36789909 | chr13 | 36789081 | SOHLH2 | TSS1500; Body |
| chr13: 36787282-36789909 | chr13 | 36787885 | SOHLH2 | Body |
| chr13: 36787282-36789909 | chr13 | 36789681 | SOHLH2 | TSS1500; Body |
| chr13: 36787282-36789909 | chr13 | 36789896 | SOHLH2 | TSS1500; Body |
| chr13: 36787282-36789909 | chr13 | 36788462 | SOHLH2 | Body |
| chr13: 36787282-36789909 | chr13 | 36788861 | SOHLH2 | TSS200; Body |
| chr13: 36787282-36789909 | chr13 | 36788667 | SOHLH2 | 1stExon; 5URT; Body |
| chr13: 36787282-36789909 | chr13 | 36789025 | SOHLH2 | TSS1500; Body |
| chr16: 89345548-89346492 | chr16 | 89346491 | ANKRD11 | Body |
| chr16: 89345548-89346492 | chr16 | 89346269 | ANKRD11 | Body |
| chr16: 89345548-89346492 | chr16 | 89345595 | ANKRD11 | Body |
| chr16: 89345548-89346492 | chr16 | 89346436 | ANKRD11 | Body |
| chr16: 89345548-89346492 | chr16 | 89345548 | ANKRD11 | Body |

TABLE 2-continued

Characterization of CpG sites within the Top 50 regions of hypomethylation in sperm DNA

| Region Designation | Chromosome | Location | Gene | Gene region |
|---|---|---|---|---|
| chr16: 90172237-90173535 | chr16 | 90172237 | FAM157C | Body |
| chr16: 90172237-90173535 | chr16 | 90172816 | FAM157C | Body |
| chr16: 90172237-90173535 | chr16 | 90173019 | FAM157C | Body |
| chr16: 90172237-90173535 | chr16 | 90172742 | FAM157C | Body |
| chr16: 90172237-90173535 | chr16 | 90173534 | FAM157C | Body |
| chr16: 90172237-90173535 | chr16 | 90172731 | FAM157C | Body |
| chr17: 43318045-43319383 | chr17 | 43318735 | FMNL1 | ExonBnd; Body |
| chr17: 43318045-43319383 | chr17 | 43319137 | FMNL1 | Body |
| chr17: 43318045-43319383 | chr17 | 43318045 | FMNL1 | Body |
| chr17: 43318045-43319383 | chr17 | 43318610 | FMNL1 | ExonBnd; Body |
| chr17: 43318045-43319383 | chr17 | 43319382 | FMNL1 | Body |
| chr17: 43318045-43319383 | chr17 | 43319371 | FMNL1 | Body |
| chr17: 43318045-43319383 | chr17 | 43318760 | FMNL1 | ExonBnd; Body |
| chr17: 74302589-74304620 | chr17 | 74303798 | QRICH2 | TSS200 |
| chr17: 74302589-74304620 | chr17 | 74303935 | QRICH2 | TSS200 |
| chr17: 74302589-74304620 | chr17 | 74303724 | QRICH2 | 1stExon; 5URT; Body |
| chr17: 74302589-74304620 | chr17 | 74304007 | QRICH2 | TSS1500 |
| chr17: 74302589-74304620 | chr17 | 74304204 | QRICH2 | TSS1500 |
| chr17: 74302589-74304620 | chr17 | 74303886 | QRICH2 | TSS200 |
| chr17: 74302589-74304620 | chr17 | 74304619 | QRICH2 | TSS1500 |
| chr17: 74302589-74304620 | chr17 | 74303956 | QRICH2 | TSS200 |
| chr17: 74302589-74304620 | chr17 | 74304023 | QRICH2 | TSS1500 |
| chr17: 74302589-74304620 | chr17 | 74304010 | QRICH2 | TSS1500 |
| chr17: 74302589-74304620 | chr17 | 74303439 | QRICH2 | Body |
| chr17: 74302589-74304620 | chr17 | 74302589 | QRICH2 | Body |
| chr17: 7909776-7910041 | chr17 | 7910040 | GUCY2D | ExonBnd; Body |
| chr17: 7909776-7910041 | chr17 | 7909845 | GUCY2D | Body |
| chr17: 7909776-7910041 | chr17 | 7909983 | GUCY2D | Body |
| chr17: 7909776-7910041 | chr17 | 7909776 | GUCY2D | Body |
| chr19: 2926081-2927446 | chr19 | 2927445 | | |
| chr19: 2926081-2927446 | chr19 | 2926882 | | |
| chr19: 2926081-2927446 | chr19 | 2926081 | | |
| chr19: 2926081-2927446 | chr19 | 2926196 | | |
| chr19: 2926081-2927446 | chr19 | 2927396 | | |
| chr19: 2926081-2927446 | chr19 | 2926894 | | |
| chr19: 10463037-10465258 | chr19 | 10464771 | TYK2 | Body |
| chr19: 10463037-10465258 | chr19 | 10463037 | TYK2 | Body |

TABLE 2-continued

Characterization of CpG sites within the Top
50 regions of hypomethylation in sperm DNA

| Region Designation | Chromosome | Location | Gene | Gene region |
|---|---|---|---|---|
| chr19: 10463037-10465258 | chr19 | 10464100 | TYK2 | Body |
| chr19: 10463037-10465258 | chr19 | 10463828 | TYK2 | Body |
| chr19: 10463037-10465258 | chr19 | 10465257 | TYK2 | Body |
| chr19: 10463037-10465258 | chr19 | 10464711 | TYK2 | ExonBnd; Body |
| chr19: 10463037-10465258 | chr19 | 10463352 | TYK2 | Body |
| chr19: 10463037-10465258 | chr19 | 10464842 | TYK2 | Body |
| chr19: 10463037-10465258 | chr19 | 10464320 | TYK2 | ExonBnd; Body |
| chr19: 10463037-10465258 | chr19 | 10464767 | TYK2 | Body |
| chr19: 10463037-10465258 | chr19 | 10463831 | TYK2 | Body |
| chr19: 10463037-10465258 | chr19 | 10464922 | TYK2 | ExonBnd; Body |
| chr19: 10463037-10465258 | chr19 | 10463879 | TYK2 | Body |
| chr19: 36612371-36612912 | chr19 | 36612722 | TBCB | Body |
| chr19: 36612371-36612912 | chr19 | 36612741 | TBCB | Body |
| chr19: 36612371-36612912 | chr19 | 36612911 | TBCB | Body |
| chr19: 36612371-36612912 | chr19 | 36612371 | TBCB | Body |
| chr19: 36612371-36612912 | chr19 | 36612631 | TBCB | Body; ExonBnd |
| chr19: 50058328-50060307 | chr19 | 50059946 | NOSIP | Body |
| chr19: 50058328-50060307 | chr19 | 50060306 | NOSIP | Body |
| chr19: 50058328-50060307 | chr19 | 50058499 | | |
| chr19: 50058328-50060307 | chr19 | 50059750 | NOSIP | Body |
| chr19: 50058328-50060307 | chr19 | 50058971 | NOSIP | 3UTR |
| chr19: 50058328-50060307 | chr19 | 50059027 | NOSIP | Body |
| chr19: 50058328-50060307 | chr19 | 50059164 | NOSIP | Body |
| chr19: 50058328-50060307 | chr19 | 50058328 | | |
| chr19: 50058328-50060307 | chr19 | 50059937 | NOSIP | Body |
| chr19: 50058328-50060307 | chr19 | 50060174 | NOSIP | Body |
| chr20: 55684764-55685923 | chr20 | 55685778 | | |
| chr20: 55684764-55685923 | chr20 | 55684764 | | |
| chr20: 55684764-55685923 | chr20 | 55685922 | | |
| chr20: 55684764-55685923 | chr20 | 55685638 | | |
| chr20: 55684764-55685923 | chr20 | 55685277 | | |
| chr22: 32749516-32750882 | chr22 | 32750845 | RFPL3 | TSS200 |
| chr22: 32749516-32750882 | chr22 | 32749516 | RFPL3 | TSS1500 |
| chr22: 32749516-32750882 | chr22 | 32750744 | RFPL3 | TSS200 |
| chr22: 32749516-32750882 | chr22 | 32749962 | RFPL3 | TSS1500 |
| chr22: 32749516-32750882 | chr22 | 32750423 | RFPL3 | TSS1500 |
| chr22: 32749516-32750882 | chr22 | 32750777 | RFPL3 | TSS200 |

TABLE 2-continued

Characterization of CpG sites within the Top
50 regions of hypomethylation in sperm DNA

| Region Designation | Chromosome | Location | Gene | Gene region |
|---|---|---|---|---|
| chr22: 32749516-32750882 | chr22 | 32750734 | RFPL3 | TSS200 |
| chr22: 32749516-32750882 | chr22 | 32750881 | RFPL3 | 1stExon; 5URT |
| chr22: 32749516-32750882 | chr22 | 32750782 | RFPL3 | TSS200 |
| chr22: 32749516-32750882 | chr22 | 32749800 | RFPL3 | TSS1500 |
| chr22: 50008841-50010192 | chr22 | 50008841 | C22orf34 | Body |
| chr22: 50008841-50010192 | chr22 | 50009156 | C22orf34 | Body |
| chr22: 50008841-50010192 | chr22 | 50009422 | C22orf34 | Body |
| chr22: 50008841-50010192 | chr22 | 50009865 | C22orf34 | Body |
| chr22: 50008841-50010192 | chr22 | 50010191 | C22orf34 | Body |
| chr22: 50008841-50010192 | chr22 | 50009424 | C22orf34 | Body |
| chr22: 50008841-50010192 | chr22 | 50009551 | C22orf34 | Body |
| chrX: 40481859-40483213 | chrX | 40482023 | MPC1L | TSS1500 |
| chrX: 40481859-40483213 | chrX | 40481859 | MPC1L | TSS1500 |
| chrX: 40481859-40483213 | chrX | 40482442 | MPCIL | TSS1500 |
| chrX: 40481859-40483213 | chrX | 40482174 | MPCIL | TSS1500 |
| chrX: 40481859-40483213 | chrX | 40482072 | MPC1L | TSS1500 |
| chrX: 40481859-40483213 | chrX | 40483212 | MPC1L | 1stExon |
| chrX: 40481859-40483213 | chrX | 40482623 | MPCIL | TSS200 |
| chrX: 40481859-40483213 | chrX | 40482799 | MPC1L | TSS200 |
| chrX: 40481859-40483213 | chrX | 40482639 | MPCIL | TSS200 |
| chrX: 40481859-40483213 | chrX | 40482769 | MPCIL | TSS200 |
| chrX: 31089692-31090940 | chrX | 31090306 | FTHL 17 | TSS200 |
| chrX: 31089692-31090940 | chrX | 31089887 | FTHL17 | 1stExon |
| chrX: 31089692-31090940 | chrX | 31090380 | FTHL17 | TSS1500 |
| chrX: 31089692-31090940 | chrX | 31090329 | FTHL17 | TSS200 |
| chrX: 31089692-31090940 | chrX | 31089692 | FTHL17 | 1stExon |
| chrX: 31089692-31090940 | chrX | 31090793 | FTHL17 | TSS1500 |
| chrX: 31089692-31090940 | chrX | 31090939 | FTHL 17 | TSS1500 |
| chrX: 31089692-31090940 | chrX | 31090318 | FTHL17 | TSS200 |
| chrX: 31089692-31090940 | chrX | 31090073 | FTHL17 | 1stExon; 5URT |
| chrX: 31089692-31090940 | chrX | 31090374 | FTHL17 | TSS1500 |
| chrX: 31089692-31090940 | chrX | 31090296 | FTHL17 | TSS200 |
| chrX: 31089692-31090940 | chrX | 31090309 | FTHL17 | TSS200 |
| chrX: 129471948-129472963 | chrX | 129472061 | | |
| chrX: 129471948-129472963 | chrX | 129471948 | | |
| chrX: 129471948-129472963 | chrX | 129472572 | SLC25A14 | TSS1500 |

TABLE 2-continued

Characterization of CpG sites within the Top 50 regions of hypomethylation in sperm DNA

| Region Designation | Chromosome | Location | Gene | Gene region |
|---|---|---|---|---|
| chrX: 129471948-129472963 | chrX | 129472962 | SLC25A14 | TSS1500 |
| chrX: 129471948-129472963 | chrX | 129472580 | SLC25A14 | TSS1500 |
| chrX: 134974589-134976103 | chrX | 134975148 | SAGE1 | TSS1500; 5URT |
| chrX: 134974589-134976103 | chrX | 134975547 | SAGE1 | TSS1500; 1stExon; 5URT |
| chrX: 134974589-134976103 | chrX | 134975883 | CT45A10 | TSS1500; 1stExon; 5URT |
| chrX: 134974589-134976103 | chrX | 134974865 | SAGE1 | TSS1500;5URT |
| chrX: 134974589-134976103 | chrX | 134976100 | CT45A10 | TSS1500; 5URT |
| chrX: 134974589-134976103 | chrX | 134975582 | SAGE1 | TSS1500; TSS200 |
| chrX: 134974589-134976103 | chrX | 134976102 | CT45A10 | TSS1500; 5URT |
| chrX: 134974589-134976103 | chrX | 134975643 | CT45A10 | TSS200 |
| chrX: 134974589-134976103 | chrX | 134975712 | CT45A10 | TSS200 |
| chrX: 134974589-134976103 | chrX | 134974589 | SAGE1 | TSS1500; 5URT |
| chrX: 42636927-42638572 | chrX | 42638571 | PPP1R2P9 | TSS1500 |
| chrX: 42636927-42638572 | chrX | 42637584 | PPP1R2P9 | TSS200 |
| chrX: 42636927-42638572 | chrX | 42637578 | PPP1R2P9 | TSS200 |
| chrX: 42636927-42638572 | chrX | 42637044 | PPP1R2P9 | Body |
| chrX: 42636927-42638572 | chrX | 42636927 | PPP1R2P9 | Body |
| chrX: 42636927-42638572 | chrX | 42638108 | PPP1R2P9 | TSS1500 |
| chrX: 2636927-42638572 | chrX | 42637548 | PPP1R2P9 | TSS200 |
| chrX: 42636927-42638572 | chrX | 42637305 | PPP1R2P9 | Body |
| chrX: 42636927-42638572 | chrX | 42637497 | PPP1R2P9 | TSS200 |
| chrX: 42636927-42638572 | chrX | 42637506 | PPP1R2P9 | TSS200 |

In some embodiments, the presence of methylation is identified in at least: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 regions of the extracted DNA or the extracted cell free DNA from Table 1. In some cases, as used herein, a region can correspond to a region indicated by the location provided in the region designation column (e.g. see Table 1). In some cases, the presence of methylation may not comprise a complete methylation of a region but an increase in methylation as compared to a control. In some embodiments, the absence of methylation is identified in at least: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 regions of the extracted DNA or the extracted cell free DNA from Table 1. In some cases, the absence of methylation can comprise a complete absence in methylation of a region. In some cases, the absence of methylation may not comprise a complete absence in methylation of a region but a reduction in methylation as compared to a control. For example 100% of the sites in a region are methylated in a somatic cell sample and 50% of the sites in a region are methylated in a sperm cell sample. In some embodiments, a methylation pattern comprises at least: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 regions of the extracted DNA or the extracted cell free DNA from Table 1. In some cases, a methylation pattern comprises the presence of methylation, the absence or methylation, or a combination thereof in one or more regions of Table 1. In some cases, the methylation pattern of: at least one, at least two, at least three, at least four, at least five, at least six, at least seven, at least eight, at least nine, at least ten, at least eleven, at least twelve, or more regions of Table 1 can be employed to determine the presence of a sperm cell in a sample. In some cases, any region or any combination of regions of Table 1 can be employed to determine the presence of a sperm cell in a sample. In some cases, the absence of methylation in at least one, at least two, at least three, at least four, at least five, at least six, at least seven, at least eight, at least nine, at least ten, at least eleven, at least twelve, or more regions of Table 1 can be employed to determine the presence of a sperm cell in a sample.

In some embodiments, the presence or absence of methylation is identified in at least: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 regions of the extracted DNA or the extracted cell free DNA to identify a sperm cell in a sample. In some embodiments, a region can comprise chr1: 182921660-182923994 (chr1 (Chromosome 1) location: 182921660-182923994 bp on chromosome 1). In some embodiments, a region can comprise chr1:18807594-18809765. In some embodiments, a region can comprise chr1:190067323-190068181. In some embodiments, a region can comprise chr1:247681102-247681932. In some embodiments, a region can comprise chr1:35441734-35443497. In some embodiments, a region can comprise chr1:9130738-9132197. In some embodiments, a region can comprise chr1:92682167-92683822. In some embodiments, a region can comprise chr10:13771107-13771466. In some embodiments, a region can comprise chr10:29084707-29085500. In some embodiments, a region can comprise chr10:85324700-85325063. In some embodiments, a region can comprise chr11:70415188-70416310. In some embodiments, a region can comprise chr11:92615215-92617119. In some embodiments, a region can comprise chr12:52472758-52474048. In some embodiments, a region can comprise chr13:36787282-36789909. In some embodiments, a region can comprise chr16:89345548-89346492. In some embodiments, a region can comprise chr16:90172237-90173535. In some embodiments, a region can comprise chr17:43318045-43319383. In some embodiments, a region can comprise chr17:74302589-74304620. In some embodiments, a region can comprise chr17:7909776-7910041. In some embodiments, a region can comprise chr19:10463037-10465258. In some embodiments, a region can comprise chr19:2926081-2927446. In some embodiments, a region can comprise chr19:36612371-36612912. In some embodiments, a region can comprise chr19:50058328-50060307. In some embodiments, a region can comprise chr2:128158047-128159059. In some embodiments, a region can comprise chr20: 55684764-55685923. In some embodiments, a region can comprise chr22:32749516-32750882. In some embodiments, a region can comprise chr22:50008841-50010192. In some embodiments, a region can comprise chr3:77145918-77148085. In some embodiments, a region can comprise chr3:9027157-9027577. In some embodiments, a region can comprise chr4:128650393-128652120. In some embodiments, a region can comprise chr4:151500192-151505193. In some embodiments, a region can comprise chr4: 189580331-189580876. In some embodiments, a region can comprise chr4:190731443-190732882. In some embodiments, a region can comprise chr5:121186479-121188229. In some embodiments, a region can comprise chr5:5057256-5057720. In some embodiments, a region can comprise chr7:5540163-5541567. In some embodiments, a region can comprise chr7:5645728-5648123. In some embodiments, a region can comprise chr7:64330493-64331111. In some embodiments, a region can comprise chr7:6524925-6525026. In some embodiments, a region can comprise chr7:6865886-6867075. In some embodiments, a region can comprise chr7:72741781-72743404. In some embodiments, a region can comprise chr7:75023589-75024730. In some embodiments, a region can comprise chr8:109143682-109144231. In some embodiments, a region can comprise chr9:138590204-138594308. In some embodiments, a region can comprise chr9:72129977-72131656. In some embodiments, a region can comprise chrX:129471948-129472963. In some embodiments, a region can comprise chrX:134974589-134976103. In some embodiments, a region can comprise chrX:31089692-31090940. In some embodiments, a region can comprise chrX:40481859-40483213. In some embodiments, a region can comprise chrX:42636927-42638572.

In some embodiments, at least about: 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the methylation sites of a specific region of Table 2 are methylated. In some cases, at least about 50% or at least about 75% of the plurality of methylated sites are methylated. In some cases, one or more of the methylation sites of a specific region of Table 2 is methylated. In some cases, two, three, four, five, six, or more of the methylation sites of a specific region of Table 2 are methylated. In some cases, all of the methylation sites of a specific region of Table 2 are methylated. In some cases, about: 10% to 100%, 10% to 40%, 20% to 60%, 30% to 70%, 40% to 80%, 50% to 95%, 60% to 85%, 70% to 95% or 80% to 100% of the methylation sites of a specific region of Table 2 are methylated. In some cases, the presence of methylation in 50% to 100% of the sites (Table 2) comprised in one or more regions can indicate the presence of a somatic cell in a sample.

In some embodiments, less than about: 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the methylation sites of a specific region of Table 2 are methylated. In some embodiments, more than about: 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the methylation sites of a specific region of Table 2 are unmethylated. In some cases, all of the methylation sites of a specific region of Table 2 are unmethylated. In some cases, less than about 75% of the plurality of methylated sites are methylated. In some cases, more than about 75% of the plurality of methylated sites are unmethylated. In some cases, about: 10% to 100%, 10% to 40%, 20% to 60%, 30% to 70%, 40% to 80%, 50% to 95%, 60% to 85%, 70% to 95% or 80% to 100% of the methylation sites of a specific region of Table 2 are not methylated. In some cases, the absence of methylation on 50% to 100% of the sites (Table 2) comprised in one or more regions can indicate the presence of a sperm cell in a sample. In some cases, the absence of methylation on about: 30% to 100%, 40% to about 90%, 50% to about 80%, 60% to about 100%, 70% to about 100%, 80% to about 100% or 90% to about 100% of the sites (Table 2) comprised in one or more regions can indicate the presence of a sperm cell in a sample.

In some cases, the presence of methylation is identified in at least: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more genes or regions associated with a gene (e.g., a TSS200, a TSS1500, a SUTR, a 3UTR, a gene body, an exon, or any region associated with a gene) of the extracted DNA or the extracted cell free DNA from Table 2. In some embodiments, the absence of methylation is identified in at least: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more genes or regions associated with a gene of the extracted DNA or the extracted cell free DNA from Table 2. In some embodiments, a methylation pattern comprises at least: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more genes or regions associated with a gene of the extracted DNA or the extracted cell free DNA from Table 2. In some cases, the methylation pattern of: at least one, at least two, at least three, at least four, at least five, at least six, at least seven, at least eight, at least nine, at least ten, at least eleven, at least twelve, or more genes or regions associated with a gene of Table 2 can be employed to determine the presence of a sperm cell in a sample. In some cases, any gene or any region associated with a gene of Table 2 can be employed to determine the presence of a sperm cell in a sample.

TABLE 3

Genbank Assembly Information for HG19 (GRCh37)

| Description | Genome Reference Consortium Human Build 37 (GRCh37) also known as HG19 |
|---|---|
| Organism name | Homo sapiens (human) |
| BioProject Number | PRJNA31257 |
| Submitter | Genome Reference Consortium |
| Date | 2/27/2009 |
| GenBank assembly accession | GCA_000001405.1 |
| RefSeq assembly accession | GCF_000001405.13 |

In some embodiments, a method herein can comprise a) obtaining a biological sample from a subject; b) extracting DNA from a prostate cell in the biological sample or extracting cell free DNA from the biological sample; and c) detecting a presence or an absence of a methylation pattern of a region of the extracted DNA or the extracted cell free DNA from the biological sample. In some cases, the methylation pattern comprises a hypermethylation or a hypomethylation of at least one region of a chromosome. In some cases, the method can comprise comparing the methylation pattern of the at least one region of the extracted DNA or the extracted cell free DNA from the biological sample to a control pattern of DNA methylation. In some cases, the at least one region of the chromosome comprises: (i) a promoter of: ZFP64, MOB3B, or HLF; (ii) a gene comprising: TCAF-1, CHST-11, or ALOX-5, or (iii) any combination of (i) and (ii). In some cases, the biological sample comprises seminal fluid. In some embodiments, the method can be a method of detecting a cancerous prostate cell. In some cases, the method further comprises determining the presence or absence of the cancerous prostate cell in the biological sample from the subject. In some instances, the presence or absence of the methylation pattern indicates the presence or absence of the cancerous prostate cell in the biological sample. In some cases, a control pattern can comprise a cancerous prostate cell methylation pattern. In some cases, a control pattern can comprise a noncancerous prostate cell methylation pattern.

In some embodiments, the methods herein comprise the steps of detecting, comparing, determining, or any combination thereof. In some cases, the detecting can comprise executing a computer program on a computer. In some cases, the comparing can comprise executing a computer program on a computer. In some cases, the determining can comprise executing a computer program on a computer. In some embodiments, the detecting, the comparing, the determining, or any combination thereof employs a computer processor. In some cases, the determining employs a computer processor for receiving and analyzing data comprising the presence or absence of the methylation pattern. In some cases, a computer program can be the same computer program. In some cases, a computer program can be a different computer program. For example, the detecting and comparing steps can use the same or different computer programs.

Figure 6:
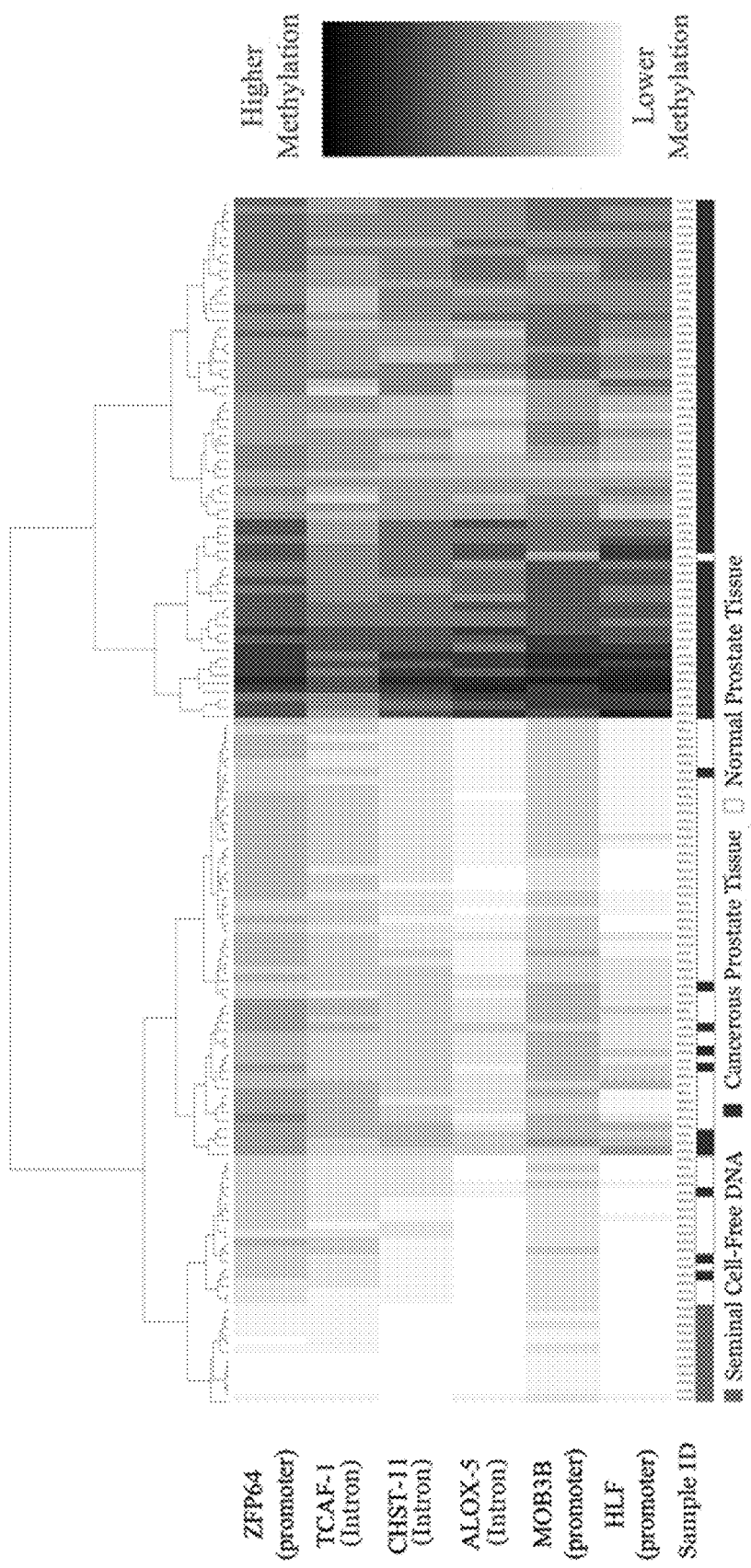
FIG. 6 shows a methylation pattern heatmap of cell free DNA from seminal fluid, cancerous prostate tissue, and normal prostate tissue for the following regions: ZFP64 (promoter), TCAF-1 (intron), CHST-11 (intron) ALOX-5 (intron), MOB3B (promoter), and HLF (promoter).

In some cases, the method disclosed herein are methods of detecting a cancerous prostate cell. Table 4 shows the hypermethylated regions of specific genes ("Hypermethylated region") associated with cancerous prostate cells and the specific location ("Location of Hypermethylation") of the hypermethylation. The chromosome (e.g. Chr20 is Chromosome 20) and chromosomal coordinates of the region is shown in the "Region Designation" column. The region designation is in reference to the reference genome is HG19 (GenBank assembly accession: GCA_000001405.1). The National Center for Biotechnology Information (NCBI) description for the genome is provided in Table 3. The number of CpG sites screened in the region is shown in the column "CpG sites". The log 2 ratio and Phred scaled FDR values are shown for the comparison of cancerous prostate tissue as compared to noncancerous prostate tissue. In some cases, a methylation pattern can comprise hypermethylation or hypomethylation of 1, 2, 3, 4, 5, or 6 regions of Table 4. In some cases, the methylation pattern can comprise a mix of hypermethylation and hypomethylated regions of Table 4. A cancerous prostate cell can have hypermethylation at 1, 2, 3, 4, 5, or 6 regions of Table 4 as compared to a noncancerous prostate cell. In some cases, a noncancerous prostate cell can have hypomethylation at 1, 2, 3, 4, 5, or 6 regions of Table 4 as compared to a cancerous prostate cell. In some cases, a noncancerous prostate cell can have hypomethylation at all 6 regions of Table 4 as compared to a cancerous prostate cell. In some cases, a hypermethylated region (e.g., a promoter of, an intron of, an exon of, or any region associated with the gene) can comprise ZFP64, MOB3B, HLF, TCAF-1, CHST-11, or ALOX-5. In some cases, the hypermethylation region of ZFP64, MOB3B, and HLF is the promoter region. In some cases, the hypermethylation region of TCAF-1, CHST-11, and ALOX-5 is the intron region. In some cases, a noncancerous prostate cell can have hypomethylation at ZFP64, MOB3B, HLF, TCAF-1, CHST-11, ALOX-5, or any combination thereof as compared to a cancerous prostate cell. In some cases, a cancerous prostate cell can have hypermethylation at ZFP64, MOB3B, HLF, TCAF-1, CHST-11, ALOX-5, or any combination thereof as compared to a noncancerous prostate cell. In some cases, detecting a prostate cancer in a subject can comprise detecting the hypermethylation of: at least one, at least two, at least three, at least four, or at least five of the hypermethylated regions in Table 4. In some cases, detecting a prostate cancer in a subject can comprise detecting the hypermethylation of all six hypermethylated regions in Table 4. In some cases, the methylation pattern (e.g., hypermethylation and/or hypomethylation) of: at least one, at least two, at least three, at least four, at least five, or at least six, regions of Table 4 can be employed to determine the presence of a cancerous prostate cell a sample. In some cases, the methylation pattern (e.g., hypermethylation and/or hypomethylation) of any one of the regions of Table 4 can be employed to determine the presence of a cancerous prostate cell a sample. In some cases, detecting a prostate cancer in a subject can comprise identifying the hypermethylated regions in cfDNA from seminal sample of a subject. In some cases, the regions of Table 4 are hypermethylated in a cancerous prostate cell as compared to a noncancerous cell. FIG. 6 shows the hypermethylation of regions described in Table 4 are associated with cancerous samples which cluster mostly to the right of the heatmap.

In some cases, detecting a noncancerous prostate cell in a subject can comprise identifying the hypomethylated regions in a biological sample of a subject. In some cases, a biological sample can be a semen sample and the hypomethylated regions can be identified in cfDNA. In some cases, detecting a noncancerous prostate cell in a subject can comprise detecting the hypomethylation of: at least one, at least two, at least three, at least four, or at least five of the hypermethylated regions in Table 4. In some cases, detecting a noncancerous prostate cell (e.g., cell free DNA from a noncancerous prostate cell) in a subject can comprise detecting the hypomethylation of any one of the hypermethylated regions in Table 4. In some cases, detecting a noncancerous prostate cell in a subject can comprise detecting the hypomethylation of all six hypermethylated regions in Table 4.

In some cases, one, two, three, four, five, or six of the CpG sites of a region of Table 4 are methylated. In some cases, all the CpG sites of a region Table 4 are methylated. In some cases hypermethylation of a region can comprise all of the CpG sites of a region of Table 4 being methylated. In some cases hypermethylation of a region can comprise one, two, three, four, five, or six of the CpG sites of a region of Table 4 being methylated. In some cases, one, two, three, four, five, or six of the CpG sites of a region of Table 4 are unmethylated. In some cases, all the CpG sites of a region Table 4 are unmethylated.

In some embodiments, a method herein comprises comparing a DNA methylation pattern of a biological sample to a control pattern of DNA methylation. In some cases, a control pattern of DNA methylation can be a reference sample. In some cases, a control pattern of DNA methylation can be associated with a cell type. In some cases, a cell type can be a sperm cell. In some cases, a cell type can be a prostate cell. In some cases, a cell type can be a cancerous prostate cell.

Also disclosed herein are methods of predicting a treatment response in a human subject having or suspected of having a disease. In some cases, the disease can comprise azoospermia (e.g., non-obstructive azoospermia). In some cases, the disease can be prostate cancer. In some cases, the method of predicting a treatment response can comprise obtaining a biological sample from the human subject and extracting DNA or cell free DNA from the biological sample. In some cases, the biological sample is seminal fluid. In some cases, the method of predicting a treatment response can comprise detecting a presence or an absence of a sperm cell from the DNA or the cell free DNA by determining a methylation pattern of a region of the DNA or the cell free DNA. In some cases, the methylation pattern comprises the presence or the absence of methylation of at least one region of DNA from Table 1. In some cases, the methylation pattern comprises the presence or the absence of methylation of at least one region of DNA from Table 4. In some cases, the method of predicting a treatment response can comprise comparing the methylation pattern of the region of the DNA or the cell free DNA to a control pattern of DNA methylation associated with a sperm cell. In some cases, the method of predicting a treatment response can comprise comparing the methylation pattern of the region of the DNA or the cell free DNA to a control pattern of DNA methylation associated with a cancerous prostate cell.

In some cases, the method of predicting a treatment response can comprise determining the presence or the absence of the methylation pattern of the region of the DNA or the cell free DNA from the seminal fluid sample, thereby determining the presence of the sperm cell from the seminal fluid sample; wherein the presence of the sperm cell indicates that the human subject has a greater likelihood of benefiting from a therapy to treat azoospermia and wherein the absence of the sperm cell indicates that the human subject has a decreased likelihood of benefiting from the therapy. For example, the method can inform a healthcare

TABLE 4

Hypermethylation regions of cancerous prostate cells

| Hypermethylated Region | Location of Hypermethylation | Region Designation | CpG Sites | Log2 Ratio | Phred Scaled FDR |
|---|---|---|---|---|---|
| ZFP64 | Promoter | Chr20 50719777-50723228 | 6 | 2.11 | 82.07 |
| TCAF-1 | Intron | Chr7 143579665-143580148 | 1 | 2.14 | 82.07 |
| CHST11 | Intron | Chr12 104852047-104853101 | 2 | 2.07 | 82.07 |
| ALOX5 | Intron | Chr10 45914276-45914950 | 1 | 2.06 | 82.07 |
| MOB3B | Promoter | Chr9 27528300-27530603 | 4 | 2.13 | 82.07 |
| HLF | Promoter | Chr17 53341098-53343562 | 4 | 2.07 | 82.07 | provider if the subject has sperm at some location in the reproductive tract. If the sperm is present, the subject has a greater likelihood from benefiting from a therapy as compared to a subject who does not have detectable sperm in the reproductive tract.

In some cases, the method of predicting a treatment response can comprise determining the presence or the absence of the methylation pattern of the region of the DNA or the cell free DNA from the seminal fluid sample, thereby determining the presence of the cancerous prostate cell from the seminal fluid sample. In some cases, the presence of the cancerous prostate cell indicates that the human subject has a greater likelihood of benefiting from a therapy to treat prostate cancer and wherein the absence of the cancerous prostate cell indicates that the human subject has a decreased likelihood of benefiting from the therapy.

In some embodiments, likelihood can relate to an individual assessment of any parameter that can be useful in determining the evolution of a subject. In some cases, the likelihood of the clinical response to a treatment although preferred to be, need not be correct for 100% of the subjects to be diagnosed or evaluated. In some cases, likelihood can require that a statistically significant portion of subjects be identified as having an increased probability of having a positive/negative response. In some cases, likelihood can be correlative to a positive/negative response.

An epigenetic modification can be identified by an assay designed to identify a methylated base. In some cases, an assay can comprise sodium bisulfite conversion, a sequencing, a differential enzymatic cleavage of DNA, an affinity capture of methylated DNA, an array, or any combination thereof. In some cases, an assay can comprise an array assay, such as a microarray. In some cases, an assay can be a polymerase chain reaction (PCR). In some cases, a PCR can be a droplet digital PCR (ddPCR), a quantitative real time PCR (qRT PCT), or reverse transcriptase PCR. In some instances, a sequencing can comprise Sanger sequencing, sequencing by synthesis, a sequencing by hybridization, a 454 pyrosequencing, an ion torrent sequencing, a short read sequencing, a long read sequencing, a single molecule real time sequencing, a single cell sequencing method, a nanopore sequencing, or any combination thereof. In some cases, a restriction enzyme based differential cleavage of methylated DNA can be locus-specific. In some cases, affinity-capture and/or bisulphite conversion followed by sequencing methods can be used for both region specific or genome-wide analysis of methylation. In some cases, a sequencing method (e.g., single molecule real time sequencing) can be used for both gene specific or genome-wide analysis of methylation. In some cases, a DNA affinity capture method can be methylated DNA immunoprecipitation (Me-DIP). In some instances, Me-DIP can use a methyl DNA specific antibody, or methyl capture using methyl-CpG binding domain (MBD) proteins. In some cases, affinity-capture and/or bisulphite conversion can be followed by an hybridization to an array. In some cases, In some cases, affinity-capture and/or bisulphite conversion can be followed by a PCR. In some cases, a PCR of bisulphite converted DNA can be sequenced by Sanger sequencing to identify a methylated region. In some instances, an assay be designed to identify methylation at one region, more than one region (e.g., 1, 5, 10, 25, or 50 regions) or the be designed to be genome wide. In some cases, an assay can comprise differential enzymatic cleavage of DNA, PCR amplification of the region of interest, and sequencing. In some cases, an assay can comprise converting unmethylated cytosines to uracils (e.g., bisulfite conversion) in at least a portion of the extracted DNA to form converted DNA and sequencing the converted DNA.

Forensic Analysis

In some embodiments, a method herein can comprise a forensic analysis method of identifying a gamete cell from an article. In some cases, the method can comprise extracting DNA or cell free DNA from the article. In some cases, the method can comprise detecting a presence or an absence of a methylation pattern of a region of the DNA or the cell free DNA. In some cases, the methylation pattern comprises the presence or the absence of methylation of at least one region of DNA or the cell free DNA from Table 1. In some cases, the method can comprise comparing the methylation pattern of the region of DNA from the article to a control pattern of methylated DNA associated with a gamete cell. In some cases, the method can comprise determining the presence or absence of the gamete cell in the article, wherein the presence or absence of the methylation pattern indicates the presence or absence of the gamete cell in the article, which is a method for forensic analysis. In some cases, the article comprises an article of evidence. In some cases, the gamete cell can be a sperm cell.

In some cases, an article of evidence can comprise a piece of matter from a crime scene. For example, an article of evidence can comprise a piece of material such as a clothing, a bed sheet, a weapon, a tool, or any material identified at a crime scene. In some cases, an article of evidence can be obtained from a sexual assault forensic exam. In some cases, an article of evidence can be a biological sample from a subject. In some cases, a subject can be a victim. For example, an article of evidence can be a sample obtained from a sexual assault victim, such as a vaginal sample, a hair sample, a blood sample, a saliva sample, or a combination thereof.

Primers and Probes

Also disclosed herein are primers, probes, or combinations thereof for detecting DNA methylation in the chromosomal regions disclosed herein (e.g., regions disclosed in Tables 1-3). In some cases, a primer can comprise a pair of primers. The primers and probes can be used to detect DNA methylation at specific sites. For example, the primers and probes herein can be used to detect DNA methylation at the sites disclosed in Table 2, or associated with the following regions: ZFP64, MOB3B, HLF, TCAF-1, CHST-11, or ALOX-5. In some cases, the primers and probes are used in a PCR assay to detect methylation at specific sites. In some instances, the DNA is converted by sodium bisulfite conversion prior to the PCR assay to identify the methylated CpG sites. In some cases, a kit or a diagnostic reagent can comprise a primer, a probe, or both a primer and a probe. In some cases, a kit or a diagnostic reagent can comprise an array. In some cases, a primer, a probe, an array, or any combination thereof can be used for the manufacture of a diagnostic reagent or kit for determining the methylation pattern of a region of DNA. In some instances an array assay can be used for the manufacture of a diagnostic reagent or kit for determining a methylation pattern of a region of DNA.

Primer sequences that can be used to detect methylation in a region of Table 4 (ZFP64, TCAF-1, CHST11, ALOX5, MOB3B, HLF) are shown in Table 6. In some cases, the primer sequences are in the 5' to 3' direction. In some cases, the primer sequence are in the 3' to 5' direction. The hypermethylated region and region coordinates (chromosome and chromosomal location) along with the primer sequences and the size of the amplicon are shown in Table 6. In some cases, the primer sequences can be used with a detection method described herein, such as a sequencing, a PCR, an array, a bisulfite conversion, or any combination thereof. In some cases, a primer sequence can comprise a sequence with at least about: 70%, 80%, 85%, 90%, 95%, 98%, or 99% sequence identity to any one of SEQ ID NOs: 1-12. In some cases, a primer sequence can comprise 100% sequence identity to any one of SEQ ID NOs: 1-12. In some cases, a primer sequence can comprise a sequence with at least about: 30%, 40%, 50%, 60%, 70%, 80%, 85%, 90%, 95%, 98%, or 99% sequence length to any one of SEQ ID NOs: 1-12.

TABLE 6

Primers for Detecting Hypermethylation of Regions in Cancerous Prostate Cells

| Hypermethylated Region | Region Designation | Forward Primer | Reverse Primer | Length of amplicon |
|---|---|---|---|---|
| ZFP64 | Chr20 50719777-50723228 | TTGGTTTGGAGTTAAGATTTTAGGA (SEQ ID NO: 1) | CCAAACCCACTAAAT CAAAATCTAC (SEQ ID NO: 2) | 322 |
| TCAF-1 | Chr7 143579665-143580148 | GGTTTTTGGAGAGG GTTATTTATTAG (SEQ ID NO: 3) | TAAACCACAACAATA CCAAACCAC (SEQ ID NO: 4) | 307 |
| CHST11 | Chr12 104852047-104853101 | TTTTTGTGGTTTAG GTAAAGTTTTA (SEQ ID NO: 5) | CTTACAATTAAAAAA ACAAATTATTACTAT (SEQ ID NO: 6) | 350 |
| ALOX5 | Chr10 45914276-45914950 | GTTTAGGGATAAAT TGGGAGT (SEQ ID NO: 7) | ACCCCCTAAACCTCTA CCTACC (SEQ ID NO: 8) | 334 |
| MOB3B | Chr9 27528300-27530603 | TTAAATTAAGGATAA ATTAAGATTT (SEQ ID NO: 9) | CCCTAAACTAAAAATA AAACCCCAC (SEQ ID NO: 10) | 318 |
| HLF | Chr17 53341098-53343562 | AAAAGTTTAGTAATA TTTTAGGGGG (SEQ ID NO: 11) | AAATAAACTCCTCAAT TTCATCAAC (SEQ ID NO: 12) | 348 |

Primer sequences that can be used to detect methylation in a region of Table 1 are shown in Table 7. In some cases, the primer sequences are in the 5' to 3' direction. In some cases, the primer sequence are in the 3' to 5' direction. The hypomethylated region designation (chromosome and chromosomal location) along with the primer sequences are shown in Table 7. In some cases, a region can have more than one primer pair this is indicated in Table 7. In some cases, the primer sequences can be used with a detection method described herein, such as a sequencing, a PCR, an array, a bisulfite conversion, or any combination thereof. In some cases, a primer sequence can comprise a sequence with at least about: 70%, 80%, 85%, 90%, 95%, 98%, or 99% sequence identity to any one of SEQ ID NOs: 13-46. In some cases, a primer sequence can comprise 100% sequence identity to any one of SEQ ID NOs: 13-46. In some cases, a primer sequence can comprise a sequence with at least about: 30%, 40%, 50%, 60%, 70%, 80%, 85%, 90%, 95%, 98%, or 99% sequence length to any one of SEQ ID NOs: 13-46.

TABLE 7

Primers for Detecting Hypomethylation of Regions in Sperm Cells

| Region Designation | Forward Primer | Reverse Primer |
|---|---|---|
| chr1: 182921660-182923994 | Pair 1: TTGTTGAGTGGGAAGTATTTTTAAAGTAAT (SEQ ID NO: 13) Pair 2: TTGTTTAGAGTTAGGTGGGATAGGG (SEQ ID NO: 14) Pair 3: TATTTTTAGGTATTGGTAGTAGGGGTTT (SEQ ID NO: 15) | Pair 1: CCCTACTACCAATACCTAAAAATAAAAAAAA (SEQ ID NO: 16) Pair 2: TCCCAATATAAAAATAAATTTTCTTTCAAA (SEQ ID NO: 17) Pair 3: ATAACCAAAAAATTCCAATTAATATCAC (SEQ ID NO: 18) |
| chr1: 35441734-35443497 | GTTTATAGTTATAGGGGTAGTATGTGGTTG (SEQ ID NO: 19) | ACCATAATCCTAAAATTCCTACTAATCTTC (SEQ ID NO: 20) |
| chr17: 43318045-43319383 | ATGGTTAAGATTGTAGAATTGGAAAAATAG (SEQ ID NO: 21) | TAAACTCCCCTCCAAACCCTAC (SEQ ID NO: 22) |
| chr17: 74302589-74304620 | GTTTAGGTTTTTTATTTGGTTTTTTAG (SEQ ID NO: 23) | TAAAAACAAAAACTCTATCCAATAACTC (SEQ ID NO: 24) |
| chr19: 10463037-10465258 | Pair 1: TTTTGTTTGTTTTAAGTGATTTTAGTATTTTTT (SEQ ID NO: 25) Pair 2: GAGAGTTTTTAATTGGTTAGGTTAGATTG (SEQ ID NO: 26) | Pair 1: TTTCTAACTCAACCTCCTTTTACTTAATAC (SEQ ID NO: 27) Pair 2: AACCCTCTACTTTAAAAAAAACCTAAATAC (SEQ ID NO: 28) |
| chr2: 128158047-128159059 | AAGTGTTTTTTGGAGGAGTTATTTATGAGG (SEQ ID NO: 29) | CTATTAACCTAAACCCAAAAACCAAAATAC (SEQ ID NO: 30) |

TABLE 7-continued

Primers for Detecting Hypomethylation of Regions in Sperm Cells

| Region Designation | Forward Primer | Reverse Primer |
|---|---|---|
| chr3: 9027157-9027577 | GATTTTTGTTTTTTAAGGTTAGGGTTATT (SEQ ID NO: 31) | AACCTAACTCCAAATCTCCAAACTATACTA (SEQ ID NO: 32) |
| chr4: 128650393-128652120 | TATAGGGTGAAATTTAAGGGGAATATTATT (SEQ ID NO: 33) | CCTACACCTACAACAACAACTTCAC (SEQ ID NO: 34) |
| chr4: 189580331-189580876 | TTTTATTTGGTTTATTGTTTATGGTTTAAT (SEQ ID NO: 35) | TAATAAATCCAACTTTATTCTATTCTTCATATAAC (SEQ ID NO: 36) |
| chr5: 121186479-121188229 | TTATTTTTATAGGTAAATTGGTGATTTTTG (SEQ ID NO: 37) | AAAAAAACCTAAAACAAAACAACATAAC (SEQ ID NO: 38) |
| chr7: 5540163-5541567 | GAGAAGGGGTTGGGATAGGATTGTA (SEQ ID NO: 39) | ACCATCTAATCCAACAAATCATCAAC (SEQ ID NO: 40) |
| chr7: 64330493-64331111 | TGTTTAGGTAGGTTGATATTTTTGATAGTT (SEQ ID NO: 41) | AATACACAACCCAACACATTCTAAAAC (SEQ ID NO: 42) |
| chr7: 6865886-6867075 | TGGTTTGTTGAATATAGAATTGAATAAAAT (SEQ ID NO: 43) | CTAAACAAAATTAAACAACATAAAAACCAC (SEQ ID NO: 44) |
| chr7: 75023589-75024730 | TTTTTTATGTTTTAGTTGTTTTTTTTGTGG (SEQ ID NO: 45) | ACAAATACCCAATATACCCTATATAATCCC (SEQ ID NO: 46) |

Biological Samples

In some embodiments, a biological sample herein can comprise a blood sample, a seminal fluid sample, a urine sample, a tissue sample, a biological fluid sample, or a semen sample. In some cases, a biological sample can comprise a DNA sample. In some instances, a DNA sample can be a DNA sample extracted from one or more cells, a cell free DNA sample, or a combination thereof. In some cases, a biological sample herein can comprise a pure sperm sample, a tissue sample, a cellular sample, a cell free DNA (cfDNA), or a cell free RNA (cfRNA) sample. In some cases, a cfDNA sample can comprise a cfDNA sample from a blood sample, a seminal fluid sample, a semen sample, a tissue sample, a urine sample, or a mixture thereof. In some cases, cfDNA can comprise DNA from a cell, for example a prostate cell, a cancerous prostate cell, a sperm cell or a combination thereof. In some cases, a cellular sample can comprise the cells of a biological sample. In some cases, a biological sample can be treated with an enzyme such as DNase, RNase or a mixture thereof to remove cell free DNA and/or cell free RNA. In some cases, a biological sample herein is obtained from a male subject.

In some cases, a biological sample herein can be obtained from the male reproductive system. In some cases, a biological sample can be obtained from an external urethral orifice, a glans penis, a penis, a urethra, a corpus spongiosum, a corpus cavernosum, a deep perineal pouch, a suspensory ligament, a urinary bladder, a vas deferens, a seminal vesicle, an ejaculatory duct, a prostate gland, a bulbourethral gland, an epididymis, a testis, a spermatic cord, a scrotum, or any combination thereof. In some cases, a biological sample can be obtained from a testis. In some cases, a testis can comprise a rete testis, a tunica albuginea, a seminiferous tubule, a lobule, a scrotum, a tunica vaginalis, a vas deferens, or any combination thereof. In some cases, a biological sample can be obtained from a prostate. In some cases, a prostate can comprise a central zone, a transitional zone, a peripheral zone, a fibromuscular stroma, or any combination thereof. In some cases, a method can comprise obtaining a biological sample from a region of the male reproductive system to detect the presence of sperm. For example, a method can comprise obtaining a biological sample from a testis, a seminal vesicle, a vas deferens, an ejaculatory duct, a urethra, a ejaculated semen sample to determine the presence of sperm by identifying a sperm associated methylation pattern as described herein. In some cases, a method can comprise obtaining a biological sample from a region of the male reproductive system to detect the presence of prostate cancer by identifying a prostate cancer associated methylation pattern in the biological sample.

Kits

Also disclosed herein are kits comprising a primer, a probe, or a combination thereof. In some cases, a kit can comprise a container. A container can be in the form of a glass, a metal, a plastic or any solid container. In some instances, a kit can comprise instructions for use. In some cases, an array, a primer, a probe, or any combination thereof can be used for the manufacture of a diagnostic reagent or kit for determining the presence or absence of a methylation pattern in a biological sample. In some instances, described herein is the use of arrays, primers, probes, or combination thereof for detecting DNA methylation patterns from DNA extracted from biological samples for the manufacture of a diagnostic kit. In some cases, a kit can comprise an array for detecting DNA methylation patters of the regions disclosed herein. In some cases, a diagnostic kit can be employed for determining a male infertility or determining the presence of a prostate cancer. In some cases, a diagnostic kit can be employed for determining the presence of a sperm in an article.

Methods of Treatment

Also disclosed herein are methods of treatment. In some cases, a method described herein, such as identifying the presence of a cell in a biological sample of a subject, can further comprise treating the subject. In some cases, the detection of the presence or absence of a sperm cell in a biological sample can comprise treating the subject with a fertility treatment. Also described herein, are methods of detecting sperm in a post-vasectomy analysis. In some instances, a method can comprise a surgery to repair, or complete the vasectomy if the presence of sperm is identified in post-vasectomy analysis. In some instances, a method can comprise a surgery to reverse the vasectomy if the presence of sperm is identified in post-vasectomy analysis. In some instances, a method can comprise a surgery to repair a vas deferens. In some cases, a surgery to repair a vas deferens can be employed if the presence of sperm is identified in the testes but not in a ejaculate semen sample. In some cases, the detection of a cancerous prostate cell in a biological sample from a subject can comprise treating the subject with a cancer therapy.

Methods disclosed herein can be used to treat azoospermia. In some cases, azoospermia can comprise obstructive azoospermia, non-obstructive azoospermia, or both. In some cases, non-obstructive azoospermia can comprise pretesticular non-obstructive azoospermia or testicular non-obstructive azoospermia. In some cases, pretesticular non-obstructive azoospermia can be caused by a hypogonadotropic hypogonadism, a hypothyroidism, use of certain medications, an elevated estradiol, Kallman's syndrome, a pituitary tumor, or a combination thereof. In some cases, testicular non-obstructive azoospermia can be caused by varicoceles, bilateral undescended testicles, cyptorchidism, testicular cancer, gonadotoxins, immunologic cause, Sertoli-cell only syndrome, incomplete development, a genetic syndrome, or a combination thereof. In some cases, obstructive azoospermia can comprise a vasectomy, a cystic fibrosis, an ejaculatory duct obstruction, a surgical complication, a phimosis, a scarring (e.g., from a sexually transmitted infection or an injury that causes scarring), a midline congenital cyst, or any combination thereof. In some cases, methods herein can be used to treat an ejaculatory disorder, a sperm production disorder, a bladder neck obstruction, a varicocele disorder.

In some cases, a treatment for infertility can comprise a surgery or a hormone treatment. In some cases, a surgery can comprise surgical repair of the varicocele. In some cases, a treatment for infertility can comprise concentration of sperm from the subject. In some cases, a treatment for azoospermia can comprise a surgery. In some cases, a treatment for infertility (e.g., azoospermia) can comprise a vasectomy reversal, a microsurgical testicular sperm extraction (micro-TESE), a testicular sperm extraction (TESE) a transurethral resection of the ejaculatory ducts (TURED), a circumcision, a surgical correction for scarring, or any combination thereof. In some cases, a treatment for infertility can comprise treatment with clomiphene citrate, clomid, prazosin, phenoxybenzamine, anastrazole, arimidex, a salt of any of these, or any combination thereof. In some cases, a treatment can comprise a vibratory stimulation. In some cases, a treatment for infertility can comprise treatment with an antibiotic. In some cases, a treatment for infertility can comprise a treatment for erectile dysfunction such as sildenafil, avanafil, tadalafil, vardenafil, a salt of any of these, or any combination thereof. In some cases, a treatment for erectile dysfunction can comprise a vacuum erection device (VED), a testosterone replacement, a urethral suppository, a penile injection, a penile implant, or any combination thereof. In some cases, a treatment for infertility can comprise an assisted reproductive technology. In some cases, a treatment can comprise treatment with human chorionic gonadotropin, recombinant human follicle-stimulating hormone, or both. In some cases, a treatment can comprise the concentration of sperm. In some cases, in vitro fertilization (IVF) can be used to treat male infertility.

In some cases, a treatment can comprise a vasectomy. For example, if a subject does not want to have sperm in their semen the methods described herein can be used to recommend a vasectomy for a treatment.

In some cases, the methods herein can be used to inform a practitioner the likelihood of the success of a treatment. For example, the identification of sperm from a biological sample in a subject with azoospermia can inform the practitioner that there is an increased likelihood that a therapy could be used to treat the subject. In another example, the absence of sperm in a biological sample in a subject with azoospermia can inform the practitioner there is a decreased likelihood that a therapy could be used to treat the subject.

Methods disclosed herein can be used to treat a prostate cancer. In some cases, a prostate cancer can comprise an adenocarcinoma, a small cell carcinoma, a neuroendocrine tumor, a transitional cell carcinoma, a squamous cell carcinoma, a lymphoma, or a sarcoma. In some cases an adenocarcinoma can comprise an acinar adenocarcinoma, a ductal adenocarcinoma, or both.

In some cases, a treatment for prostate cancer can comprise a chemotherapy, a surgery, a radiotherapy, a hormone therapy, a tissue ablation, an immune therapy, a chemical castration, or any combination thereof. In some cases, a chemotherapy can comprise a taxane chemotherapy, a platinum chemotherapy, carboplatin, cisplatin, oxaliplatin, docetaxel, cabazitaxel, mitoxantrone, estramustine, doxorubicin, vinblastine, paclitaxel, estramustine, a salt of any of these, or any combination thereof. In some cases, steroid can be administered to treat a prostate cancer, such as prednisone. In some cases, a treatment for prostate cancer can comprise enzalutamide, abiraterone, apalutamide, a salt of any of these, or any combination thereof. In some cases, an immune therapy can comprise sipuleucel-t, dostarlimab, pembrolizumab, a biosimilar of any one of these, or any combination thereof. In some cases, a chemical castration can comprise a luteinizing hormone-releasing hormone (LHRH) agonists. In some cases, a radiotherapy can comprise a external beam radiation therapy (EBRT), a intensity-modulated radiation therapy (IMRT), proton beam therapy, a stereotactic body radiation therapy (SBRT), stereotactic ablative radiation therapy (SABR), an image-guided radiation therapy, a brachytherapy, a radium-223 therapy, or any combination thereof. In some cases, a surgery can comprise a radical prostatectomy, an open or laparoscopic radical prostatectomy, a radical perineal prostatectomy, a laparoscopic prostatectomy, a laparoscopic radical prostatectomy, a robotic prostatectomy, a transurethral resection of the prostate, or any combination thereof. In some cases, a hormone therapy can comprise an androgen deprivation therapy, a orchiectomy, an luteinizing hormone-releasing hormone (LHRH) agonist, leuprolide, goserelin, triptorelin, leuprolide mesylate, an LHRH antagonist, degarelix, relugoix, abiraterone, ketoconazole, flutamide, bicalutamide, nilutamide, enzalutamide, apalutamide, darolutamide, histrelin, a salt of any of these, or any combination thereof.

In some cases, a tissue ablation can comprise a cryotherapy, a high intensity focused ultrasound, a photodynamic therapy, a laser ablation, or any combination thereof.

A treatment for a cancer can reduce the size of a tumor. In some cases, a treatment for a cancer can inhibit the growth of a tumor. In some cases, a treatment for a cancer can reduce the spread of a tumor. In some cases, a treatment for a cancer can substantially eliminate a tumor.

Administration

In some embodiments, methods described herein can comprise administering a therapy (e.g., treatment) to a subject in need thereof, for example a subject in need thereof can be a subject suffering from infertility or a subject having a prostate cancer.

In some embodiments, the terms "administer," "administering", "administration," and the like, as used herein, can refer to methods that can be used to deliver therapies described herein. In some cases, delivery can include injection, inhalation, catheterization, gastrostomy tube administration, intravenous administration, intraosseous administration, ocular administration, otic administration, topical administration, transdermal administration, oral administration, rectal administration, nasal administration, intravaginal administration, intracavernous administration, intracerebral administration, transurethral administration, buccal administration, sublingual administration, intrapenile drug delivery, subcutaneous administration, or a combination thereof. Delivery can include a parenchymal injection, an intrathecal injection, an intra-ventricular injection, or an intra-cisternal injection. A therapy provided herein can be administered by any method. In some cases, a medical professional can administer the therapy described herein. In some cases, a medical professional can comprise a urologist or a reproductive endocrinologist.

Administration of a therapy disclosed herein can be performed for a treatment duration of at least about: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 200, 300, 400, or more consecutive or nonconsecutive days. In some cases, a treatment duration can be from about: 1 to about 30 days, 1 to about 60 days, 1 to about 90 days, 30 days to about 90 days, 60 days to about 90 days, 30 days to about 180 days, from 90 days to about 180 days, or from 180 days to about 360 days.

Administration or application of a therapy disclosed herein can be performed for a treatment duration of at least about 1 week, at least about 2 weeks, at least about 3 weeks, at least about 4 weeks, at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 1 year, at least about 2 years, or for life. In some embodiments, administering can be performed for about: 1 day to about 8 days, 1 week to about 5 weeks, 1 month to about 12 months, or 1 year to about 3 years.

Administration can be performed repeatedly over a lifetime of a subject, such as once a month or once a year for the lifetime of a subject.

Administration or application of a therapy disclosed herein can be performed at least 1, 2, 3, 4, 5, 6, 7, 8, 9, 10, 11, 12, 13, 14, 15, 16, 17, 18, 19, 20, 21, 22, 23, or 24 times a in a 24 hour period. In some cases, administration or application of a therapy disclosed herein can be performed continuously throughout a 24 hour period. In some cases, administration or application of a therapy disclosed herein can be performed at least 1, 2, 3, 4, 5, 6, 7, 8, 9, 10, or more times a week. In some cases, administration or application of a therapy disclosed herein can be performed at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more times a month. In some cases, a therapy can be administered as a single dose or as divided doses. In some cases, a therapy described herein can be administered at a first time point and a second time point.

In some cases, a therapy herein can be administered at a dose of about 0.0001 grams to about 1000 grams. In some cases a therapy herein can be administered at a dose of about 1 mg to about 1 gram. In some cases, a therapy herein can be administered at a dose of about: 10 μg, 100 μg, 500 μg 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 60 mg, 70 mg, 80 mg, 90 mg, or 100 mg. In some cases, a therapy herein can be a pharmaceutical composition. In some cases, a therapy or a pharmaceutical composition can be in unit dose form.

In some cases, a therapy can be administered with an excipient, a carrier, a diluent or any combination thereof. In some cases, a carrier, a diluent, or both, can comprise water, saline, or any pharmaceutically acceptable carrier and/or diluent. In some cases, a diluent can comprise a pH buffer.

In some cases, an excipient can comprise a pharmaceutically acceptable excipient. In some cases, a pharmaceutically acceptable excipient can comprise acacia, acesulfame potassium, acetic acid, glacial, acetone, acetyl tributyl citrate, acetyl triethyl citrate, agar, albumin, alcohol, alginic acid, aliphatic polyesters, alitame, almond oil, alpha tocopherol, aluminum hydroxide adjuvant, aluminum oxide, aluminum phosphate adjuvant, aluminum stearate, ammonia solution, ammonium alginate, ascorbic acid, ascorbyl palmitate, aspartame, attapulgite, bentonite, benzalkonium chloride, benzethonium chloride, benzoic acid, benzyl alcohol, benzyl benzoate, boric acid, bronopol, butylated hydroxyanisole, butylated hydroxytoluene, butylparaben, calcium alginate, calcium carbonate, calcium phosphate, dibasic anhydrous, calcium phosphate, dibasic dihydrate, calcium phosphate, tribasic, calcium stearate, calcium sulfate, canola oil, carbomer, carbon dioxide, carboxymethylcellulose calcium, carboxymethylcellulose sodium, carrageenan, castor oil, castor oil, hydrogenated, cellulose (e.g. microcrystalline, powdered, silicified microcrystalline, acetate, acetate phthalate) ceratonia, cetostearyl alcohol, cetrimide, cetyl alcohol, cetylpyridinium chloride, chitosan, chlorhexidine, chlorobutanol, chlorocresol, chlorodifluoroethane, chlorofluorocarbons, chloroxylenol, cholesterol, citric acid monohydrate, colloidal silicon dioxide, coloring agents, copovidone, corn oil, cottonseed oil, cresol, croscarmellose sodium, crospovidone, cyclodextrins, cyclomethicone, denatonium benzoate, dextrates, dextrin, dextrose, dibutyl phthalate, dibutyl sebacate, diethanolamine, diethyl phthalate, difluoroethane, dimethicone, dimethyl ether, dimethyl phthalate, dimethyl sulfoxide, dimethylacetamide, disodium edetate, docusate sodium, edetic acid, erythorbic acid, erythritol, ethyl acetate, ethyl lactate, ethyl maltol, ethyl oleate, ethyl vanillin, ethylcellulose, ethylene glycol palmitostearate, ethylene vinyl acetate, ethylparaben, fructose, fumaric acid, gelatin, glucose, glycerin, glyceryl behenate, glyceryl monooleate, glyceryl monostearate, glyceryl palmitostearate, glycofurol, guar gum, hectorite, heptafluoropropane, hexetidine, hydrocarbons, hydrochloric acid, hydroxyethyl cellulose, hydroxyethylmethyl cellulose, hydroxypropyl cellulose, hydroxypropyl cellulose, low-substituted, hydroxypropyl starch, hypromellose, hypromellose acetate succinate, hypromellose phthalate, honey, imidurea, inulin, iron oxides, isomalt, isopropyl alcohol, isopropyl myristate, isopropyl palmitate, kaolin, lactic acid, lactitol, lactose, anhydrous, lactose, monohydrate, lactose, spray-dried, lanolin, lanolin alcohols, lanolin, hydrous, lauric acid, lecithin, leucine, linoleic acid, macrogol hydroxystearate, magnesium aluminum silicate, magnesium carbonate, magnesium oxide, magnesium silicate, magnesium stearate, magnesium trisilicate, malic acid, maltitol, maltitol solution, maltodextrin, maltol, maltose, mannitol, medium-chain triglycerides, meglumine, menthol, methylcellulose, methylparaben, mineral oil, mineral oil, light, mineral oil and lanolin alcohols, monoethanolamine, monosodium glutamate, monothioglycerol, myristic acid, neohesperidin dihydrochalcone, nitrogen, nitrous oxide, octyldodecanol, oleic acid, oleyl alcohol, olive oil, palmitic acid, paraffin, peanut oil, pectin, petrolatum, petrolatum and lanolin alcohols, phenol, phenoxyethanol, phenylethyl alcohol, phenylmercuric acetate, phenylmercuric borate, phenylmercuric nitrate, phosphoric acid, polacrilin potassium, poloxamer, polycarbophil, polydextrose, polyethylene glycol, polyethylene oxide, polymethacrylates, poly(methyl vinyl ether/maleic anhydride), polyoxyethylene alkyl ethers, polyoxyethylene castor oil derivatives, polyoxyethylene sorbitan fatty acid esters, polyoxyethylene stearates, polyvinyl acetate phthalate, polyvinyl alcohol, potassium alginate, potassium benzoate, potassium bicarbonate, potassium chloride, potassium citrate, potassium hydroxide, potassium metabisulfite, potassium sorbate, povidone, propionic acid, propyl gallate, propylene carbonate, propylene glycol, propylene glycol alginate, propylparaben, 2-pyrrolidone, raffinose, saccharin, saccharin sodium, saponite, sesame oil, shellac, simethicone, sodium acetate, sodium alginate, sodium ascorbate, sodium benzoate, sodium bicarbonate, sodium borate, sodium chloride, sodium citrate dihydrate, sodium cyclamate, sodium hyaluronate, sodium hydroxide, sodium lactate, sodium lauryl sulfate, sodium metabisulfite, sodium phosphate, dibasic, sodium phosphate, monobasic, sodium propionate, sodium starch glycolate, sodium stearyl fumarate, sodium sulfite, sorbic acid, sorbitan esters (sorbitan fatty acid esters), sorbitol, soybean oil, starch, starch (e.g. pregelatinized, sterilizable maize), stearic acid, stearyl alcohol, sucralose, sucrose, sugar, compressible, sugar, confectioner's, sugar spheres, sulfobutylether b-cyclodextrin, sulfuric acid, sunflower oil, suppository bases, hard fat, talc, tartaric acid, tetrafluoroethane, thaumatin, thimerosal, thymol, titanium dioxide, tragacanth, trehalose, triacetin, tributyl citrate, triethanolamine, triethyl citrate, vanillin, vegetable oil, hydrogenated, water, wax, anionic emulsifying, wax (e.g. carnauba, cetyl esters, microcrystalline, nonionic emulsifying, white, yellow), xanthan gum, xylitol, zein, zinc acetate, zinc stearate, or any combination thereof Computer Systems Also disclosed herein are computer control systems that are programmed to implement methods described herein.

For example, computer systems can be used for analyzing DNA from a sperm cell or cell free DNA in a seminal sample obtained from a male subject. In some cases, the computer system can comprise: a) a device for receiving sequenced data, wherein the sequenced data comprises sequencing of at least one region of Table 1; b) a device for comparing the sequenced data with a control pattern of a DNA methylation to determine the methylation of the sequenced data; and c) a device for determining a presence or an absence of a methylation pattern of the sequenced data. In some cases, the methylation pattern comprises the presence or absence of methylation of at least one region of Table 1. In some cases, sequence data comprises data obtained from the sequencing of bisulfite converted DNA.

In another example, computer systems can be used can be used for analyzing DNA from a prostate cell or cell free DNA in a seminal sample obtained from a male subject. In some cases, the computer system can comprise: a) a device for receiving sequenced data, wherein the sequenced data comprises sequencing of: (i) a promoter of: ZFP64, MOB3B, or HLF; (ii) a gene comprising: TCAF-1, CHST-11, or ALOX-5, or (iii) any combination of (i) and (ii); and b) a device for comparing the sequenced data with a control pattern of a DNA methylation to determine the methylation of the sequenced data; and c) a device for determining a presence or an absence of a methylation pattern of the sequenced data. In some cases, the methylation pattern comprises a hypermethylation or a hypomethylation of (i), (ii), or (iii).

In some cases, a device can be used for receiving an array and the data associated with an array. In some cases, a device can be used to compare the data from the array with a control. In some cases, the data from the array can be a methylation pattern. In some cases, a device can be a computer system.

Figure 4:
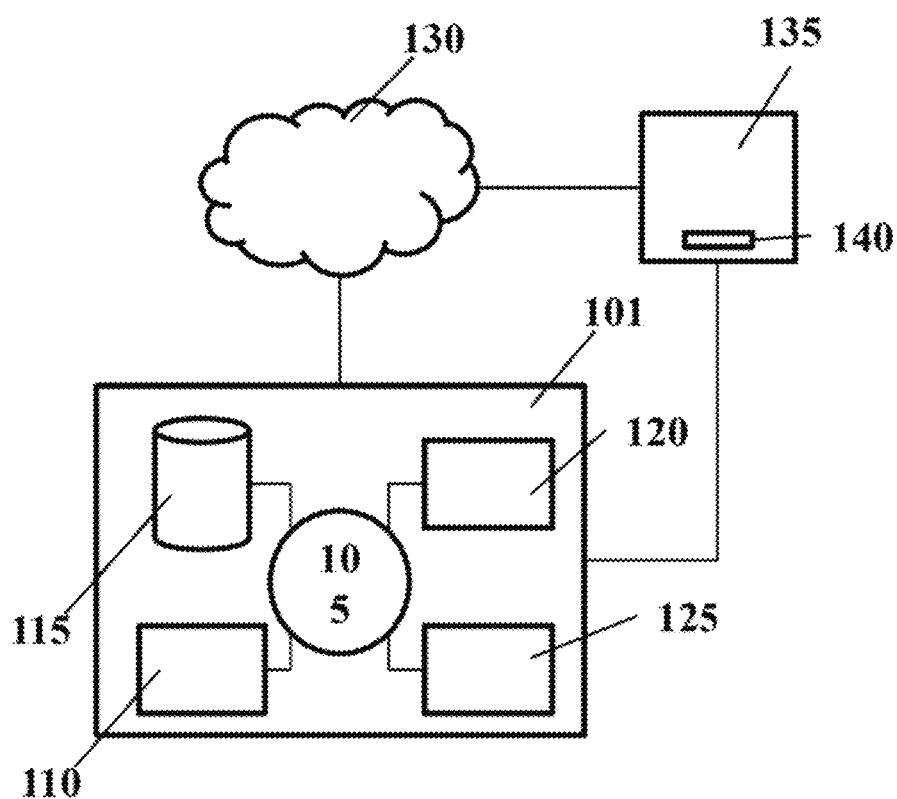
FIG. 4 shows a computer control system that is programmed or otherwise configured to implement methods provided herein.

FIG. 4 shows a computer system 101 that is programmed or otherwise configured to identify an methylation pattern from a patient's sample. The computer system 101 can regulate various aspects of the present disclosure, such as, for example determining a likelihood of a subject benefiting from a treatment to treat a disease (such as azoospermia). In another example, the computer system can be used to determine hypomethylation, hypermethylation or both hypomethylation and hypermethylation of a region of a chromosome or of a CpG site. The computer system 101 can be an electronic device of a user or a computer system that is remotely located with respect to the electronic device. The electronic device can be a mobile electronic device.

The computer system 101 includes a central processing unit (CPU, also "processor" and "computer processor" herein) 105, which can be a single core or multi core processor, or a plurality of processors for parallel processing. The computer system 101 also includes memory or memory location 110 (e.g., random-access memory, read-only memory, flash memory), electronic storage unit 115 (e.g., hard disk), communication interface 120 (e.g., network adapter) for communicating with one or more other systems, and peripheral devices 125, such as cache, other memory, data storage and/or electronic display adapters. The memory 110, storage unit 115, interface 120 and peripheral devices 125 can be in communication with the CPU 105 through a communication bus (solid lines), such as a motherboard. The storage unit 115 can be a data storage unit (or data repository) for storing data. The computer system 101 can be operatively coupled to a computer network ("network") 130 with the aid of the communication interface 120. The network 130 can be the Internet, an internet and/or extranet, or an intranet and/or extranet that is in communication with the Internet. The network 130, in some cases is a telecommunication and/or data network. The network 130 can include one or more computer servers, which can enable distributed computing, such as cloud computing. The network 130, in some cases with the aid of the computer system 101, can implement a peer-to-peer network, which may enable devices coupled to the computer system 101 to behave as a client or a server.

The CPU 105 can execute a sequence of machine-readable instructions, which can be embodied in a program or software. The instructions may be stored in a memory location, such as the memory 110. The instructions can be directed to the CPU 105, which can subsequently program or otherwise configure the CPU 105 to implement methods of the present disclosure. Examples of operations performed by the CPU 105 can include fetch, decode, execute, and writeback.

The CPU 105 can be part of a circuit, such as an integrated circuit. One or more other components of the system 101 can be included in the circuit. In some cases, the circuit is an application specific integrated circuit (ASIC).

The storage unit 115 can store files, such as drivers, libraries and saved programs. The storage unit 115 can store user data, e.g., user preferences and user programs. The computer system 101 in some cases can include one or more additional data storage units that may be external to the computer system 101, such as located on a remote server that is in communication with the computer system 101 through an intranet or the Internet.

The computer system 101 can communicate with one or more remote computer systems through the network 130. For instance, the computer system 101 can communicate with a remote computer system of a user (e.g., a lab technician, or health care professional). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 101 via the network 130.

Methods as described herein can be implemented by way of machine (e.g., computer processor) executable code stored on an electronic storage location of the computer system 101, such as, for example, on the memory 110 or electronic storage unit 115. The machine executable or machine readable code can be provided in the form of software. During use, the code can be executed by the processor 105. In some cases, the code can be retrieved from the storage unit 115 and stored on the memory 110 for ready access by the processor 105. In some situations, the electronic storage unit 115 can be precluded, and machine-executable instructions can be stored on memory 110.

The code can be pre-compiled and configured for use with a machine having a processer adapted to execute the code or can be compiled during runtime. The code can be supplied in a programming language that can be selected to enable the code to execute in a pre-compiled or as-compiled fashion.

Aspects of the systems and methods provided herein, such as the computer system 101, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 101 can include or be in communication with an electronic display 135 that comprises a user interface (UI) 140 for providing, for example, a methylation pattern of the subject. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 105. The algorithm can, for example, determine if a methylation pattern from a sample of a subject matches that of a sperm methylation pattern. In another example, an algorithm can determine if a methylation pattern from a sample (of a subject) comprises a methylation pattern of a cancerous prostate cell.

Figure 5:
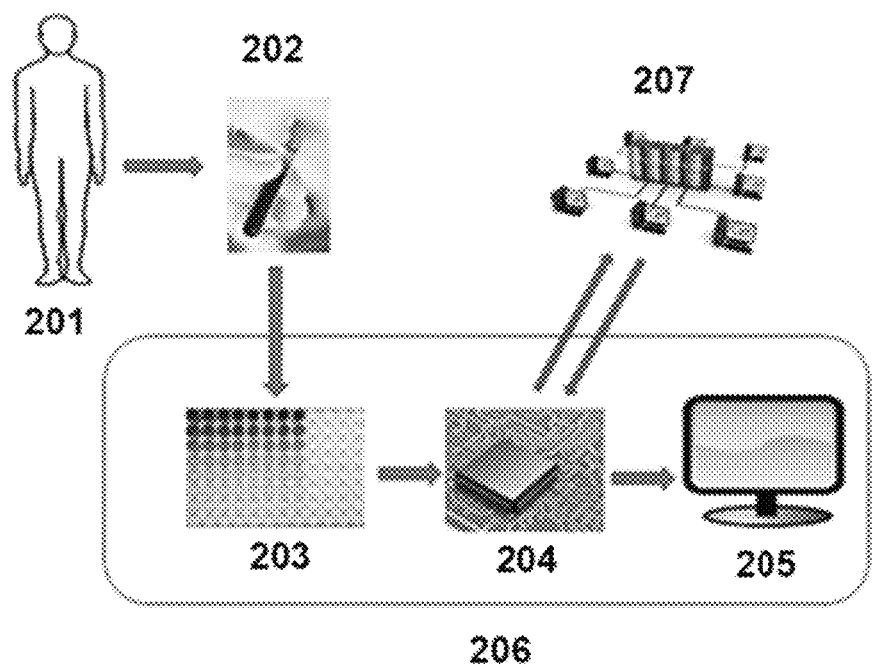
FIG. 5 shows a method and system as disclosed herein.

In some cases, as shown in FIG. 5, a sample 202 containing a seminal fluid sample can be obtained from a subject 201, such as a human subject. A sample 202 can be subjected to one or more methods as described herein, such as identifying the sample's methylation pattern by an array, by sequencing, by PCR, or any combination thereof. In some cases, an assay can comprise obtaining methylation pattern results, comparing the methylation pattern with a reference (e.g., control) sample, and displaying that information in a statistical readout (e.g., a spreadsheet, a graph, or a heatmap). One or more results from a method can be input into a processor 204. One or more input parameters such as a sample identification, subject identification, sample type, a reference, or other information can be input into a processor 204. One or more metrics from an assay can be input into a processor 204 such that the processor can produce a result, such as determining a likelihood of a subject benefiting from a treatment to treat a disease (such as azoospermia). A processor can send a result, an input parameter, a metric, a reference, or any combination thereof to a display 205, such as a visual display or graphical user interface. A processor 204 can (i) send a, an input parameter, a metric, or any combination thereof result wirelessly or directly to a server 207, (ii) receive a result, an input parameter, a metric, or any combination thereof from a server 207, (iii) or a combination thereof. In some cases, the output can be a heatmap or a statistical output.

EXAMPLES

Example 1—Assessment of Seminal-Cell Free DNA

Human seminal cell-free DNA (cfDNA) methylation patterns are currently being explored, however, recent work in mouse has suggested that some cfDNA encountered in the epididymis may contaminate DNA methylation studies assessing the mature sperm. Such contamination could be confounder, for many reasons, in epigenetic studies of male factor infertility. The objective of the study was to explore the nature of seminal cfDNA methylation and the likelihood that it would be retained following standard semen sample processing for epigenetic analysis.

12 semen samples were collected at a Fertility Center. For each sample, seminal cfDNA was isolated from the sperm pellet. The sperm was split into three aliquots including one exposed to DNase to remove any additional cfDNA (termed "pure sperm"), one not exposed to DNase, and one exposed to DNase but reintroduced to seminal cfDNA. Blood DNA was assessed as our benchmark for somatic cell DNA methylation patterns. DNA methylation was measured via Illumina's 850k array and assessed for differential regional methylation.

46,352 differentially methylated regions (FDR>40) were identified between pure sperm and seminal cfDNA. The average DNA methylation at these site in cfDNA always fell somewhere between the average methylation in sperm and in blood. Each sperm treatment group was assessed at all 46,352 regions of interest and no significant differences were identified at any of these sites.

The data suggest that seminal cfDNA is a clear mixture of both somatic and germline DNA and that cfDNA is not a contaminating feature in sperm DNA methylation studies following standard protocols in human sperm DNA extraction.

It has been estimated that 1 in 8 couples experience some form of infertility and 50% of these cases include male factor infertility as a contributing factor. Of these cases, which impact approximately 9% of all men, 60-75% are idiopathic in nature with no known etiology. This has made diagnosis of male factor infertility particularly difficult. The conventional tools used in the assessment of a male infertility diagnosis, such as the semen analysis, may only be effective at identifying the most severe forms of male factor infertility such as nonobstructive azoospermia (NOA) which occurs in approximately 10% to 15% of infertile men. This is possible because NOA represents a complete absence of sperm in the ejaculate which is easy to detect.

Because the total number of sperm or the quality of sperm (motility, morphology, etc.) are not excellent predictors of pregnancy success (except in the most extreme of cases) it is not surprising that most cases of infertility are idiopathic in nature since this is precisely what the diagnostic assays described herein target. This has been thoroughly recognized as a field and, as a result, there has been a robust search for more predictive male infertility diagnostics. One approach is the approach of screening sperm epigenetics for predictive markers to explain some of the cases of idiopathic male infertility. This has produced many intriguing results that have shown a correlation between DNA methylation signatures and male infertility in different forms. Specifically, these studies have identified specific patterns of epigenetic dysregulation that are associated with teratozoospermia, asthenozoospermia and fecunditiy in general. Specific DNA methylation signatures have been identified that appear capable of discriminating between patients who will need to utilize IVF and those that will not.

Because epigenetic marks, and in particular DNA methylation, are highly varied between cell types, sperm cells should be isolated from somatic cells to effectively perform infertility research. Many procedures have been employed to ensure that somatic cell removal is performed efficiently so that the results from sperm epigenetic analyses can be trusted. In fact, our lab recently created a simple PCR/restriction enzyme-based assay to provide a "pre-screening" of DNA to ensure sample purity. Such care needs to be taken particularly in DNA methylation studies of low sperm count where somatic DNA contamination can create an even bigger confounding effect as the ratio of somatic cells to sperm cells in the ejaculate could be significantly increased due to low sperm count even without elevated somatic cell contamination. While these procedures have provided confidence in our removal of somatic cells, a recent publication using mice has raised concerns regarding the presence of persistent somatic DNA with mature sperm. The group found that cfDNA could adhere to the outside of mature sperm cells in mice which resulted in altered DNA methylation signatures when assessing DNA methylation in mature sperm cells. Importantly the sperm appeared to be contaminated even in the vas deferens. If such contamination exists there, it is possible that it may also exist in the ejaculated sperm (though this was not directly explored in mice). This potential source of contamination in human ejaculated sperm was tested to ensure that epigenetic analyses used to assess fertility can rule out or address this contamination directly. Thus, the work described in this example is designed to evaluate the differences between seminal cfDNA methylation signatures and sperm DNA methylation signatures as well as the adherence of cfDNA to the outside of mature, ejaculated human sperm cells.

Methods

Study Participants

The study assessed 12 human semen samples that were collected from patients seeking fertility care at Utah Fertility Center in Pleasant Grove, Utah, USA. The semen samples were collected following standard protocols including abstinence for 3 to 5 days. Immediatiy following the completion of a standard semen analysis (Table 5), the remaining portion of each sample, which would have typically been discarded, was frozen in a test yolk buffer (TYB; Irvine Scientific) and preserved for future analyses. To observe results across multiple fertility phenotypes, samples were selected based on their varying sperm counts.

TABLE 5

Semen analysis results

| Semen Analysis Parameter | Average ± Standard Error |
|---|---|
| Sperm Count (millions/milliliter) | 66.76 ± 14.80 |
| Motility (%) | 58.42 ± 3.87 |
| Morphology (% normal) | 4.73 ± 1.56 |
| Total Count (millions) | 289.48 ± 60.33 |

Sample Processing and Study Group Preparation

All samples were thawed and processed simultaneously to avoid any batch effects during processing (the study workflow can be seen in FIG. 1). Each sample was centrifuged to isolate the cell fraction from the seminal plasma, which was used to isolate seminal cell free DNA (cfDNA), and the cfDNA was set aside for use in the study. The sperm pellet underwent somatic cell lysis according to the standard procedure. The resulting pellet was then divided into three equal aliquots yielding 4 distinct groups being assessed in our study (including cfDNA alone and the three aliquots). 1) The first aliquot, hereafter referred to as the "pure sperm group," underwent a DNase treatment to remove all potentially contaminating cfDNA (which may have originated from somatic sources) that might either be in solution or bound to the sperm cell surface. DNase digestion was performed using Qiagen RNase-Free DNase Set following manufacturer's guidelines. 2) The second aliquot, referred to as the "untreated group," was not exposed to DNase and thus, if cfDNA was fixed to the surface of the sperm cell, the sperm DNA may be potentially contaminated by somatic DNA. 3) The final group, referred to as the "add-back group," went through the same process as the pure sperm group; however, following DNase treatment, a portion of the cfDNA that was initially isolated from each sample was added back and incubated for 30 minutes with the DNase treated sperm with no subsequent DNase digestion. The purpose of this final group was to determine if DNA introduced to sperm following DNase digest, could adhere to the sperm surface if reintroduced DNA Extraction/Bisulfite Conversion/Array Processing In all three groups described above, sperm DNA extraction was performed by adding a sperm specific modification (utilizing DTT and proteinase K) to the DNeasy DNA extraction kit (Qiagen). Additionally, the cfDNA from each sample was extracted following Qiagen's QIAamp MinElute ccfDNA Mini Kit standard protocol. The DNA from each group was then subjected to bisulfite conversion with the EZ DNA methylation kit (Zymo). Bisulfite converted DNA was then submitted for array hybridization and processing on Illumina 850K (EPIC) human methylation arrays. The resulting data (.idat files) was submitted for computational analysis.

cfDNA Quality Assessment

Extracted cfDNA was assessed for both quality and quantity. For all DNA samples we utilized a Qubit 4 fluorometer. We additionally assessed the fragment sizes of cfDNA using a bioanalyzer.

Statistical Analysis and Unsupervised Clustering Analysis

The raw methylation data was processed using base R software and the minfi software package in R 13. Minfi was used to convert raw intensities values from the array to beta-values (or fraction methylation values) that represent the amount of methylation at each CpG site analyzed (with 0 indicating completely unmethylated and 1 indicating completely methylated). The beta-values were formatted in a table with the aid of a computer program that linked metadata to each CpG.

Once the data was normalized and organized, unsupervised hierarchical clustering was used to determine any patterns inherently present in the data. The data was regionalized for this analysis using the average methylation at each CpG island (total of 27,164 CpG islands annotated on the array) from each individual. Additionally, the data was used to perform clustering using the heatmap function.

Regional Differential Methylation Analysis

Regional differential methylation was performed using the Methylation Array Scanner and Enriched Region Maker apps in a Java based computer program called USEQ. The Methylation Array Scanner compares two groups of data using a sliding window approach through the entire genome (at all 850,000 positions tiled on the array in genomic context) looking for differences between the two samples. Importantly, and unlike some other approaches to regional differential methylation analysis, this method does not impose specific boundaries as they are defined in terms of genome context (promoters, enhancers, etc.). This allows the analysis to define regions that appear to move together and define the boundaries of the region. Upon completion of the Methylation Array Scanner the resultant data is then run through Enriched Region Maker which creates a data frame that includes the list of differentially methylated regions between the two groups, how many CpGs are located in each region as well as phred scaled FDR values for each site. Our threshold of significance in this analysis included 3 filters: an FDR >40 (approximately equivalent to an adjusted p-value of 0.001), a log 2 ratio >0.2, and a minimum of 3 CpGs per region. This regional analysis was performed initially only between the cfDNA group and the pure DNA group to identify the areas expected to be differentially methylated as a result of cfDNA contamination. Identified areas of differential methylation between cfDNA and pure DNA were then assessed region by region in the untreated DNA and add-back DNA groups using t-tests to assess for significant differences from the pure DNA group.

Assessment of Scale of Differential Methylation

To determine the widespread differences in methylation between distinct sources of DNA, the regions of differential methylation were assessed against the background number of possible regions based on the analysis approach. Any genomic enrichment was assessed for the differential methylation both at CpG island context as well as globally.

Pathway Analysis of Regions of Significance

The Genomic Regions Enrichment Analysis Tool (GREAT) was used to perform a pathway enrichment analysis of the significant regions identified in the analysis.

Results

Seminal cfDNA Characteristics

Figure 2A:
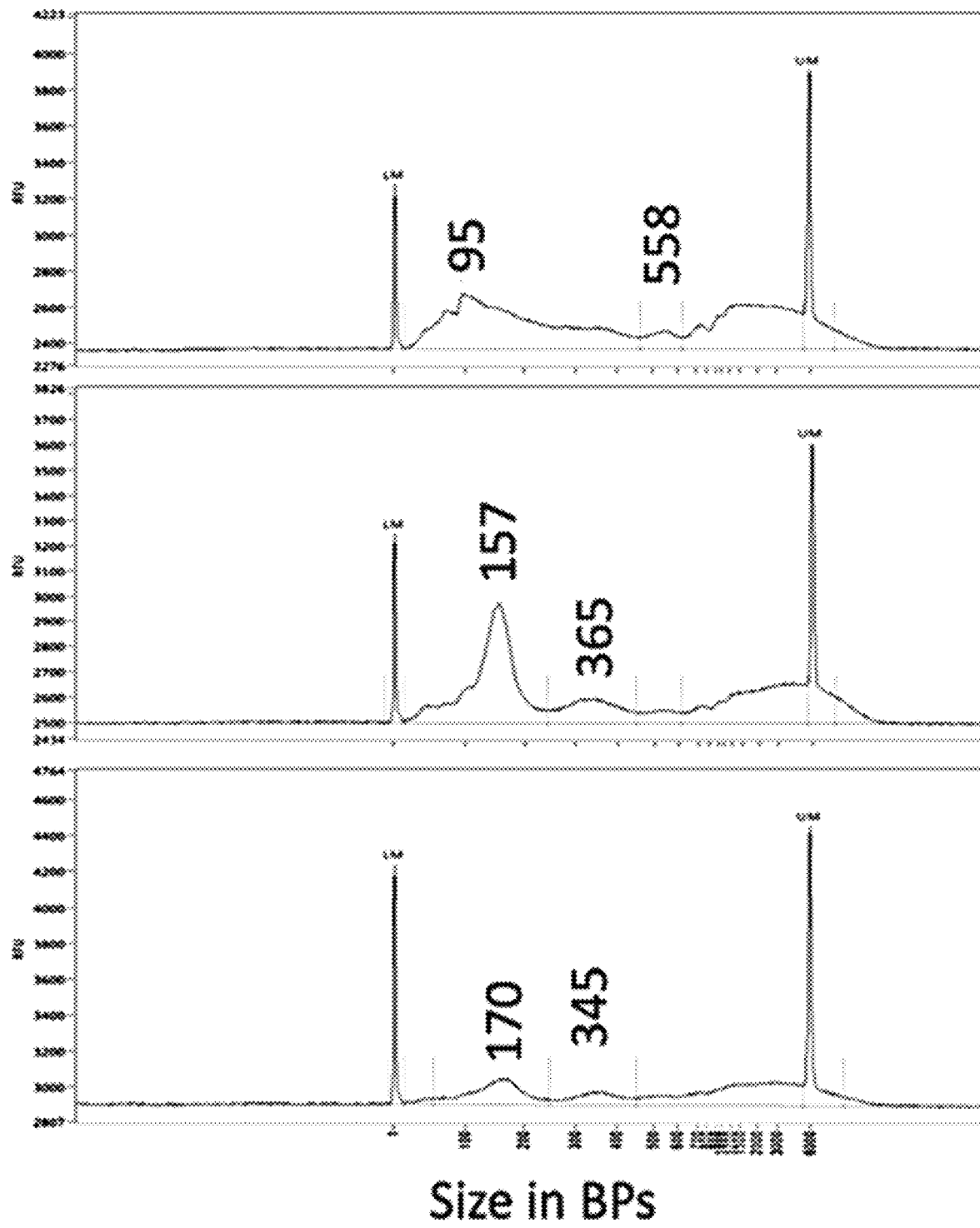
FIG. 2A-2C shows analysis of the DNA extraction results and a heatmap of the average methylation at all CpG islands in the array.
Figure 2B:
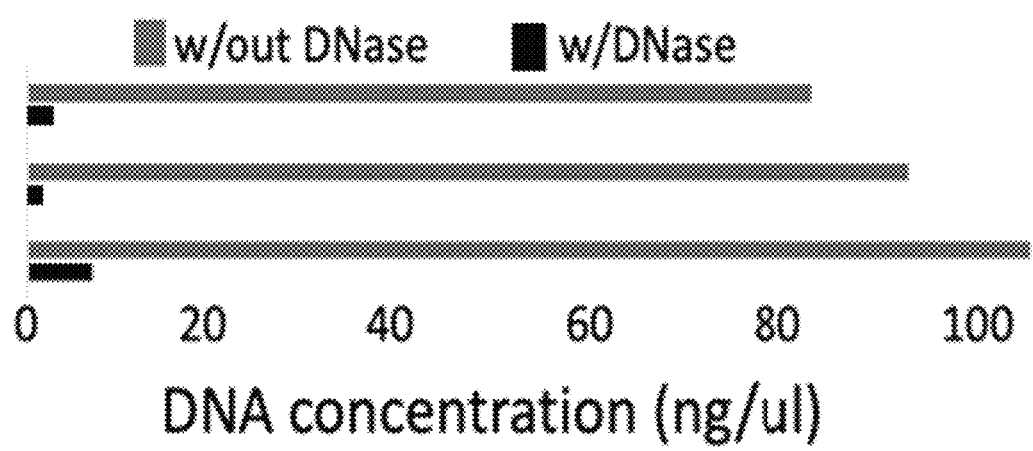

Following cfDNA extraction, the quantity and quality of DNA was assessed to ensure it would be usable for array analysis and to provide basic descriptive metrics that other researchers could use since very little work has been done on seminal cfDNA. The extraction protocol for cfDNA yielded an average of 575.25 ng (±SE of 79.16) of DNA. DNA quality was reasonable for our application with fragment sizes ranging from approximately just below 100 base pairs to over 6,000 base pairs in length (FIG. 2A). It should be noted that there was significant variability present in fragment lengths, but all samples fell somewhere in this range Efficiency of DNase Digestion To ensure that the DNase digestion protocol was effectively removing potentially contaminating DNA, the DNase digestion protocol was performed in three DNA samples. The DNase digestion protocol removed on average 96.25% of all DNA present in a sample (FIG. 2B).

Unsupervised Clustering

Figure 2C:
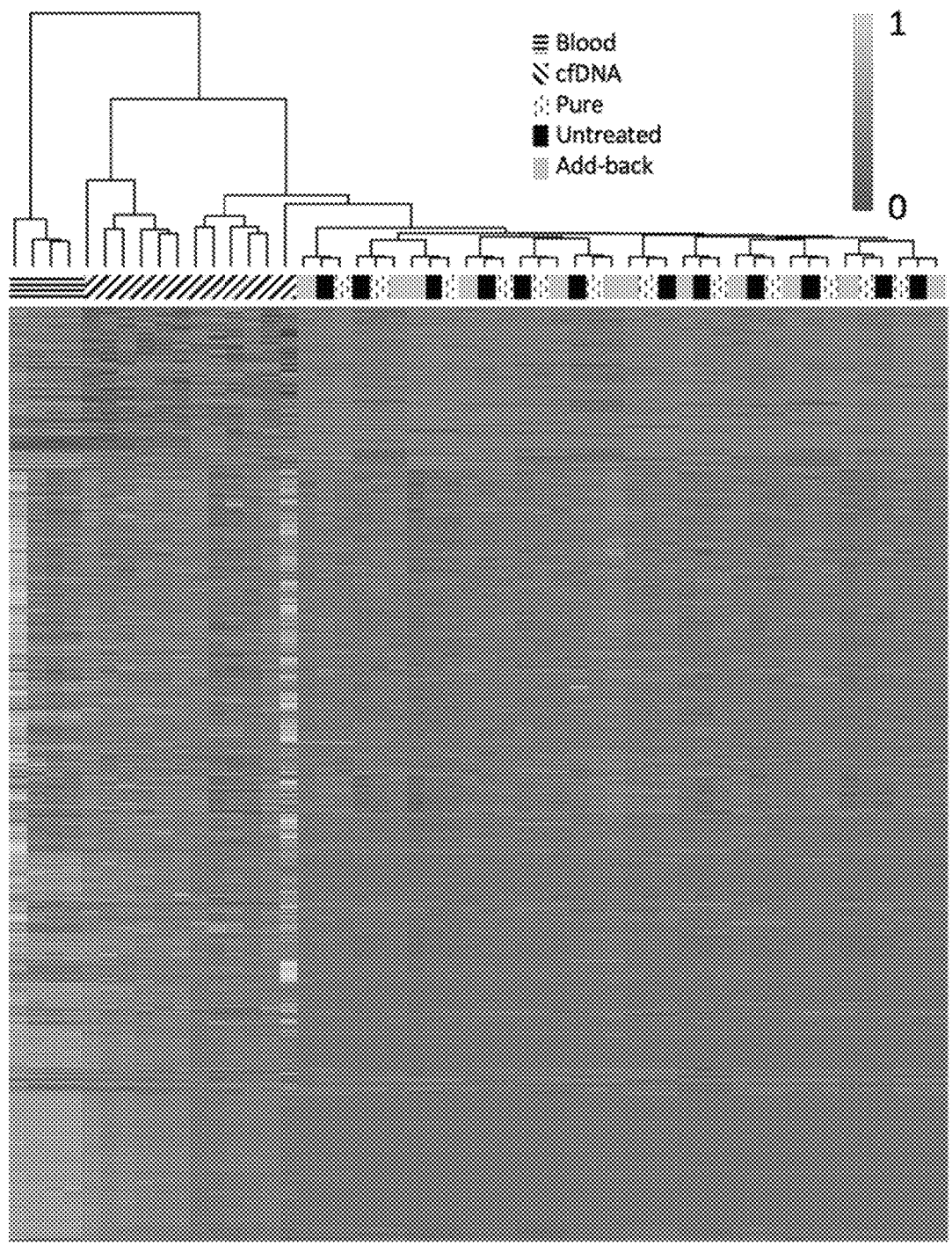
Figure 3A:
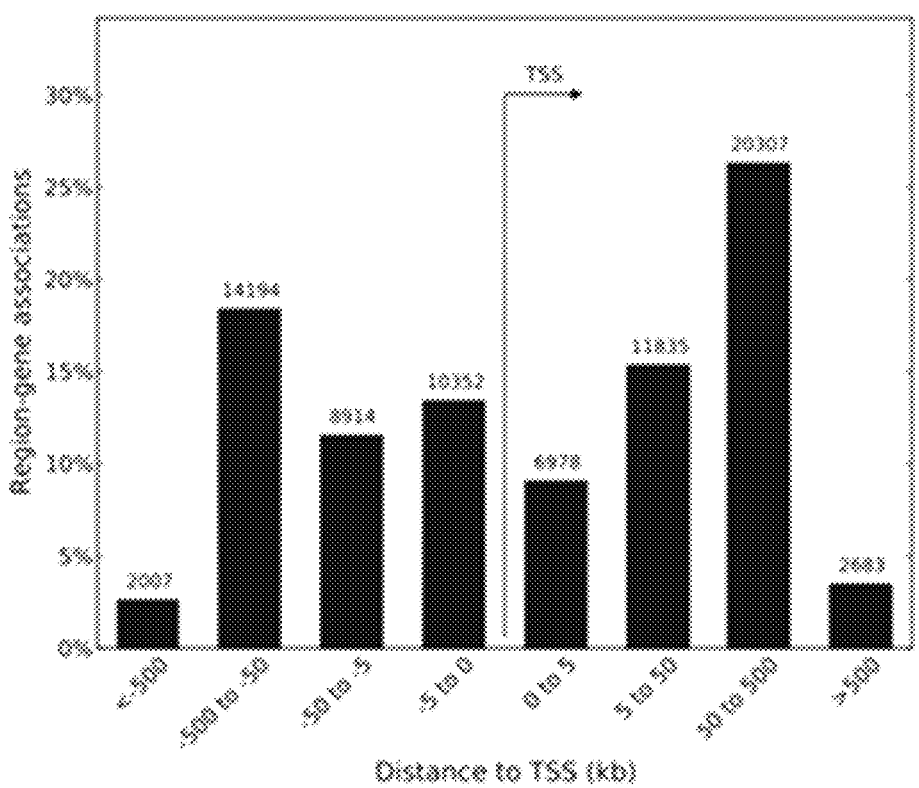
FIG. 3A-3F shows the results of the methylation comparison of blood, cfDNA, pure sperm, untreated sperm, and add-back sperm.
Figure 3B:
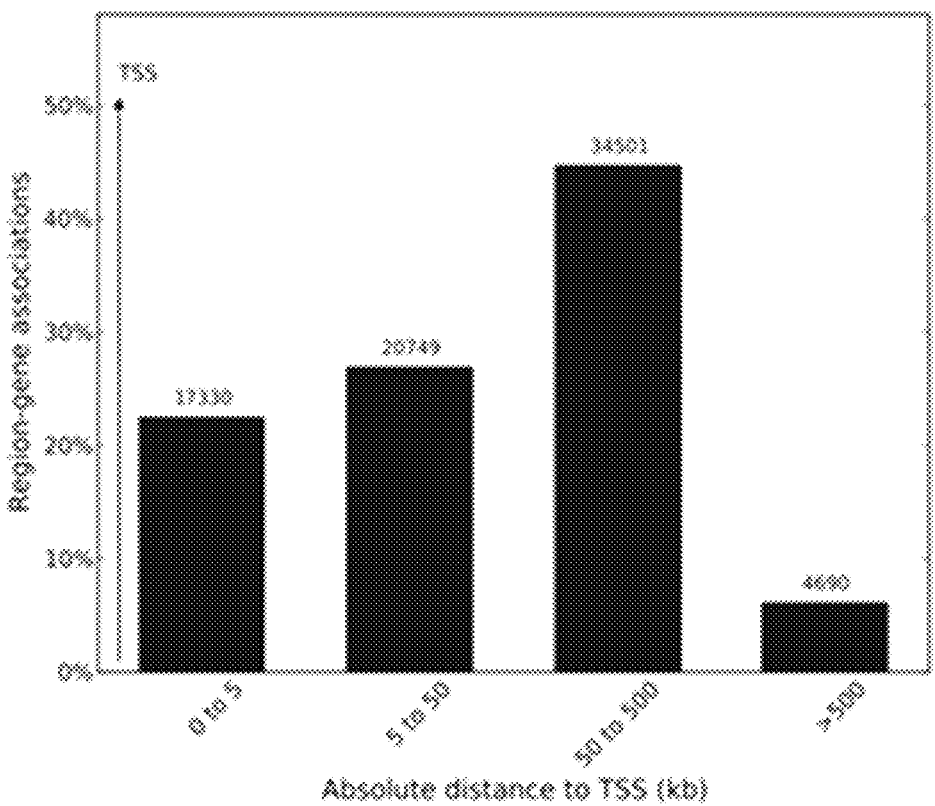
Figure 3C:
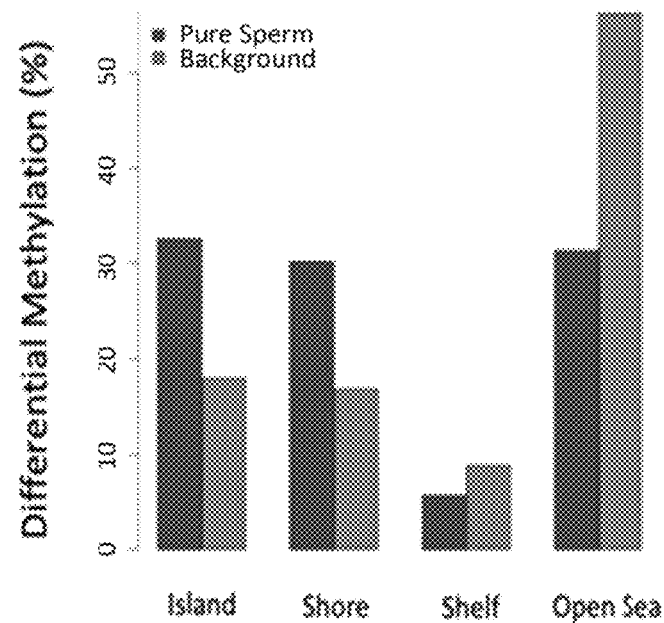
Figure 3D:
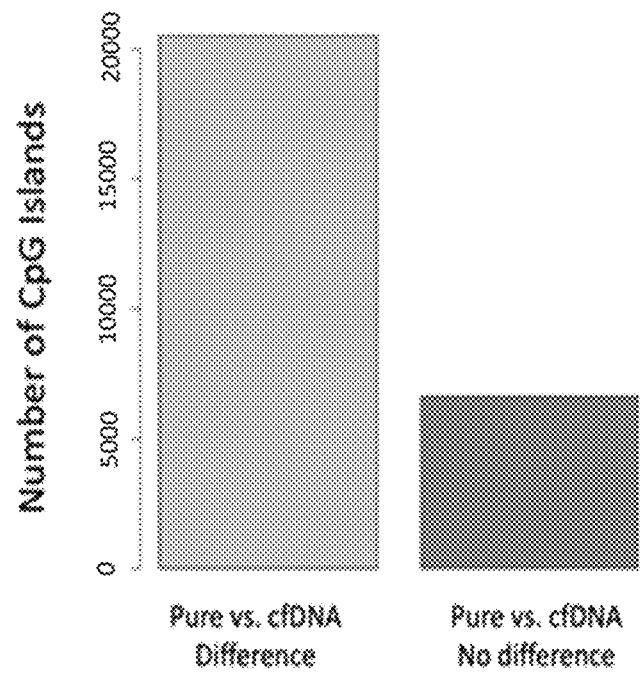

To determine if any widespread differences were present between the groups a unsupervised hierarchical clustering was performed. 4 samples of blood DNA was used as a representative sample of somatic DNA (as this is present in the cfDNA fraction of the seminal plasma). The entire array was not used for this analysis, instead the methylation was averaged at every single CpG island for each sample and the analysis was performed using these data. The clustering yielded a few important findings even before the differential methylation analysis (FIG. 2C). First, blood and sperm samples (each treatment type) cluster completely independently from one another, All cfDNA samples clustered together and in-between the sperm and the blood. The heatmap shows that in most cases the cfDNA had average methylation values somewhere in-between the sperm and the blood suggesting that both somatic and germ cell DNA is present in the DNA source. No clustering of the different treatment groups was identified. The different paired samples clustered based on the individual, and not the treatment. This suggests that, at least broadly, there is no clear difference between the treatment groups and thus likely no cfDNA being assessed with our typical protocols to isolate sperm DNA The sliding window approach resulted in 46,352 significant regions of differential methylation with representation on each chromosome. The analysis showed that most of the differentially methylated regions were within 500 kb of a transcriptional start sight (FIG. 3B). It was also determined that the differences were spread evenly between islands, north and south shore, and open sea. Interestingly, few differences were identified in the north and south shelf region. (FIG. 3C) Comparison of the differential data with the potential array data show that differences were identified at most of the CpG sites available. (FIG. 3D)

Figure 3E:
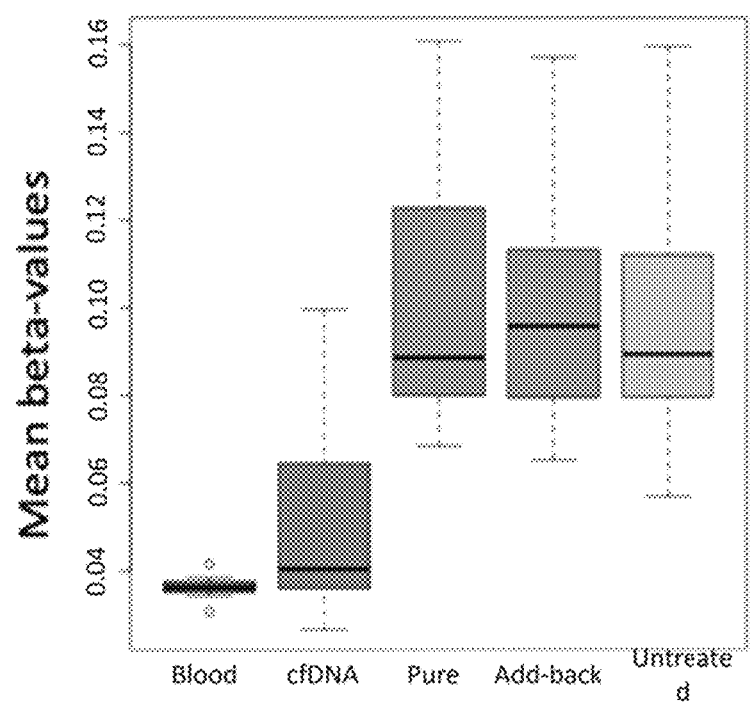

A Wilcoxon FDR threshold of 40 to be conservative was used, and a large portion (20%) of the differentially methylated regions had a Wilcoxon FDR >80. All differentially methylated regions identified from the initial analysis (cfDNA vs pure sperm DNA) were parsed out of the remaining two groups (add-back and untreated) to determine if sites that could have caused altered methylation results due to contamination would have shown this contamination in samples treated in a normal fashion. Beta values were averaged for each region of differential methylation in each sample from each treatment group. The analysis of pure DNA compared to both add-back DNA and untreated DNA resulted in no significant regions of differential methylation. A visual comparison was made with a boxplot (FIG. 3E and FIG. 3F) using two representative regions within the regional analysis which showed significant difference in the comparison of cfDNA with pure DNA but no difference between pure DNA, add-back, or untreated groups. The plot shows a visible difference between the mean differential methylation of the cfDNA extraction and the sperm extractions which do not appear to have a significant difference as the p-values suggest. A comparison to blood was also made with beta-values from previously processed data. A visual difference between blood methylation signatures and cfDNA and sperm DNA is noted at these two regions.

Pathway Analysis Using GREAT

The Genomic Regions Enrichment of Annotations Tool (GREAT) was used to assess for any enrichments in specific pathways in the 46,352 regions that were identified. Due to the large number of significant regions that covered a majority of genes, enriched pathways were not identified.

Discussion

The presence of cfDNA in seminal fluid has the potential to yield important insights in reproductive pathologies as well as potential diagnoses and treatments. However, based on previous findings in mouse, it also appears to have potential to confound differential methylation analysis if it was commonly contaminating methylation data sets in sperm. Thus, it is essential that reasonable tests are employed to ensure that such contamination is not present when performing commonly utilized techniques in sperm epigenetic assays. Specifically, DNA fragments can adhere to the outside of mouse sperm cells which, if present in humans, could alter the methylation signature of sperm DNA. To be confident in the purity of the DNA it was important to show that either DNA does not adhere to the outside of sperm cells, or that we are able to remove the fragments during extraction. The regional differential methylation analysis in our study yielded a large number of regions of differential methylation between sperm DNA and cfDNA. Importantly, when looking at these same regions, the epigenetic signatures did not change in any significant way between sperm that was treated with DNase or sperm that was not treated prior to DNA extraction. It is possible that this is due in part to differences in the amount of DNA in sperm and in the cell free fraction of the semen with sperm DNA being at a much higher concentration than cfDNA. However, based on previous analyses we know that we are capable of identifying even very small alterations in the methylome with the techniques described herein. Further, if the contamination is so minute or so inconsistent that even the most sensitive techniques can not detect it, then that level of contamination may be of no concern in population based analyses of DNA methylation in human sperm which is the main concern of this example. Taken together, these data support the conclusion that fragments of DNA either do not adhere to human sperm or are removed with our typical preparations for DNA methylation analysis. In short, this form of contamination does not appear in our data and is thus, not a factor in our analysis It is also worth noting that the methylation analysis clearly shows that sperm DNA has a different signature than the cfDNA fraction. It can be noted that when comparing mean beta-values of blood and sperm that the DNA from the cfDNA extraction typically exhibited mean beta-values somewhere between the two. This leads to the conclusion that the DNA present in the cfDNA extraction contains both somatic and germ line DNA which may prove useful for other applications in the future. It is also important to consider the potential origin of the sperm DNA in the seminal cfDNA. Because frozen sperm was assessed in the analysis, it is possible that this process liberated some DNA from the mature sperm and not from dying sperm in the reproductive tract. However, this may be unlikely due to the unique nature of sperm chromatin and the presence of protamines, sperm DNA is very difficult to access with mechanical or detergent based disruption of cell membranes (which is likely similar to the freeze thaw cycle) and requires specific chemicals (such as DTT) to access the DNA. This coupled with the small fragment sizes suggests that this sperm cfDNA may not be arising from the freeze thaw cycle on mature sperm though this cannot be ruled out.

Figure 3F:
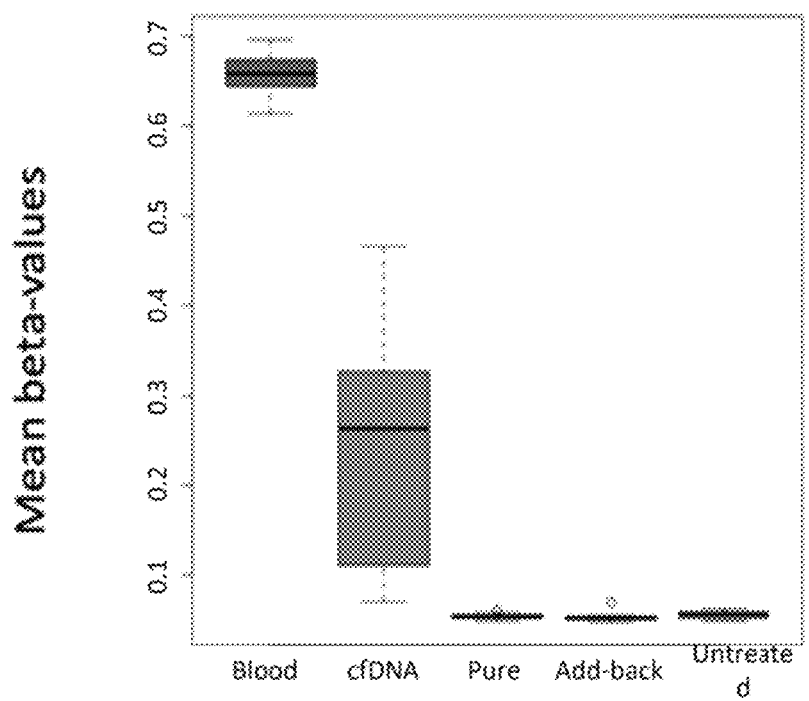

While some work has been performed on seminal cfDNA, the cells that contribute to this source of DNA are unknown. It is logical to assume though that DNA from virtually every cell type in the urogenital tract may be present in the semen. Because epigenetic analysis is highly specific to cell or tissue type, it is possible that we could, in the future, identify the original source of some DNA present in the cfDNA fraction, and this may have utility in clinical care for male infertility. Of particular interest in this dataset were findings surround the fact that while sperm DNA methylation was very similar between samples, the cfDNA fraction was quite variable (FIG. 3F). This variability was present both in terms of fragment size and DNA methylation patterns. There could be underlying biology that drive these differences even in our samples that were relatively similar in terms of semen analysis metrics. This technique could be used for assessing seminal cfDNA and its cellular origins as we believe this could be linked to various forms of infertility. This is particularly intriguing in cases of severe infertility as it is not unreasonable to assume that under certain pathologies, different cell types in the urogenital tract will undergo apoptosis more regularly and thus result in varying amounts and types of cfDNA. If this occurs in the cells found in the testes, these patterns may be predictive of outcomes or indicative of specific fertility etiologies.

Example 2—Methylation Differences Between Seminal Cell Free DNA (cfDNA) Vs. Sperm Cell DNA Regional differential methylation was performed on seminal cfDNA and sperm DNA using the Methylation Array Scanner and Enriched Region Maker apps in a Java based computer program called USEQ. The Methylation Array Scanner compared the two groups of data (seminal cfDNA vs. sperm DNA) using a sliding window approach through the entire genome (at all 850,000 positions tiled on the array in genomic context) looking for differences between the two samples. Upon completion of the Methylation Array Scanner the resultant data was ran through Enriched Region Maker which created a data frame that included the list of differentially methylated regions between the two groups and how many CpGs were located in each region as well as phred scaled FDR values for each site. Our threshold of significance in this analysis included 3 filters: an FDR >40 (approximately equivalent to an adjusted p-value of 0.001), a log 2 ratio >0.2, and a minimum of 3 CpGs per region. This regional analysis was performed on the cfDNA and the sperm cell DNA samples The highest FDR and log 2 ratios from the comparison of cfDNA and sperm DNA were selected and presented in Table 1.

Regions of hypermethylation in somatic cells (seminal cfDNA) in comparison to sperm cells is shown in Table 1. Similarly, Table 1 shows the regions of hypomethylation in sperm cells in comparison to somatic cells. Table 1 depicts the chromosome number and start and stop location on the chromosome of the hypomethylated regions in sperm DNA as compared to somatic cell DNA. The region designation is in reference to the reference genome is HG19 (GenBank assembly accession: GCA_000001405.1). The National Center for Biotechnology Information (NCBI) description for the genome is provided in Table 3. Table 2 provides information on the individual CpG sites identified in the regions from Table 1. The "Region Designation" in Table 2 corresponds to the region designation in Table 1. The "Chromosome" column indicates the chromosome number of the region of methylation, the "Location" column indicates the chromosomal location of individual CpG sites of potential methylation within the region designation. The "Gene" column indicates the gene associated with the region of differential methylation. The "Gene region" column provides detailed information on the CpG sites and their relation to the designated gene.

Table 1 provides specific regions of hypomethylation in sperm cells. The lack of methylation within one or more of the regions in Table 1 can be used to identify a sperm cell from a biological mixture. Any combination of the regions in Table 1 can be used to identify a sperm cell from a biological mixture. The absence of methylation or the hypomethylation of one or more of these regions can indicate that a sperm cell is present in a sample.

Example 3—Assessment of Prostate Cell Free DNA in Seminal Fluid

Publicly available genomic databases were queried for cancerous ("Cancerous Prostate Tissue" in FIG. 6) and normal prostate tissue ("Normal Prostate Tissue" in FIG. 6). Data was selected using the following criteria: samples were analyzed using Illumina 450K or EPIC arrays, data were available in IDAT or normalized CSV/TSV format, and had clinical pathological annotations. Additionally, samples of seminal cell free DNA ("Seminal Cell-Free DNA" in FIG. 6) were examined. 136 total samples of cancerous tissue and normal tissue were selected and 12 samples from normal seminal plasma cell free DNA were selected. Delimited beta values were prepared for a sliding window analysis between cancerous and normal, using USEQ's Methylation Array Scanner and Enriched Region Maker, selecting for regions of ~1000 bp length, log 2 ratio of at least 0.2, and a Wilson FDR of >13. 122 regions were selected, and of those, the six regions with the highest log 2 ratio and maximum methylation difference from normal seminal plasma cell-free DNA were selected for cluster analysis, Table 4 depicts details of the six regions selected. Average methylation values for CpG values within each of the 6 regions for each of the samples were calculated, as well as for 12 other background methylation samples of normal seminal plasma cell free DNA. The hypomethylation and hypermethylation of the promoters of ZFP64, MOB3B, and HLF were determined for the samples. In addition, the hypomethylation and hypermethylation of the genes TCAF-1, CHST-11, and ALOX-5 were determined for the samples. All average region CpG values were used in an unsupervised cluster analysis generating a dendrogram and heatmap using R's heatmap function which is shown in FIG. 6. In FIG. 6, above "Sample ID", samples from normal prostate tissue are shown in white, samples from cancerous prostate tissue are shown in black, and samples from seminal cell-free DNA is shown in gray. Hypermethylation of the promoters of ZFP64, MOB3B, and HLF and the genes TCAF-1, CHST-11, and ALOX-5 was identified in tumor samples, which cluster to the right of the figure. The seminal cell free DNA samples, which came from cancer free patients, clustered to the left near normal prostate tissue samples. Portions of DNA that discriminate between healthy and cancerous prostate tissue were able to be identified in the background of seminal plasma. The identification of hypermethylation of these regions in tumor samples and the ability to screen these regions in seminal cell free DNA to identify cancerous prostate cells in samples is surprising and unexpected.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for detecting a sperm cell comprising:
a) obtaining a biological sample from a subject, wherein the biological sample comprises seminal fluid;
b) extracting cell free DNA from the biological sample;
c) detecting a methylation pattern of a region of the extracted cell free DNA from the biological sample with a first computer program, executed on a computer, wherein the methylation pattern comprises the presence or the absence of methylation of at least one region of the extracted cell free DNA, wherein the detecting comprises obtaining methylation data from a presence or an absence of a methylated base by a sodium bisulfite conversion, a sequencing, a differential enzymatic cleavage of DNA, an affinity capture of methylated DNA, an array, or any combination thereof;
d) comparing the methylation pattern of the region of the extracted cell free DNA from the biological sample to a control pattern of DNA methylation with a second computer program, executed on a computer thereby determining the presence or the absence of the sperm cell in the biological sample by the methylation pattern;
e) transferring the result of the presence or the absence of the sperm cell in the biological sample to a user interface on an electronic display via a communication network; and
wherein the at least one region of the extracted cell free DNA comprises chr1: 182921660-182923994, chr1: 18807594-18809765, chr1: 190067323-190068181, chr1:247681102-247681932, chr1:35441734-35443497, chr1:9130738-9132197, chr1:92682167-92683822, chr10:13771107-13771466, chr10: 29084707-29085500, chr10:85324700-85325063, chr11:70415188-70416310, chr11:92615215-92617119, chr12:52472758-52474048, chr13: 36787282-36789909, chr16:89345548-89346492, chr16:90172237-90173535, chr17:43318045-43319383, chr17:74302589-74304620, chr17: 7909776-7910041, chr19:10463037-10465258, chr19: 2926081-2927446, chr19:36612371-36612912, chr19: 50058328-50060307, chr2: 128158047-128159059, chr20:55684764-55685923, chr22:32749516-32750882, chr22:50008841-50010192, chr3: 77145918-77148085, chr3:9027157-9027577, chr4: 128650393-128652120, chr4:151500192-151505193, chr4: 189580331-189580876, chr4: 190731443-190732882, chr5:121186479-121188229, chr5: 5057256-5057720, chr7:5540163-5541567, chr7: 5645728-5648123, chr7:64330493-64331111, chr7: 6524925-6525026, chr7:6865886-6867075, chr7: 72741781-72743404, chr7:75023589-75024730, chr8: 109143682-109144231, chr9: 138590204-138594308, chr9:72129977-72131656, chrX:129471948-129472963, chrX: 134974589-134976103, chrX: 31089692-31090940, chrX:40481859-40483213, chrX:42636927-42638572 or any combination thereof.

2. The method of claim 1, wherein the absence of methylation of the at least one region indicates the presence of the sperm cell in the biological sample.

3. The method of claim 1, wherein the at least one region comprises a plurality of CpG sites for methylation.

4. The method of claim 3, wherein at least about 75% of the plurality of CpG sites for methylation are unmethylated.

5. The method of claim 3, wherein at least about 75% of the plurality of CpG sites for methylation are methylated.

6. The method of claim 1, wherein the methylation pattern is identified in at least: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 regions of the extracted cell free DNA.

7. The method of claim 1, wherein the methylation pattern is identified in at least 3 regions of the extracted cell free DNA.

8. The method of claim 1, wherein the methylation pattern is identified in at least 5 regions of the extracted cell free DNA.

9. The method of claim 1, wherein the control pattern of DNA methylation is from a sperm cell.

10. The method of claim 1, wherein the method further comprises performing a treatment on the subject, wherein the treatment comprises a vasectomy reversal, a vasectomy, a microsurgical testicular sperm extraction (microTESE), a testicular sperm extraction (TESE), a transurethral resection of the ejaculatory ducts (TURED), a circumcision, a surgical correction for scarring, a testosterone replacement, or any combination thereof.

11. A forensic analysis method of identifying a sperm cell from an article comprising:
a) extracting cell free DNA from the article;
b) detecting a methylation pattern of a region of the cell free DNA with a first computer program, executed on a computer, wherein the methylation pattern comprises the presence or the absence of methylation of at least one region of DNA of the cell free DNA, wherein the detecting comprises obtaining methylation data from a presence or an absence of a methylated base by a sodium bisulfite conversion, a sequencing, a differential enzymatic cleavage of DNA, an affinity capture of methylated DNA, an array, or any combination thereof;
c) comparing the methylation pattern of the region of the extracted cell free DNA from the article to a control pattern of methylated DNA associated with a sperm cell with a second computer program, executed on a computer;
d) determining the presence or absence of the sperm cell from the article with a third computer program, executed on a computer, wherein the methylation pattern indicates the presence or absence of the sperm cell from the article;
e) transferring the result of the presence or the absence of the sperm cell from the article to a user interface on an electronic display via a communication network, which is a method for forensic analysis; and wherein the at least one region of the extracted cell free DNA comprises chr1:182921660-182923994, chr1: 18807594-18809765, chr1: 190067323-190068181, chr1:247681102-247681932, chr1:35441734-35443497, chr1:9130738-9132197, chr1:92682167-92683822, chr10:13771107-13771466, chr10: 29084707-29085500, chr10:85324700-85325063, chr11:70415188-70416310, chr11:92615215-92617119. chr12:52472758-52474048, chr13: 36787282-36789909, chr16:89345548-89346492, chr16:90172237-90173535, chr17:43318045-43319383, chr17:74302589-74304620, chr17: 7909776-7910041, chr19: 10463037-10465258, chr19: 2926081-2927446, chr19:36612371-36612912, chr19: 50058328-50060307, chr2:128158047-128159059, chr20:55684764-55685923, chr22:32749516-32750882, chr22:50008841-50010192, chr3: 77145918-77148085, chr3:9027157-9027577, chr4: 128650393-128652120, chr4: 151500192-151505193, chr4:189580331-189580876, chr4:190731443-190732882, chr5:121186479-121188229, chr5: 5057256-5057720, chr7:5540163-5541567. chr7: 5645728-5648123, chr7:64330493-64331111, chr7: 6524925-6525026, chr7:6865886-6867075, chr7: 72741781-72743404, chr7:75023589-75024730 chr8: 109143682-109144231, chr9: 138590204-138594308, chr9:72129977-72131656. chrX: 129471948-129472963, chrX:134974589-134976103, chrX: 31089692-31090940, chrX:40481859-40483213, chrX:42636927-42638572 or any combination thereof.

12. The method of claim 11, wherein the article comprises an article of evidence.

13. The method of claim 12, wherein the article of evidence comprises a clothing, a bed sheet, a weapon, or a tool.

14. The method of claim 12, wherein the article of evidence is obtained from a sexual assault forensic exam.

15. The method of claim 11, wherein the absence of methylation of the at least one region indicates the presence of the sperm cell from the article.

16. The method of claim 11, wherein the methylation pattern comprises the presence or the absence of methylation of at least three regions of the cell free DNA.

17. The method of claim 11, wherein the methylation pattern is identified in at least: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 regions of the extracted cell free DNA.

* * * * *

```
                          SEQUENCE LISTING

Sequence total quantity: 46
SEQ ID NO: 1            moltype = DNA  length = 25
FEATURE                 Location/Qualifiers
misc_feature            1..25
                        note = Description of Artificial Sequence: Syntheticprimer
source                  1..25
                        mol_type = other DNA
                        organism = synthetic construct
SEQUENCE: 1
ttggtttgga gttaagattt tagga                                              25

SEQ ID NO: 2            moltype = DNA  length = 25
FEATURE                 Location/Qualifiers
misc_feature            1..25
                        note = Description of Artificial Sequence: Syntheticprimer
source                  1..25
                        mol_type = other DNA
                        organism = synthetic construct
SEQUENCE: 2
ccaaacccac taaatcaaaa tctac                                              25

SEQ ID NO: 3            moltype = DNA  length = 26
FEATURE                 Location/Qualifiers
misc_feature            1..26
                        note = Description of Artificial Sequence: Syntheticprimer
source                  1..26
                        mol_type = other DNA
                        organism = synthetic construct
SEQUENCE: 3
ggtttttgga gagggttatt tattag                                             26

SEQ ID NO: 4            moltype = DNA  length = 24
FEATURE                 Location/Qualifiers
misc_feature            1..24
                        note = Description of Artificial Sequence: Syntheticprimer
source                  1..24
                        mol_type = other DNA
                        organism = synthetic construct
SEQUENCE: 4
taaaccacaa caataccaaa ccac                                               24

SEQ ID NO: 5            moltype = DNA  length = 25
FEATURE                 Location/Qualifiers
misc_feature            1..25
                        note = Description of Artificial Sequence: Syntheticprimer
source                  1..25
                        mol_type = other DNA
                        organism = synthetic construct
SEQUENCE: 5
tttttgtggt ttaggtaaag tttta                                              25

SEQ ID NO: 6            moltype = DNA  length = 30
FEATURE                 Location/Qualifiers
misc_feature            1..30
                        note = Description of Artificial Sequence: Syntheticprimer
source                  1..30
                        mol_type = other DNA
                        organism = synthetic construct
SEQUENCE: 6
cttacaatta aaaaaacaaa ttattactat                                         30

SEQ ID NO: 7            moltype = DNA  length = 21
FEATURE                 Location/Qualifiers
misc_feature            1..21
```

```
                        note = Description of Artificial Sequence: Syntheticprimer
source                  1..21
                        mol_type = other DNA
                        organism = synthetic construct
SEQUENCE: 7
gtttagggat aaattgggag t                                                   21

SEQ ID NO: 8            moltype = DNA   length = 22
FEATURE                 Location/Qualifiers
misc_feature            1..22
                        note = Description of Artificial Sequence: Syntheticprimer
source                  1..22
                        mol_type = other DNA
                        organism = synthetic construct
SEQUENCE: 8
accccctaaa cctctaccta cc                                                  22

SEQ ID NO: 9            moltype = DNA   length = 25
FEATURE                 Location/Qualifiers
misc_feature            1..25
                        note = Description of Artificial Sequence: Syntheticprimer
source                  1..25
                        mol_type = other DNA
                        organism = synthetic construct
SEQUENCE: 9
ttaaattaag gataaattaa gattt                                               25

SEQ ID NO: 10           moltype = DNA   length = 25
FEATURE                 Location/Qualifiers
misc_feature            1..25
                        note = Description of Artificial Sequence: Syntheticprimer
source                  1..25
                        mol_type = other DNA
                        organism = synthetic construct
SEQUENCE: 10
ccctaaacta aaataaaac cccac                                                25

SEQ ID NO: 11           moltype = DNA   length = 25
FEATURE                 Location/Qualifiers
misc_feature            1..25
                        note = Description of Artificial Sequence: Syntheticprimer
source                  1..25
                        mol_type = other DNA
                        organism = synthetic construct
SEQUENCE: 11
aaaagtttag taatatttta ggggg                                               25

SEQ ID NO: 12           moltype = DNA   length = 25
FEATURE                 Location/Qualifiers
misc_feature            1..25
                        note = Description of Artificial Sequence: Syntheticprimer
source                  1..25
                        mol_type = other DNA
                        organism = synthetic construct
SEQUENCE: 12
aaataaactc ctcaatttca tcaac                                               25

SEQ ID NO: 13           moltype = DNA   length = 30
FEATURE                 Location/Qualifiers
misc_feature            1..30
                        note = Description of Artificial Sequence: Syntheticprimer
source                  1..30
                        mol_type = other DNA
                        organism = synthetic construct
SEQUENCE: 13
ttgttgagtg ggaagtattt ttaaagtaat                                          30

SEQ ID NO: 14           moltype = DNA   length = 25
FEATURE                 Location/Qualifiers
misc_feature            1..25
                        note = Description of Artificial Sequence: Syntheticprimer
source                  1..25
                        mol_type = other DNA
                        organism = synthetic construct
SEQUENCE: 14
ttgtttagag ttaggtggga taggg                                               25

SEQ ID NO: 15           moltype = DNA   length = 28
FEATURE                 Location/Qualifiers
```

```
misc_feature            1..28
                        note = Description of Artificial Sequence: Syntheticprimer
source                  1..28
                        mol_type = other DNA
                        organism = synthetic construct
SEQUENCE: 15
tatttttagg tattggtagt agggqttt                                        28

SEQ ID NO: 16           moltype = DNA  length = 31
FEATURE                 Location/Qualifiers
misc_feature            1..31
                        note = Description of Artificial Sequence: Syntheticprimer
source                  1..31
                        mol_type = other DNA
                        organism = synthetic construct
SEQUENCE: 16
ccctactacc aatacctaaa aataaaaaaa a                                    31

SEQ ID NO: 17           moltype = DNA  length = 30
FEATURE                 Location/Qualifiers
misc_feature            1..30
                        note = Description of Artificial Sequence: Syntheticprimer
source                  1..30
                        mol_type = other DNA
                        organism = synthetic construct
SEQUENCE: 17
tcccaatata aaataaatt ttctttcaaa                                       30

SEQ ID NO: 18           moltype = DNA  length = 28
FEATURE                 Location/Qualifiers
misc_feature            1..28
                        note = Description of Artificial Sequence: Syntheticprimer
source                  1..28
                        mol_type = other DNA
                        organism = synthetic construct
SEQUENCE: 18
ataaccaaaa aattccaatt aatatcac                                        28

SEQ ID NO: 19           moltype = DNA  length = 30
FEATURE                 Location/Qualifiers
misc_feature            1..30
                        note = Description of Artificial Sequence: Syntheticprimer
source                  1..30
                        mol_type = other DNA
                        organism = synthetic construct
SEQUENCE: 19
gtttatagtt atagggtag tatgtggttg                                       30

SEQ ID NO: 20           moltype = DNA  length = 30
FEATURE                 Location/Qualifiers
misc_feature            1..30
                        note = Description of Artificial Sequence: Syntheticprimer
source                  1..30
                        mol_type = other DNA
                        organism = synthetic construct
SEQUENCE: 20
accataatcc taaaattcct actaatcttc                                      30

SEQ ID NO: 21           moltype = DNA  length = 30
FEATURE                 Location/Qualifiers
misc_feature            1..30
                        note = Description of Artificial Sequence: Syntheticprimer
source                  1..30
                        mol_type = other DNA
                        organism = synthetic construct
SEQUENCE: 21
atggttaaga ttgtagaatt ggaaaaatag                                      30

SEQ ID NO: 22           moltype = DNA  length = 22
FEATURE                 Location/Qualifiers
misc_feature            1..22
                        note = Description of Artificial Sequence: Syntheticprimer
source                  1..22
                        mol_type = other DNA
                        organism = synthetic construct
SEQUENCE: 22
taaactcccc tccaaaccct ac                                              22

SEQ ID NO: 23           moltype = DNA  length = 27
```

```
FEATURE              Location/Qualifiers
misc_feature         1..27
                     note = Description of Artificial Sequence: Syntheticprimer
source               1..27
                     mol_type = other DNA
                     organism = synthetic construct
SEQUENCE: 23
gtttaggttt tttatttggt tttttag                                                  27

SEQ ID NO: 24        moltype = DNA  length = 28
FEATURE              Location/Qualifiers
misc_feature         1..28
                     note = Description of Artificial Sequence: Syntheticprimer
source               1..28
                     mol_type = other DNA
                     organism = synthetic construct
SEQUENCE: 24
taaaaacaaa aactctatcc aataactc                                                 28

SEQ ID NO: 25        moltype = DNA  length = 33
FEATURE              Location/Qualifiers
misc_feature         1..33
                     note = Description of Artificial Sequence: Syntheticprimer
source               1..33
                     mol_type = other DNA
                     organism = synthetic construct
SEQUENCE: 25
ttttgtttgt tttaagtgat tttagtattt ttt                                           33

SEQ ID NO: 26        moltype = DNA  length = 29
FEATURE              Location/Qualifiers
misc_feature         1..29
                     note = Description of Artificial Sequence: Syntheticprimer
source               1..29
                     mol_type = other DNA
                     organism = synthetic construct
SEQUENCE: 26
gagagttttt aattggttag gttagattg                                                29

SEQ ID NO: 27        moltype = DNA  length = 30
FEATURE              Location/Qualifiers
misc_feature         1..30
                     note = Description of Artificial Sequence: Syntheticprimer
source               1..30
                     mol_type = other DNA
                     organism = synthetic construct
SEQUENCE: 27
tttctaactc aacctccttt tacttaatac                                               30

SEQ ID NO: 28        moltype = DNA  length = 30
FEATURE              Location/Qualifiers
misc_feature         1..30
                     note = Description of Artificial Sequence: Syntheticprimer
source               1..30
                     mol_type = other DNA
                     organism = synthetic construct
SEQUENCE: 28
aaccctctac tttaaaaaaa acctaaatac                                               30

SEQ ID NO: 29        moltype = DNA  length = 30
FEATURE              Location/Qualifiers
misc_feature         1..30
                     note = Description of Artificial Sequence: Syntheticprimer
source               1..30
                     mol_type = other DNA
                     organism = synthetic construct
SEQUENCE: 29
aagtgttttt tggaggagtt atttatgagg                                               30

SEQ ID NO: 30        moltype = DNA  length = 30
FEATURE              Location/Qualifiers
misc_feature         1..30
                     note = Description of Artificial Sequence: Syntheticprimer
source               1..30
                     mol_type = other DNA
                     organism = synthetic construct
SEQUENCE: 30
ctattaacct aaacccaaaa accaaaatac                                               30
```

-continued

```
SEQ ID NO: 31              moltype = DNA   length = 29
FEATURE                    Location/Qualifiers
misc_feature               1..29
                           note = Description of Artificial Sequence: Syntheticprimer
source                     1..29
                           mol_type = other DNA
                           organism = synthetic construct
SEQUENCE: 31
gatttttgtt ttttaaggtt agggttatt                                            29

SEQ ID NO: 32              moltype = DNA   length = 30
FEATURE                    Location/Qualifiers
misc_feature               1..30
                           note = Description of Artificial Sequence: Syntheticprimer
source                     1..30
                           mol_type = other DNA
                           organism = synthetic construct
SEQUENCE: 32
aacctaactc caaatctcca aactatacta                                           30

SEQ ID NO: 33              moltype = DNA   length = 30
FEATURE                    Location/Qualifiers
misc_feature               1..30
                           note = Description of Artificial Sequence: Syntheticprimer
source                     1..30
                           mol_type = other DNA
                           organism = synthetic construct
SEQUENCE: 33
tatagggtga aatttaaggg gaatattatt                                           30

SEQ ID NO: 34              moltype = DNA   length = 25
FEATURE                    Location/Qualifiers
misc_feature               1..25
                           note = Description of Artificial Sequence: Syntheticprimer
source                     1..25
                           mol_type = other DNA
                           organism = synthetic construct
SEQUENCE: 34
cctacaccta caacaacaac ttcac                                                25

SEQ ID NO: 35              moltype = DNA   length = 30
FEATURE                    Location/Qualifiers
misc_feature               1..30
                           note = Description of Artificial Sequence: Syntheticprimer
source                     1..30
                           mol_type = other DNA
                           organism = synthetic construct
SEQUENCE: 35
ttttatttgg tttattgttt atggtttaat                                           30

SEQ ID NO: 36              moltype = DNA   length = 35
FEATURE                    Location/Qualifiers
misc_feature               1..35
                           note = Description of Artificial Sequence: Syntheticprimer
source                     1..35
                           mol_type = other DNA
                           organism = synthetic construct
SEQUENCE: 36
taataaatcc aactttattc tattcttcat ataac                                     35

SEQ ID NO: 37              moltype = DNA   length = 30
FEATURE                    Location/Qualifiers
misc_feature               1..30
                           note = Description of Artificial Sequence: Syntheticprimer
source                     1..30
                           mol_type = other DNA
                           organism = synthetic construct
SEQUENCE: 37
ttatttttat aggtaaattg gtgattttttg                                          30

SEQ ID NO: 38              moltype = DNA   length = 28
FEATURE                    Location/Qualifiers
misc_feature               1..28
                           note = Description of Artificial Sequence: Syntheticprimer
source                     1..28
                           mol_type = other DNA
                           organism = synthetic construct
SEQUENCE: 38
aaaaaaacct aaaacaaaac aacataac                                             28
```

```
SEQ ID NO: 39          moltype = DNA   length = 25
FEATURE                Location/Qualifiers
misc_feature           1..25
                       note = Description of Artificial Sequence: Syntheticprimer
source                 1..25
                       mol_type = other DNA
                       organism = synthetic construct
SEQUENCE: 39
gagaagggt tgggatagga ttgta                                                25

SEQ ID NO: 40          moltype = DNA   length = 26
FEATURE                Location/Qualifiers
misc_feature           1..26
                       note = Description of Artificial Sequence: Syntheticprimer
source                 1..26
                       mol_type = other DNA
                       organism = synthetic construct
SEQUENCE: 40
accatctaat ccaacaaatc atcaac                                              26

SEQ ID NO: 41          moltype = DNA   length = 30
FEATURE                Location/Qualifiers
misc_feature           1..30
                       note = Description of Artificial Sequence: Syntheticprimer
source                 1..30
                       mol_type = other DNA
                       organism = synthetic construct
SEQUENCE: 41
tgtttaggta ggttgatatt tttgatagtt                                          30

SEQ ID NO: 42          moltype = DNA   length = 27
FEATURE                Location/Qualifiers
misc_feature           1..27
                       note = Description of Artificial Sequence: Syntheticprimer
source                 1..27
                       mol_type = other DNA
                       organism = synthetic construct
SEQUENCE: 42
aatacacaac ccaacacatt ctaaaac                                             27

SEQ ID NO: 43          moltype = DNA   length = 30
FEATURE                Location/Qualifiers
misc_feature           1..30
                       note = Description of Artificial Sequence: Syntheticprimer
source                 1..30
                       mol_type = other DNA
                       organism = synthetic construct
SEQUENCE: 43
tggtttgttg aatatagaat tgaataaaat                                          30

SEQ ID NO: 44          moltype = DNA   length = 30
FEATURE                Location/Qualifiers
misc_feature           1..30
                       note = Description of Artificial Sequence: Syntheticprimer
source                 1..30
                       mol_type = other DNA
                       organism = synthetic construct
SEQUENCE: 44
ctaaacaaaa ttaaacaaca taaaaaccac                                          30

SEQ ID NO: 45          moltype = DNA   length = 30
FEATURE                Location/Qualifiers
misc_feature           1..30
                       note = Description of Artificial Sequence: Syntheticprimer
source                 1..30
                       mol_type = other DNA
                       organism = synthetic construct
SEQUENCE: 45
tttttatgt tttagttgtt tttttgtgg                                            30

SEQ ID NO: 46          moltype = DNA   length = 30
FEATURE                Location/Qualifiers
misc_feature           1..30
                       note = Description of Artificial Sequence: Syntheticprimer
```

```
source          1..30
                mol_type = other DNA
                organism = synthetic construct
SEQUENCE: 46
acaaataccc aatataccct atataatccc                                    30
```